(12) United States Patent
Belli et al.

(10) Patent No.: US 10,137,170 B2
(45) Date of Patent: Nov. 27, 2018

(54) LIPIDATED INCRETIN RECEPTOR LIGAND HUMAN IMMUNOGLOBULIN FC-REGION FUSION POLYPEPTIDES

(71) Applicants: INDIANA UNIVERSITY RESEARCH AND TECHNOLOGY CORPORATION, Indianapolis, IN (US); HOFFMANN-LA ROCHE INC., Little Falls, NJ (US)

(72) Inventors: Sara Belli, Oberrohrdorf (CH); Konrad Bleicher, Freiburg (DE); Richard D. Dimarchi, Carmel, IN (US); Eike Hoffmann, Herrsching a. Ammersee (DE); Eric A. Kitas, Aasch Baselland (CH); Anish A. Konkar, North Bethesda, MD (US)

(73) Assignees: INDIANA UNIVERSITY RESEARCH AND TECHNOLOGY CORPORATION, Indianapolis, IN (US); HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/102,340

(22) PCT Filed: Dec. 19, 2014

(86) PCT No.: PCT/US2014/071454
§ 371 (c)(1),
(2) Date: Jun. 7, 2016

(87) PCT Pub. No.: WO2015/095684
PCT Pub. Date: Jun. 25, 2015

(65) Prior Publication Data
US 2016/0310575 A1    Oct. 27, 2016

Related U.S. Application Data

(60) Provisional application No. 61/918,950, filed on Dec. 20, 2013.

(51) Int. Cl.
| | | |
|---|---|---|
| A61K 38/26 | (2006.01) | |
| C07K 14/605 | (2006.01) | |
| A61K 45/06 | (2006.01) | |
| A61K 47/54 | (2017.01) | |
| A61K 38/00 | (2006.01) | |

(52) U.S. Cl.
CPC .............. *A61K 38/26* (2013.01); *A61K 45/06* (2013.01); *A61K 47/543* (2017.08); *C07K 14/605* (2013.01); *A61K 38/00* (2013.01); *C07K 2319/30* (2013.01)

(58) Field of Classification Search
CPC ............................. A61K 38/26; C07K 14/605
See application file for complete search history.

(56) References Cited

U.S. PATENT DOCUMENTS

| | | | | |
|---|---|---|---|---|
| 2009/0098108 A1* | 4/2009 | O'Neil | ................... | A61K 38/26 |
| | | | | 424/130.1 |
| 2009/0181037 A1* | 7/2009 | Heavner | ................. | A61K 38/26 |
| | | | | 424/178.1 |
| 2014/0051834 A1* | 2/2014 | Hoffman | ................. | C07K 16/46 |
| | | | | 530/387.3 |

FOREIGN PATENT DOCUMENTS

| | | |
|---|---|---|
| WO | 2009/155258 A2 | 12/2009 |
| WO | 2010/011439 A2 | 1/2010 |
| WO | 2013/192130 A1 | 12/2013 |
| WO | 2013/192131 A1 | 12/2013 |

OTHER PUBLICATIONS

PCT International Search Report and Written Opinion completed by the ISA/EP dated Apr. 9, 2015 and issued in connection with PCT/US2014/071454.
Wolfgang Glaesner, et al. "Engineering and characterization of the long-acting glucagon-like peptide-1 analogue LY2189265, an Fc fusion protein", Diabetes/Metabolism Research and Review, vol. 26, No. 4, Apr. 30, 2010 (Apr. 30, 2010), pp. 287-296, XP055181624.
B. Finan, et al. "Unimolecular Dual Incretins Maximize Metabolic Benefits in Rodents, Monkeys, and Humans", Science Translational Medicine, vol. 5, No. 209, Oct. 30, 2013 (Oct. 30, 2013), pp. 209ra151-209ra151.
Database Geneseq [Online] Jul. 18, 2013 (Jul. 18, 2013), "Human glucagon analog peptide SEQ: 1120.", XP002738200, retrieved from EBI accession No. GSP:BA089973 Database accession No. BA089973 the whole document.
Brian P. Ward, et al. "Peptide lipidation stabilizes structure to enhance biological function", Molecular Metabolism, vo 1. 2, No. 4, Sep. 5, 2013 (Sep. 5, 2013), pp. 468-479.
David A. Levary, et al. "Protein-Protein Fusion Catalyzed by Sortase A", PLOS One, Public Library of Science, US, vol. 6, No. 4, Apr. 1, 2011 (Apr. 1, 2011), pp. 18342.1-e18342.6.
H. Liu "N-acetyl-GLP-1: a DPP IV-resistant analogue of glucagon-like peptide-1 (GLP-1) with improved effects on pancreatic [beta]-cell-associated gene expression", Cell Biology International, vol. 28, No. 1, Jan. 1, 2004 (Jan. 1, 2004), pp. 69-73.

* cited by examiner

*Primary Examiner* — Gyan Chandra
(74) *Attorney, Agent, or Firm* — Barnes & Thornburg LLP

(57) ABSTRACT

Herein is reported a fusion polypeptide comprising i) one, two, three or four incretin receptor ligand polypeptides, and ii) one human immunoglobulin Fc-region, wherein at least one of the incretin receptor ligand polypeptides comprises an amino acid that is covalently conjugated to a lipid, and wherein each of the one, two, three or four incretin receptor ligand polypeptides is covalently conjugated by a peptide bond to a terminus of the human immunoglobulin Fc-region, whereby to each terminus of the human immunoglobulin Fc-region only a single incretin receptor ligand polypeptide is conjugated.

3 Claims, 9 Drawing Sheets
Specification includes a Sequence Listing.

a)

b)

a)

b)

(A)

(B)

LIPIDATED INCRETIN RECEPTOR LIGAND HUMAN IMMUNOGLOBULIN FC-REGION FUSION POLYPEPTIDES

CROSS-REFERENCE TO RELATED APPLICATIONS

This application is a U.S. national counterpart application of international application serial No. PCT/US2014/071454 filed Dec. 19, 2014, which claims priority to U.S. Provisional Patent Application No. 61/918,950 filed on Dec. 20, 2013, disclosures which are expressly incorporated by reference in their entirety.

INCORPORATION BY REFERENCES OF MATERIAL SUBMITTED ELECTRONICALLY

Incorporated by reference in its entirety is a computer-readable nucleotide/amino acid sequence listing submitted concurrently herewith and identified as follows: 95 kilobytes ACII (Text) file named "232708_31909_SeqListing.txt," created on Dec. 18, 2014.

FIELD OF THE INVENTION

Herein are reported lipidated incretin receptor ligand human immunoglobulin Fc-region fusion polypeptides and their use.

BACKGROUND OF THE INVENTION

Insulinotropic polypeptides have insulinotropic activity, i.e., have the ability to stimulate, or to cause the stimulation of, the synthesis or expression of the hormone insulin. Insulinotropic peptides include, but are not limited to, GLP-1, exendin-3, exendin-4, and precursors, derivatives, or fragments thereof.

Pro-glucagon-derived peptides, including glucagon and glucagon-like peptide-1 (GLP-1), are found in many metabolic pathways involved in different physiological functions, such as insulin secretion and regulation of food intake.

Pre-pro-glucagon is a 158 amino acid polypeptide that is processed to a number of different active compounds. GLP-1, e.g., corresponds to amino acid residues 72 through 108 of pre-pro-glucagon. GLP-1 among other functions results in the stimulation of insulin synthesis and secretion and inhibition of food intake. GLP-1 has been shown to reduce hyperglycemia (elevated glucose levels) in diabetics.

Glucose-dependent insulinotropic peptide (GIP) is a 42-amino acid gastrointestinal regulatory peptide that stimulates insulin secretion from pancreatic beta cells in the presence of glucose. It is derived by proteolytic processing from a 133-amino acid precursor, pre-pro-GIP.

In WO 2010/011439 GIP-based mixed agonists for treatment of metabolic disorders and obesity are reported. It is reported that modifications to the native glucagon sequence produce glucagon peptides that can exhibit potent glucagon activity equivalent to or better than the activity of native glucagon, potent GIP activity equivalent to or better than the activity of native GIP, and/or potent GLP-1 activity equivalent to or better than the activity of native GLP-1. The data provided is reported to show that peptides having both GIP activity and GLP-1 activity are particularly advantageous for inducing weight loss or preventing weight gain, as well as for treating hyperglycemia, including diabetes, whereby the combination of GIP agonist activity with GLP-1 agonist activity produces a greater effect on weight reduction than GLP-1 alone.

The conjugation of insulinotropic polypeptides to antibodies or antibody fragments is hypothetically outlined in e.g. WO 2010/011439, U.S. Pat. No. 6,329,336 and U.S. Pat. No. 7,153,825.

Discovery of dual-action membrane-anchored modulators of incretin receptors is reported by Fortin, J-P., et al. (PlosOne 6 (2011) e24693). Finan, B., et al., report that unimolecular dual incretins maximize metabolic benefits in rodents, monkeys, and humans (Sci. Transl. Med. 5 (2013) 209ra151).

SUMMARY OF THE INVENTION

One aspect as reported herein is a fusion polypeptide comprising
  one, two, three or four incretin receptor ligand polypeptides, and
  one human immunoglobulin Fc-region,
wherein at least one of the incretin receptor ligand polypeptides comprises an amino acid that is covalently conjugated to a lipid, and
wherein each of the one, two, three or four incretin receptor ligand polypeptides is covalently conjugated by a peptide bond to a terminus of the human immunoglobulin Fc-region, whereby to each terminus of the human immunoglobulin Fc-region only a single incretin receptor ligand polypeptide is conjugated.

In one embodiment the fusion polypeptide in vivo associates with an endogenous polypeptide.

In one embodiment the conjugation to a lipid is via a functional group in the side chain of the amino acid.

In one embodiment the amino acid residues of the incretin receptor ligand polypeptide that is covalently conjugated to a lipid is a non-naturally occurring amino acid residue.

In one embodiment the lipid is selected from the group comprising fatty acids, glycerolipids, glycerophospholipids, sphingolipids, sterol lipids, prenol lipids, saccharolipids and polyketides.

In one embodiment the conjugation to a lipid is selected from the group comprising myristoylation (14:0), palmitoylation (16:0), prenylation, octaonylation, archaeolyation, cholesterylation.

In one preferred embodiment the conjugation to a lipid is palmitoylation.

In one embodiment
  i) in case the incretin receptor ligand polypeptide is conjugated via its C-terminus to the human immunoglobulin Fc-region the amino acid sequence LPXTG (SEQ ID NO: 75), optionally, LPETG (SEQ ID NO: 74) is between the C-terminus of the incretin receptor ligand polypeptide and the N-terminus of the human immunoglobulin Fc-region, and
  ii) in case the incretin receptor ligand polypeptide is conjugated via its N-terminus to the human immunoglobulin Fc-region the amino acid sequence LPXTG (SEQ ID NO: 75), optionally, LPETG (SEQ ID NO: 74) is between the N-terminus of the incretin receptor ligand polypeptide and the C-terminus of the human immunoglobulin Fc-region.

In one embodiment the incretin receptor ligand polypeptide is a naturally occurring incretin receptor ligand polypeptide or a synthetic incretin receptor ligand polypeptide.

In one embodiment the incretin receptor ligand polypeptide comprises an amino acid sequence selected from the group consisting of SEQ ID NOs: 1-39, 76, 77 and 120-125.

In one embodiment the fusion polypeptide comprises the amino acid sequence LPETG (SEQ ID NO: 74) between the amino acid sequence of the incretin receptor ligand polypeptide and the amino acid sequence of the human immunoglobulin Fc-region.

In one embodiment the fusion polypeptide comprises one of the polypeptides Gly-Gly or Gly-Gly-Ser or Gly-Gly-Gly, Gly-Gly-Gly-Ser (SEQ ID NO: 88), Gly-Gly-Gly-Gly (SEQ ID NO: 85), or Gly-Gly-Gly-Gly-Ser (SEQ ID NO: 90) C- or N-terminally to LPETG (SEQ ID NO: 74).

In one embodiment the fusion polypeptide comprises (GGGS)n, wherein n=1-6 (SEQ ID NOs: 57-60, 88 and 89), (GGGGS)m, wherein m=1-6 (SEQ ID NOs: 61-64, 90 and 91), or (GGGGGS)o, wherein o=1-6 (SEQ ID NOs: 65-67 and 92-94).

In one embodiment the fusion polypeptide comprises any one of SEQ ID NOs: 57-67.

In one embodiment the fusion polypeptide comprises Gly or Gly-Gly C- or N-terminally to LPXTG (SEQ ID NO: 75).

In one embodiment the human immunoglobulin Fc-region is a human immunoglobulin Fc-region with a mutation of the amino acid residue at position 329 and at least one further mutation of at least one amino acid selected from the group comprising amino acid residues at position 228, 233, 234, 235, 236, 237, 297, 318, 320, 322 and 331 to a different residue, wherein the residues in the Fc-region are numbered according to the EU index of Kabat.

In one embodiment the human immunoglobulin Fc-region has a reduced affinity to the human FcγRIIIA and/or FcγRIIA and/or FcγRI compared to a human immunoglobulin Fc-region fusion polypeptide comprising a wild-type human immunoglobulin IgG Fc-region.

In one embodiment the human immunoglobulin Fc-region comprises at least one mutation selected from the group comprising S228P, E233P, L234A, L235A, L235E, N297A, N297D, P329G and P331S.

In one preferred embodiment the human immunoglobulin Fc-region comprises the mutations L234A, L235A and P329G if the Fc-region is of human IgG1 isotype or the mutations S228P, L235E and P329G if the Fc-region is of human IgG4 isotype.

In one embodiment thrombocyte aggregation induced by the human immunoglobulin Fc-region is reduced compared to the thrombocyte aggregation induced by a wild-type human immunoglobulin Fc-region.

In one embodiment the fusion polypeptide comprises one or two incretin receptor ligand polypeptides.

In one preferred embodiment each of the incretin receptor ligand polypeptides is conjugated to the N-terminus of one polypeptide chain of the human immunoglobulin Fc-region.

In one embodiment each of the incretin receptor ligand polypeptides is conjugated to the C-terminus of one polypeptide chain of the human immunoglobulin Fc-region.

In one embodiment the incretin receptor ligand polypeptides are selected independently from each other from GIP, GLP-1, exendin-3, exendin-4, dual GIP-GLP-1 agonists, triple GIP-GLP-1-glucagon receptor agonists, chimeric GIP/GLP agonists, and precursors, derivatives, or functional fragments thereof.

In one embodiment the human immunoglobulin Fc-region comprises an amino acid sequence selected from the group consisting of SEQ ID NOs: 42-56.

In one embodiment the fusion polypeptide comprises a linker between the human immunoglobulin Fc-region and the incretin receptor ligand polypeptide, wherein the linker comprises an amino acid sequence selected from the group consisting of SEQ ID NOs: 57-69 and 82-94.

In one embodiment the incretin receptor ligand polypeptide is derived from GLP-1(7-37) (HAEGTFTSDVS-SYLEGQAAKEFIAWLVKGRG, SEQ ID NO: 01), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from GLP-1(7-36) (HAEGTFTSDVS-SYLEGQAAKEFIAWLVKGR, SEQ ID NO: 02), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from exendin-3 (HSDGTFTSDLSKQMEEE-AVRLFIEWLKNGG PSSGAPPPS, SEQ ID NO: 03), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from exendin-4 (HGEGTFTSDLSKQMEEE-AVRLFIEWLKNGGPSSGAPPPS, SEQ ID NO: 04), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from any one of SEQ ID NOs: 01-04, wherein 1 to 10 (e.g., 1, 2, 3, 4, 5, 6, 7, 8, 9, 10) amino acid modifications relative to SEQ ID NO: 01-04 have been made, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from exendin-4(1-31) desGlu(17) Tyr(32) (HGEGTFTSDLSKQMEEAVRLFIEWLKNGGPY, SEQ ID NO: 05), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from exendin-4(1-30) Tyr(31) (HGEGTFTS-DLSKQMEEEAVRLFIEWLKNGGY, SEQ ID NO: 06), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from exendin-4(9-39) (DLSKQMEEEAVR-LFIEWLKNGGPSSGAPPPS, SEQ ID NO: 07), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence SYLEGQAAKEFIAWLVXGR (SEQ ID NO: 08) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence SSYLEGQAAKEFIAWLVXGR (SEQ ID NO: 09) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence VSSYLEGQAAKEFIAWLVXGR (SEQ ID NO: 10) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence DVSSYLEGQAAKEFIAWLVXGR (SEQ ID NO: 11) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence SDVSSYLEGQAAKEFIAWLVXGR (SEQ ID NO: 12) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence TSDVSSYLEGQAAKEFIAWLVXGR (SEQ ID NO: 13) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence FTSDVSSYLEGQAAKEFIAWLVXGR (SEQ ID NO: 14) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence TFTSDVSSYLEGQAAKEFIAWLVXGR (SEQ ID NO: 15) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence GTFTSDVSSYLEGQAAKEFIAWLVXGR (SEQ ID NO: 16) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence EGTFTSDVSSYLEGQAAKEFIAWLVXGR (SEQ ID NO: 17) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence AEGTFTSDVSSYLEGQAAKEFIAWLVXGR (SEQ ID NO: 18) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence HAEGTFTSDVSSYLEGQAAKEFIAWLVXGR (SEQ ID NO: 19) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence HDAEGTFTSDVSSYLEGQAAKEFIAWLVXGR (SEQ ID NO: 20) with X=K or R, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence HAEGTFTSDVSSYLEGQAAKEFIAWLVKGRPSSGAPPPS (SEQ ID NO: 21) (hybrid GLP-1/exendin polypeptide), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence HDEFERHAEGTFTSDVSSYLEGQAAKEFIAWLVKGRK (SEQ ID NO: 22), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence HAEGTFTSDVSSYLEGQAAKEFIAWLVKGRK (SEQ ID NO: 23), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence HGEGTFTSDLSKQMEEEAVRLFIEWLKNGGPSSGAPPPSK (SEQ ID NO: 24), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence HSDGTFTSDLSKQMEEEAVRLFIEWLKNGGPSSGAPPPSK (SEQ ID NO: 25), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence HGEGTFTS-DLSKEMEEEVRLFIEWLKNGGPY (SEQ ID NO: 26), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence HGEGTFTS-DLSKEMEEEVRLFIEWLKNGGY (SEQ ID NO: 27), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from the amino acid sequence DLSKQMEEEAVRLFIEWLKGGPSSGPPPS (SEQ ID NO: 28), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from native glucagon (SEQ ID NO: 76) with 1 to 10 (e.g., 1, 2, 3, 4, 5, 6, 7, 8, 9, 10) amino acid modifications relative to SEQ ID NO: 76, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from GLP-1 (SEQ ID NO: 1 or 2) with 1 to 10 (e.g., 1, 2, 3, 4, 5, 6, 7, 8, 9, 10) amino acid modifications relative to SEQ ID NO: 1 or 2, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from GIP (SEQ ID NO: 77) with 1 to 10 (e.g., 1, 2, 3, 4, 5, 6, 7, 8, 9, 10) amino acid modifications relative to SEQ ID NO: 77, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is derived from exendin-3 or -4 (SEQ ID NO: 3 or 4) with 1 to 10 (e.g., 1, 2, 3, 4, 5, 6, 7, 8, 9, 10) amino acid modifications relative to SEQ ID NO: 3 or 4, wherein at least one amino acid residue is conjugated to a lipid or is changed to a non-naturally occurring amino acid residue conjugated to a lipid and wherein the derived polypeptide has incretin receptor ligand activity.

In one preferred embodiment the incretin receptor ligand polypeptide is derived from glucagon (SEQ ID NO: 76) wherein the analog comprises SEQ ID NO: 76 with (a) an amino acid modification at position 1 that confers GIP agonist activity, (b) a modification which stabilizes the alpha helix structure of the C-terminal portion (amino acids 12-29) of the analog, and (c) optionally, 1 to 10 (e.g., 1, 2, 3, 4, 5, 6, 7, 8, 9, 10) further amino acid modifications relative to SEQ ID NO: 76, wherein at least one amino acid residue is conjugated to a lipid or is changed to a non-naturally occurring amino acid residue conjugated to a lipid and wherein the derived polypeptide has incretin receptor ligand activity.

In certain embodiments, the modification which stabilizes the alpha helix structure is one which provides or introduces an intramolecular bridge, including, for example, a covalent intramolecular bridge, such as any of those described in WO2010/011439. The covalent intramolecular bridge in some embodiments is a lactam bridge. The lactam-bridge of the analog of these embodiments can be a lactam bridge as described herein. See, e.g., the teachings of lactam bridges under the section "Stabilization of the Alpha Helix Structure" in WO2010/011439. For example, the lactam-bridge may be one which is between the side chains of amino acids at positions i and i+4 or between the side chains of amino acids at positions j and j+3, wherein i is 12, 13, 16, 17, 20 or 24, and wherein j is 17. In certain embodiments, the lactam-bridge can be between the amino acids at positions 16 and 20, wherein one of the amino acids at positions 16 and 20 is substituted with Glu and the other of the amino acids at positions 16 and 20 is substituted with Lys.

In alternative embodiments, the modification which stabilizes the alpha helix structure is the introduction of one, two, three, or four α,α-disubstituted amino acids at position(s) 16, 20, 21, and 24 of the analog. In some embodiments, the α,α-disubstituted amino acid is AIB. In certain aspects, the α,α-disubstituted amino acid (e.g., AIB) is at position 20 and the amino acid at position 16 is substituted with a positive-charged amino acid, such as, for example, an amino acid of Formula IV, which is described herein. The amino acid of Formula IV may be homoLys, Lys, Orn, or 2,4-diaminobutyric acid (Dab).

In specific aspects of the invention, the amino acid modification at position 1 is a substitution of His with an amino acid lacking an imidazole side chain, e.g. a large, aromatic amino acid (e.g., Tyr).

In certain aspects, the analog of glucagon comprises amino acid modifications at one, two or all of positions 27, 28 and 29. For example, the Met at position 27 can be substituted with a large aliphatic amino acid, optionally Leu, the Asn at position 28 can be substituted with a small aliphatic amino acid, optionally Ala, the Thr at position 29 can be substituted with a small aliphatic amino acid, optionally Gly, or a combination of two or three of the foregoing. In specific embodiments, the analog of glucagon comprises Leu at position 27, Ala at position 28, and Gly or Thr at position 29.

In certain embodiments of the invention, the analog of glucagon comprises an extension of 1 to 21 amino acids C-terminal to the amino acid at position 29. The extension can comprise the amino acid sequence of GPSSGAPPPS (SEQ ID NO: 78) or XGPSSGAPPPS (SEQ ID NO: 79), for instance. Additionally or alternatively, the analog of glucagon can comprise an extension of which 1-6 amino acids of the extension are positive-charged amino acids. The positive-charged amino acids may be amino acids of Formula I,

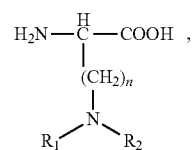

[Formula I]

wherein n is 1 to 16, or 1 to 10, or 1 to 7, or 1 to 6, or 2 to 6, each of R1 and R2 is independently selected from the group consisting of H, C1-C18 alkyl, (C1-C18 alkyl)OH, (C1-C18 alkyl)NH2, (C1-C18 alkyl)SH, (C0-C4 alkyl)(C3-

C6)cycloalkyl, (C0-C4 alkyl)(C2-C5 heterocyclic), (C0-C4 alkyl)(C6-C10 aryl)R7, and (C1-C4 alkyl)(C3-C9 heteroaryl), wherein R7 is H or OH, and the side chain of the amino acid of Formula IV comprises a free amino group. In exemplary aspects, the amino acid of Formula IV is Lys, homoLys, Orn, or Dab.

Furthermore, in some embodiments, the analog of glucagon (SEQ ID NO: 76) comprises any one or a combination of the following modifications relative to SEQ ID NO: 76:
  (a) Ser at position 2 substituted with D-Ser, Ala, D-Ala, Gly, N-methyl-Ser, AIB, Val, or α-amino-N-butyric acid;
  (b) Tyr at position 10 substituted with Trp, Orn, Glu, Phe, or Val:
  (c) Lys at position 12 substituted with Arg or Ile;
  (d) Ser at position 16 substituted with Glu, Gln, homoglutamic acid, homocysteic acid, Thr, Gly, or AIB;
  (e) Arg at position 17 substituted with Gln;
  (f) Arg at position 18 substituted with Ala, Ser, Thr, or Gly;
  (g) Gln at position 20 substituted with Ser, Thr, Ala, Lys, Citrulline, Arg, Orn, or AIB;
  (h) Asp at position 21 substituted with Glu, homoglutamic acid, homocysteic acid;
  (i) Val at position 23 substituted with Ile;
  (j) Gln at position 24 substituted with Asn, Ser, Thr, Ala, or AIB;
  (k) and a conservative substitution at any of positions 2 5, 9, 10, 11, 12, 13, 14, 15, 16, 8 19 20, 21, 24, 27, 28, and 29.

In exemplary embodiments, the analog of glucagon (SEQ ID NO: 76) having GIP agonist activity comprises the following modifications:
  (a) an amino acid modification at position 1 that confers GIP agonist activity,
  (b) a lactam bridge between the side chains of amino acids at positions i and i+4 or between the side chains of amino acids at positions j and j+3, wherein i is 12, 13, 16, 17, 20 or 24, and wherein j is 17,
  (c) amino acid modifications at one, two or all of positions 27, 28 and 29, e.g., amino acid modifications at position 27 and/or 28, and
  (d) 1-9 or 1-6 further amino acid modifications, e.g. 1, 2, 3, 4, 5, 6, 7, 8 or 9 further amino acid modifications, relative to SEQ ID NO: 76
and the EC50 of the analog for GIP receptor activation is about 10 nM or less. In exemplary aspects, the EC50 of the analog at the GIP receptor is less than about 50-fold different from its EC50 at the GLP-1 receptor.

The lactam-bridge of the analog of these embodiments can be a lactam bridge as described herein (see, e.g., the teachings of lactam bridges under the section "Stabilization of the Alpha Helix Structure" in WO 2010/011439). For example, the lactam-bridge can be between the amino acids at positions 16 and 20, wherein one of the amino acids at positions 16 and 20 is substituted with Glu and the other of the amino acids at positions 16 and 20 is substituted with Lys.

In one embodiment the incretin receptor ligand polypeptide is an analog of glucagon having GIP agonist activity, with the following modifications:
  (a) an amino acid modification at position 1 that confers GIP agonist activity,
  (b) one, two, three, or all of the amino acids at positions 16, 20, 21, and 24 of the analog is substituted with an α,α-disubstituted amino acid,
  (c) amino acid modifications at one, two or all of positions 27, 28 and 29, and
  (d) 1-9 or 1-6 further amino acid modifications, e.g. 1, 2, 3, 4, 5, 6, 7, 8 or 9 further amino acid modifications, relative to native glucagon (SEQ ID NO: 76),
wherein the EC50 of the analog for GIP receptor activation is about 10 nM or less. In exemplary aspects, the EC50 of the analog at the GIP receptor is less than about 50-fold different from its EC50 at the GLP-1 receptor.

The α,α-disubstituted amino acid of the analog of these embodiments can be any α,α-disubstituted amino acid, including, but not limited to, amino iso-butyric acid (AIB), an amino acid disubstituted with the same or a different group selected from methyl, ethyl, propyl, and n-butyl, or with a cyclooctane or cycloheptane (e.g., 1-aminocyclooctane-1-carboxylic acid). In one embodiment the α,α-disubstituted amino acid is aminoisobutyric acid (aib).

In yet other exemplary embodiments, the analog of glucagon (SEQ ID NO: 76) having GIP agonist activity comprises the following modifications:
  (a) an amino acid modification at position 1 that confers GIP agonist activity,
  (b) an amino acid substitution of Ser at position 16 with an amino acid of Formula I:

[Formula I]

wherein n is 1 to 16, or 1 to 10, or 1 to 7, or 1 to 6, or 2 to 6, each of $R_1$ and $R_2$ is independently selected from the group consisting of H, $C_1$-$C_{18}$ alkyl, ($C_1$-$C_{18}$ alkyl)OH, ($C_1$-$C_{18}$ alkyl)$NH_2$, ($C_1$-$C_{18}$ alkyl)SH, ($C_0$-$C_4$ alkyl)($C_3$-$C_6$)cycloalkyl, ($C_0$-$C_1$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl), wherein $R_7$ is H or OH, and the side chain of the amino acid of Formula IV comprises a free amino group,
  (c) an amino acid substitution of the Gln at position 20 with an alpha, alpha-disubstituted amino acid,
  (d) amino acid modifications at one, two or all of positions 27, 28 and 29, e.g., amino acid modifications at position 27 and/or 28, and
  (e) 1-9 or 1-6 further amino acid modifications, e.g. 1, 2, 3, 4, 5, 6, 7, 8 or 9 further amino acid modifications,
and the EC50 of the analog for GIP receptor activation is about 10 nM or less. In exemplary aspects, the EC50 of the analog at the GIP receptor is less than about 50-fold different from its EC50 at the GLP-1 receptor.

The amino acid of Formula IV of the analog of these embodiments may be any amino acid, such as, for example, the amino acid of Formula IV, wherein n is 1, 2, 3, 4, 5, 6, 7, 8, 9, 10, 11, 12, 13, 14, 15, or 16. In certain embodiments, n is 2, 3, 4, or 5, in which case, the amino acid is Dab, Orn, Lys, or homoLys respectively.

The alpha, alpha-disubstituted amino acid of the analog of these embodiments may be any alpha, alpha-disubstituted amino acid, including, but not limited to, amino iso-butyric acid (AIB), an amino acid disubstituted with the same or a different group selected from methyl, ethyl, propyl, and n-butyl, or with a cyclooctane or cycloheptane (e.g., 1-aminocyclooctane-1-carboxylic acid). In certain embodiments, the alpha, alpha-disubstituted amino acid is AIB.

In one embodiment the incretin receptor ligand polypeptide is or comprises the amino acid sequence YXEGTFTS-DYSIYLDKQAAXEFVCWLLAGGPSSGAPPPSK (SEQ ID NO: 29) with X=aib, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXEGTFTS-DYSIYLDKQAAXEFVNWLLAGGPSSGAPPPSK (SEQ ID NO: 30) with X=aib, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXEGTFTS-DYSIYLDKQAAXEFVAWLLAGGPSSGAPPPSK (SEQ ID NO: 31) with X=aib, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXEGTFTS-DYSIYLDKQAAXEFVNWLLAGGG (SEQ ID NO: 32) with X=aib, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXEGTFTS-DYSIYLDKQAAXEFVAWLLAGG G (SEQ ID NO: 33) with X=aib, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXEGTFTS-DYSIYLDEQAAKEFVNWLLAGGPSSGAPPPSC (SEQ ID NO: 34) with X=aib, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXEGTFTS-DYSIYLDKQAAXEFVNWLLAGGPSSGAPPPSC (SEQ ID NO: 35) with X=aib, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXQGTFTS-DYSIYLDKQAAXEFVNWLLAGGPSSGAPPPSK (SEQ ID NO: 36) with X=aib, wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXQGTFTS-DYSIYLDEQAAKEFVNWLLAGGPSSGAPPPSC (SEQ ID NO: 37) with X=aib and with a lactam ring between the side chains of residues 16 and 20 (of SEQ ID NO: 37), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXQGTFIS-DYSIYLDEQAAKEFVNWLLAGGPSSGAPPPSC (SEQ ID NO: 38) with X=aib and with a lactam ring between the side chains of residues 16 and 20 (of SEQ ID NO: 38), wherein at least one amino acid residue is conjugated to a lipid or is changed to a non-naturally occurring amino acid residue conjugated to a lipid and wherein the derived polypeptide has incretin receptor ligand activity.

In one embodiment the incretin receptor ligand polypeptide is or comprises the amino acid sequence YXQGTFIS-DYSIYLDEQAAKEFVCWLLAG (SEQ ID NO: 39) with X=aib and with a lactam ring between the side chains of residues 16 and 20 (of SEQ ID NO: 39), wherein at least one amino acid residue is conjugated to a lipid or is changed to a non-naturally occurring amino acid residue conjugated to a lipid and wherein the derived polypeptide has incretin receptor ligand activity.

One aspect as reported herein is a lipidated incretin receptor ligand polypeptide comprising the amino acid sequence of Y-Aib-EGTFTSDK-(γEγE-C16)-SIYLD-KQAA-Aib-EFVNWLLAGGPSSGAPPPS (SEQ ID NO: 120).

One aspect as reported herein is a lipidated incretin receptor ligand polypeptide comprising the amino acid sequence of desAmino-Tyr-AEGTFTSDK-(γE-C16)-SKY-LDERAAQDFVQWLLEGGPSSGAPPPS (SEQ ID NO: 121).

One aspect as reported herein is a lipidated incretin receptor ligand polypeptide comprising the amino acid sequence of Ac-d-YALGTFTSDK-(γE-C16)-SKYLDER-AAQDFVQWLLEGGPSSGAPPPS (SEQ ID NO: 122).

One aspect as reported herein is a lipidated incretin receptor ligand polypeptide comprising the amino acid sequence of Ac-d-YAVGTFTSDK-(γE-C16)-SKYLDER-AAQDFVQWLLEGGPSSGAPPPS (SEQ ID NO: 123).

One aspect as reported herein is a lipidated incretin receptor ligand polypeptide comprising the amino acid sequence of Ac-d-HAQGTFTSDK-(γE-C16)-SKYLDER-AAQDFVQWLLEGGPSSGAPPPS (SEQ ID NO: 124).

One aspect as reported herein is a lipidated incretin receptor ligand polypeptide comprising the amino acid sequence of Ac-d-YAQGTFTSDK-(γE-C16)-SKYLDER-AAQDFVQWLLEGGPSSGAPPPS (SEQ ID NO: 125).

One aspect as reported herein is a lipidated incretin receptor ligand polypeptide comprising the amino acid sequence of Y-Aib-EGTFTSDK-(γE-γE-C16)-SIYLD-KQAA-Aib-EFVNWLLAGGPSSGAPPPSC-(S—CH2-CO)-LPETGGSGS (SEQ ID NO: 109).

One aspect as reported herein is a lipidated incretin receptor ligand polypeptide comprising the amino acid sequence of desAminoTyr-AEGTFTSDK-(γE-C16)SKYL-DERAAQDFVQWLLEGGPSSGAPPPSC-(S—CH2-CO)-GGGLPETGGSGS (SEQ ID NO: 110).

One aspect as reported herein is a lipidated incretin receptor ligand polypeptide comprising the amino acid sequence of Ac-d-YALGTFTSDK(γE-C16)SKYLDER-

AAQDFVQWLLEGGPSSGAPPPSC-(S—CH2-CO)-GGGLPETGGSGS (SEQ ID NO: 111).

One aspect as reported herein is a lipidated incretin receptor ligand polypeptide comprising the amino acid sequence of Ac-d-YAVGTFTSDK(γE-C16)SKYLDER-AAQDFVQWLLEGGPSSGAPPPSC-(S—CH2-CO)-GGGLPETGGSGS (SEQ ID NO: 112).

One aspect as reported herein is a lipidated incretin receptor ligand polypeptide comprising the amino acid sequence of Ac-d-HAQGTFTSDK(γE-C16)SKYLDER-AAQDFVQWLLEGGPSSGAPPPSC-(S—CH2-CO)-GGGLPETGGSGS (SEQ ID NO: 113).

One aspect as reported herein is a lipidated incretin receptor ligand polypeptide comprising the amino acid sequence of Ac-d-YAQGTFTSDK(γE-C16)SKYLDER-AAQDFVQWLLEGGPSSGAPPPSC-(S—CH2-CO)-GGGLPETGGSGS (SEQ ID NO: 114).

One aspect as reported herein is a lipidated incretin receptor ligand polypeptide comprising the amino acid sequence of Ac-d-HAQGTFTSDK(γE-C16)SKYLDER-AAQDFVQWLLGGGLPETGGSGS (SEQ ID NO: 115).

One aspect as reported herein is a lipidated incretin receptor ligand polypeptide comprising the amino acid sequence of Ac-d-YALGTFTSDK(γE-C16)SKYLDER-AAQDFVQWLLEGGPSSGAPPPSGGGLPETGGSGS (SEQ ID NO: 116).

One aspect as reported herein is a fusion polypeptide comprising
one, two, three or four incretin receptor ligand polypeptides, and
one human immunoglobulin Fc-region,
wherein at least one of the incretin receptor ligand polypeptides is selected from the group of lipidated incretin receptor ligand polypeptides of SEQ ID NOs: 120 to 125,
wherein the human immunoglobulin Fc-region is selected from group of human immunoglobulin Fc-region of SEQ ID NOs: 42 to 53,
wherein each of the one, two, three or four incretin receptor ligand polypeptides is covalently conjugated independently of each other either directly or via a linker peptide to a terminus of the human immunoglobulin Fc-region, whereby the linker peptide is selected if present from the group comprising (GGS)$_n$, wherein n=1-4 (SEQ ID NOs: 82-84), G$_n$, wherein n=2-6 (SEQ ID NOs: 85-87), (GGGS)$_n$, wherein n=1-6 (SEQ ID NOs: 57-60, 88 and 89), (GGGGS)$_m$, wherein m=1-6 (SEQ ID NOs: 61-64, 90 and 91), and (GGGGGS)$_o$, wherein o=1-6 (SEQ ID NOs: 65-67 and 92-94), and
wherein each of the one, two, three or four incretin receptor ligand polypeptides is covalently conjugated by a peptide bond to a terminus of the human immunoglobulin Fc-region, whereby to each terminus of the human immunoglobulin Fc-region only a single incretin receptor ligand polypeptide is conjugated.

One aspect as reported herein is a fusion polypeptide comprising
one or two incretin receptor ligand polypeptides, and
one human immunoglobulin Fc-region,
wherein at least one of the incretin receptor ligand polypeptides is selected from the group of lipidated incretin receptor ligand polypeptides of SEQ ID NOs: 120 to 125,
wherein the human immunoglobulin Fc-region is selected from group of human immunoglobulin Fc-region of SEQ ID NOs: 42 to 53,
wherein each of the one or two incretin receptor ligand polypeptides is covalently conjugated independently of each other either directly or via a linker peptide to a terminus of the human immunoglobulin Fc-region, whereby the linker peptide is selected if present from the group comprising (GGS)$_n$, wherein n=1-4 (SEQ ID NOs: 82-84), G$_n$, wherein n=2-6 (SEQ ID NOs: 85-87), (GGGS)$_n$, wherein n=1-6 (SEQ ID NOs: 57-60, 88 and 89), (GGGGS)$_m$, wherein m=1-6 (SEQ ID NOs: 61-64, 90 and 91), and (GGGGGS)$_o$, wherein o=1-6 (SEQ ID NOs: 65-67 and 92-94), and
wherein each of the one or two incretin receptor ligand polypeptides is covalently conjugated by a peptide bond to a terminus of the human immunoglobulin Fc-region, whereby to each terminus of the human immunoglobulin Fc-region only a single incretin receptor ligand polypeptide is conjugated.

One aspect as reported herein is a fusion polypeptide comprising
one or two incretin receptor ligand polypeptides, and
one human immunoglobulin Fc-region,
wherein at least one of the incretin receptor ligand polypeptides is selected from the group of lipidated incretin receptor ligand polypeptides of SEQ ID NOs: 120 to 125,
wherein the human immunoglobulin Fc-region comprises i) two amino acid sequences of SEQ ID NO: 49 or ii) one amino acid sequence of SEQ ID NO: 52 and one amino acid sequence of SEQ ID NO: 53,
wherein each of the one or two, three or four incretin receptor ligand polypeptides is covalently conjugated via a linker peptide to an N-terminus of the human immunoglobulin Fc-region, whereby the linker peptide is selected from the group comprising (GGGS)$_4$ (SEQ ID NO: 58), (GGGGS)$_3$ (SEQ ID NO: 62), and (GGGGGS)$_o$, wherein o=2-3 (SEQ ID NOs: 65-66), and
wherein each of the one or two incretin receptor ligand polypeptides is covalently conjugated by a peptide bond to a terminus of the human immunoglobulin Fc-region, whereby to each terminus of the human immunoglobulin Fc-region only a single incretin receptor ligand polypeptide is conjugated.

One aspect as reported herein is a pharmaceutical composition comprising a fusion polypeptide as reported herein.

One aspect as reported herein is the use of a fusion polypeptide as reported herein as a medicament.

One aspect as reported herein is the use of a fusion polypeptide as reported herein for the manufacture of a medicament for the treatment of a disease, wherein it is favorable that the effector function of the fusion polypeptide comprising a variant Fc-region of a wild-type human IgG Fc-region is reduced compared to the effector function induced by a fusion polypeptide comprising a wild-type human IgG Fc-region.

One aspect as reported herein is the use of a fusion polypeptide as reported herein comprising a variant Fc-region of a wild-type human IgG Fc-region, wherein Pro329 of the wild-type human IgG Fc-region is substituted with glycine, wherein the residues are numbered according to the EU index of Kabat, wherein the fusion polypeptide exhibits a reduced affinity to the human FcγRIIIA and FcγRIIA for down-modulation of ADCC by at least 20% of the ADCC induced by a fusion polypeptide comprising the wild-type human IgG Fc-region, and/or for down-modulation of ADCP.

In one embodiment the disease is type-2 diabetes
In one embodiment the disease is obesity.
In one embodiment the disease is insulin resistance.
In one embodiment the disease is type-1 diabetes.
In one embodiment the disease is osteoporosis.
In one embodiment the disease is steatohepatitis.

In one embodiment the disease is non-alcoholic fatty liver disease (NAFLD).

In one embodiment the disease is metabolic syndrome.

In one embodiment the fusion polypeptide as reported herein is administered in combination with a further type-2 diabetes drug.

In one embodiment the further type-2 diabetes drug is insulin.

One aspect as reported herein is a polypeptide comprising the amino acid sequence of an incretin receptor ligand polypeptide and LPXTG (SEQ ID NO: 75), wherein X is any amino acid.

In one embodiment X is an acidic amino acid.

In one embodiment the acidic amino acid is Glu.

In one embodiment the polypeptide comprises Gly-Gly or Gly-Gly-Ser or Gly-Gly-Gly, Gly-Gly-Gly-Ser (SEQ ID NO: 88), Gly-Gly-Gly-Gly (SEQ ID NO: 85), or Gly-Gly-Gly-Gly-Ser (SEQ ID NO: 90) C-terminally to LPETG (SEQ ID NO: 74).

In one embodiment the polypeptide comprises (GGGS)n, wherein n=1-6 (SEQ ID NOs: 57-60, 88 and 89), (GGGGS)m, wherein m=1-6 (SEQ ID NOs: 61-64, 90 and 91), or (GGGGGS)o, wherein o=1-6 (SEQ ID NOs: 65-67 and 92-94).

In one embodiment the polypeptide comprises any one of SEQ ID NOs: 57-67.

In one embodiment the polypeptide comprises Gly or Gly-Gly N-terminally to LPXTG (SEQ ID NO: 75).

One aspect as reported herein is the use of the polypeptide as reported herein in the manufacture of a medicament for treating a disease.

In one embodiment the manufacture of the medicament comprises use of sortase A.

DETAILED DESCRIPTION OF EMBODIMENTS OF THE INVENTION

I. Definitions

Figure 1:
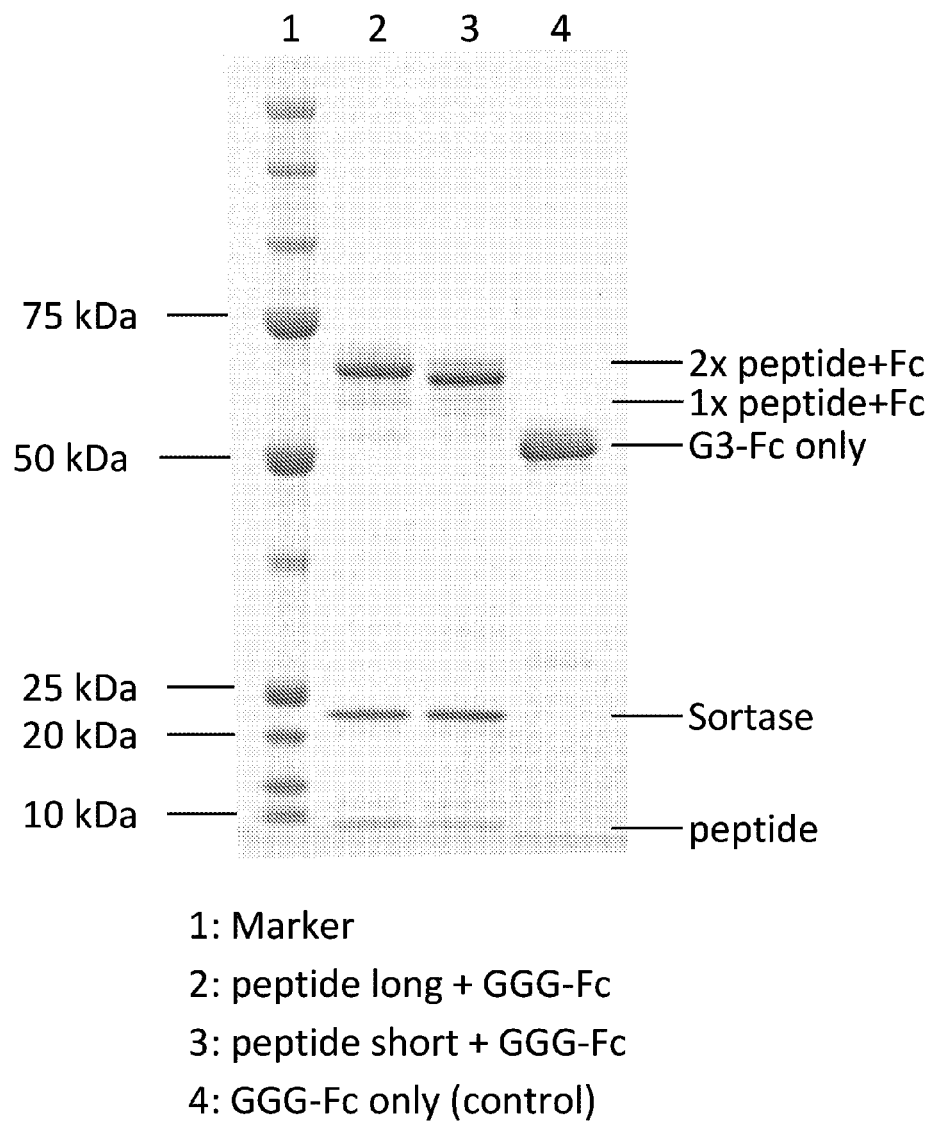
FIG. 1 SDS-PAGE analysis of sortase-mediated transpeptidation reactions.

In the present specification and claims the numbering of the residues in an immunoglobulin heavy chain Fc-region is that of the EU index of Kabat (Kabat, E. A., et al., Sequences of Proteins of Immunological Interest, 5th ed., Public Health Service, National Institutes of Health, Bethesda, Md. (1991), NIH Publication 91-3242, expressly incorporated herein by reference). The term "EU index of Kabat" denotes the residue numbering of the human IgG1 EU antibody.

The term "affinity" denotes the strength of the sum total of non-covalent interactions between a single binding site of a molecule (e.g., an antibody) and its binding partner (e.g., an antigen or an Fc receptor). Unless indicated otherwise, as used herein, "binding affinity" refers to intrinsic binding affinity which reflects a 1:1 interaction between members of a binding pair (e.g., antibody/Fc receptor or antibody and antigen). The affinity of a molecule X for its partner Y can generally be represented by the dissociation constant ($K_D$). Affinity can be measured by common methods known in the art, including those described herein.

The term "alteration" denotes the mutation, addition, or deletion of one or more amino acid residues in a parent amino acid sequence, e.g. of an antibody or fusion polypeptide comprising at least an FcRn binding portion of an Fc-region, to obtain a variant antibody or fusion polypeptide.

The term "amino acid mutation" denotes a modification in the amino acid sequence of a parent amino acid sequence. Exemplary modifications include amino acid substitutions, insertions, and/or deletions. In one embodiment the amino acid mutation is a substitution. The term "amino acid mutations at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, aib and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "amino acid insertion" denotes the incorporation of at least one additional amino acid residue into a predetermined parent amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as defined above.

The term "amino acid deletion" denotes the removal of at least one amino acid residue at a predetermined position in an amino acid sequence.

The term "antibody variant" denotes a variant of a parent antibody (e.g. a wild-type antibody), characterized in that at least one alteration in the amino acid sequence relative to the parent amino acid sequence is present in the antibody variant amino acid sequence, e.g. introduced by mutation of one or more amino acid residues in the parent antibody.

Within this application whenever an amino acid alteration is mentioned it is a deliberated amino acid alteration and not a random amino acid modification.

The term "antibody-dependent cell-mediated cytotoxicity", short "ADCC", denotes a cell-mediated reaction in which non-antigen specific cytotoxic cells that express FcRs (e.g. natural killer cells (NK cells), neutrophils, and macrophages) recognize a target cell by binding to immunoglobulin Fc-region and subsequently cause lysis of the target cell. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol. 9 (1991) 457-492.

The term "antibody-dependent cellular phagocytosis", short "ADCP", denotes a process by which antibody-coated cells are internalized, either in whole or in part, by phagocytic immune cells (e.g. macrophages, neutrophils, or dendritic cells) that bind to an immunoglobulin Fc-region.

The term "binding to an Fc receptor" denotes the binding of an Fc-region to an Fc receptor in, for example, a BIAcore® assay (Pharmacia Biosensor AB, Uppsala, Sweden).

In the BIAcore® assay the Fc receptor is bound to a surface and binding of the analyte, e.g. an Fc-region comprising fusion polypeptide or an antibody, is measured by surface plasmon resonance (SPR). The affinity of the binding is defined by the terms $k_a$ (association constant: rate constant for the association of the Fc-region fusion polypeptide to form an Fc-region/Fc receptor complex), $k_d$ (dissociation constant; rate constant for the dissociation of the Fc-region fusion polypeptide from an Fc-region/Fc receptor complex), and $K_D$ ($k_d/k_a$). Alternatively, the binding signal of a SPR sensorgram can be compared directly to the response signal of a reference, with respect to the resonance signal height and the dissociation behaviors.

The term "C1q" denotes a polypeptide that includes a binding site for the Fc-region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "incretin receptor ligand polypeptide" denotes a naturally occurring or synthetic polypeptide that binds to the glucagon receptor (GCGR), or/and the glucagon-like-peptide-I (GLP-1) receptor (GLP-1R), or/and glucose-dependent insulinotropic peptide (GIP) receptor (GIPR), i.e. a molecule that has agonist activity for at least one of these receptors.

In one embodiment the incretin receptor ligand polypeptide binds to the glucose-dependent insulinotropic peptide receptor. In one preferred embodiment the incretin receptor ligand polypeptide binds to the glucose-dependent insulinotropic peptide receptor and to the glucagon-like-peptide-I receptor. In one embodiment the incretin receptor ligand polypeptide binds to the glucose-dependent insulinotropic peptide receptor and to the glucagon-like-peptide-I receptor and to the glucagon receptor.

When blood glucose begins to fall, glucagon, a hormone produced by the pancreas, signals the liver to break down glycogen and release glucose, causing blood glucose levels to rise toward a normal level. GLP-I has different biological activities compared to glucagon. Its actions include stimulation of insulin synthesis and secretion, inhibition of glucagon secretion, and inhibition of food intake. GLP-I has been shown to reduce hyperglycemia (elevated glucose levels) in diabetics. Exendin-4, a peptide from lizard venom that shares about 50% amino acid sequence identity with GLP-I, activates the GLP-I receptor and likewise has been shown to reduce hyperglycemia in diabetics. Glucose-dependent insulinotropic peptide (GIP) is a 42-amino acid gastrointestinal regulatory peptide that stimulates insulin secretion from pancreatic beta cells in the presence of glucose. It is derived by proteolytic processing from a 133-amino acid precursor, preproGIP.

The fusion polypeptide as reported herein comprises an incretin receptor ligand that has modifications to the native glucagon sequence that exhibits potent glucagon activity equivalent to or better than the activity of native glucagon, potent GIP activity equivalent to or better than the activity of native GIP, and/or potent GLP-I activity equivalent to or better than the activity of native GLP-I.

The effects of the fusion polypeptide reported herein include glucose homeostasis, insulin secretion, gastric emptying, intestinal growth, regulation of food intake. Peptides having both GIP activity and GLP-I activity are particularly advantageous for inducing weight loss or preventing weight gain, as well as for treating hyperglycemia, including diabetes.

Incretin receptor ligand polypeptides include, but are not limited to, GLP-1, exendin-3, exendin-4, and precursors, derivatives, or fragments thereof. Exemplary incretin receptor ligand polypeptides are reported in U.S. Pat. No. 5,574,008, U.S. Pat. No. 5,424,286, U.S. Pat. No. 6,514,500, U.S. Pat. No. 6,821,949, U.S. Pat. No. 6,887,849, U.S. Pat. No. 6,849,714, U.S. Pat. No. 6,329,336, U.S. Pat. No. 6,924,264, WO 2003/103572, U.S. Pat. No. 6,593,295, WO 2011/109784, WO 2010/011439, U.S. Pat. No. 6,329,336 and U.S. Pat. No. 7,153,825.

The term "CH2 domain" denotes the part of an antibody heavy chain polypeptide that extends approximately from EU position 231 to EU position 340 (EU numbering system according to Kabat). In one embodiment a CH2 domain has the amino acid sequence of APELLGGPSVFLFPPKP-KDTLMISRTPEVTCVWDVSHEDPEVKFN-WYVDGVEVHNAKT KPREEQESTYRWSVLTVLHQD-WLNGKEYKCKVSNKALPAPIEKTISKAK (SEQ ID NO: 40). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206.

The term "CH3 domain" denotes the part of an antibody heavy chain polypeptide that extends approximately from EU position 341 to EU position 446. In one embodiment the CH3 domain has the amino acid sequence of GQPREPQVYTLPPSRDELTKNQVSLTCLVKGFYPS-DIAVEWESNGQPENNYKTTPPVLD SDGSFFLYSKLT-VDKSRWQQGNVFSCSVMHEALHNHYTQKSLSLSPG (SEQ ID NO: 41).

The term "class" of an antibody denotes the type of constant domain or constant region possessed by its heavy chain. There are five major classes of antibodies in humans: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "complement-dependent cytotoxicity", short "CDC", denotes a mechanism for inducing cell death in which an Fc-region of a target-bound Fc-region fusion polypeptide activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC or ADCP by binding complement receptors (e.g., CR3) on leukocytes.

The term "effector function" denotes those biological activities attributable to the Fc-region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis (ADCP); down regulation of cell surface receptors (e.g. B-cell receptor); and B-cell activation. Such function can be triggered by, for example, binding of an Fc-region to an Fc receptor on an immune cell with phagocytic or lytic activity, or by binding of an Fc-region to components of the complement system.

The term "reduced effector function" denotes a reduction of a specific effector function associated with a molecule, like for example ADCC or CDC, in comparison to a control molecule (for example a polypeptide with a wild-type Fc-region) by at least 20%. The term "strongly reduced effector function" denotes a reduction of a specific effector function associated with a molecule, like for example ADCC or CDC, in comparison to a control molecule by at least 50%.

The term "effective amount" of an agent, e.g., a pharmaceutical formulation, denotes an amount effective, at dosages and for periods of time necessary, to achieve the desired therapeutic or prophylactic result.

The term "Fc-region" denotes the C-terminal region of an immunoglobulin. The Fc-region is a dimeric molecule comprising disulfide-linked antibody heavy chain fragments (Fc-region polypeptide chains), optionally comprising one, two, three or more disulfide linkages. An Fc-region can be generated by papain digestion, or IdeS digestion, or trypsin digestion of an intact (full length) antibody or can be produced recombinantly.

The Fc-region obtainable from a full length antibody or immunoglobulin comprises residues 226 (Cys) to the C-terminus of the full length heavy chain and, thus, comprises a part of the hinge region and two or three constant domains, i.e. a CH2 domain, a CH3 domain, and optionally a CH4 domain. It is known from U.S. Pat. No. 5,648,260 and U.S. Pat. No. 5,624,821 that the modification of defined amino acid residues in the Fc-region results in phenotypic effects.

The formation of the dimeric Fc-region comprising two identical or non-identical antibody heavy chain fragments is mediated by the non-covalent dimerization of the comprised CH3 domains (for involved amino acid residues see e.g. Dall'Acqua, Biochem. 37 (1998) 9266-9273). The Fc-region is covalently stabilized by the formation of disulfide bonds in the hinge region (see e.g. Huber, et al., Nature 264 (1976) 415-420; Thies, et al., J. Mol. Biol. 293 (1999) 67-79). The introduction of amino acid residue changes within the CH3 domain in order to disrupt the dimerization of CH3-CH3 domain interactions do not adversely affect the neonatal Fc receptor (FcRn) binding due to the location of the CH3-CH3-domain dimerization involved residues are located on the inner interface of the CH3 domain, whereas the residues involved in Fc-region-FcRn interaction are located on the outside of the CH2-CH3 domain.

The residues associated with effector functions of an Fc-region are located in the hinge region, the CH2, and/or the CH3 domain as determined for a full length antibody molecule. The Fc-region associated/mediated functions are:
(i) antibody-dependent cellular cytotoxicity (ADCC),
(ii) complement (C1q) binding, activation and complement-dependent cytotoxicity (CDC),
(iii) phagocytosis/clearance of antigen-antibody complexes,
(iv) cytokine release in some instances, and
(v) half-life/clearance rate of antibody and antigen-antibody complexes.

The Fc-region associated effector functions are initiated by the interaction of the Fc-region with effector function specific molecules or receptors. Mostly antibodies of the IgG1 isotype can effect receptor activation, whereas antibodies of the IgG2 and IgG4 isotypes do not have effector function or have limited effector function.

The effector function eliciting receptors are the Fc receptor types (and sub-types) FcγRI, FcγRII and FcγRIII The effector functions associated with an IgG1 isotype can be reduced by introducing specific amino acid changes in the lower hinge region, such as L234A and/or L235A, which are involved in FcγR and C1q binding. Also certain amino acid residues, especially located in the CH2 and/or CH3 domain, are associated with the circulating half-life of an antibody molecule or an Fc-region fusion polypeptide in the blood stream. The circulatory half-life is determined by the binding of the Fc-region to the neonatal Fc receptor (FcRn).

The sialyl residues present on the Fc-region glycostructure are involved in anti-inflammatory mediated activity of the Fc-region (see e.g. Anthony, R. M., et al. Science 320 (2008) 373-376).

The numbering of the amino acid residues in the constant region of an antibody is made according to the EU index of Kabat (Kabat, E. A., et al., Sequences of Proteins of Immunological Interest, 5th ed., Public Health Service, National Institutes of Health, Bethesda, Md. (1991), NIH Publication 91 3242).

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from about Cys226, or from about Pro230, to the carboxyl-terminus of the heavy chain. However, the C-terminal lysine (Lys447) of the Fc-region may or may not be present.

The term "variant Fc-region" denotes an amino acid sequence which differs from that of a "parent", "native" or "wild-type" Fc-region amino acid sequence by virtue of at least one "amino acid alteration/mutation". In one embodiment the variant Fc-region has at least one amino acid mutation compared to a native Fc-region or to the Fc-region of a parent polypeptide, e.g. from about one to about ten amino acid mutations, and in one embodiment from about one to about five amino acid mutations in a native Fc-region or in the Fc-region of the parent polypeptide. In one embodiment the (variant) Fc-region has at least about 80% homology with a wild-type Fc-region and/or with an Fc-region of a parent polypeptide, and in one embodiment the variant Fc-region has least about 90% homology, in one embodiment the variant Fc-region has at least about 95% homology.

The variant Fc-region as reported herein is defined by the amino acid alterations that are contained. Thus, for example, the term P329G denotes a variant Fc-region with the mutation of proline to glycine at amino acid position 329 relative to the parent (wild-type) Fc-region. The identity of the wild-type amino acid may be unspecified, in which case the aforementioned variant is referred to as 329G. For all positions discussed in the present invention, numbering is according to the EU index. The EU index or EU index as in Kabat or EU numbering scheme refers to the numbering of the EU antibody (Edelman, et al., Proc. Natl. Acad. Sci. USA 63 (1969) 78-85). The alteration can be an addition, deletion, or mutation. The term "mutation" denotes a change to naturally occurring amino acids as well as a change to non-naturally occurring amino acids, see e.g. U.S. Pat. No. 6,586,207, WO 98/48032, WO 03/073238, US 2004/0214988, WO 2005/35727, WO 2005/74524, Chin, J. W., et al., J. Am. Chem. Soc. 124 (2002) 9026-9027; Chin, J. W. and Schultz, P. G., ChemBioChem 11 (2002) 1135-1137; Chin, J. W., et al., PICAS United States of America 99 (2002) 11020-11024; and, Wang, L. and Schultz, P. G., Chem. (2002) 1-10.

A polypeptide chain of a wild-type human Fc-region of the IgG1 isotype has the following amino acid sequence:

(SEQ ID NO: 42)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A polypeptide chain of a variant human Fc-region of the IgG1 isotype with the mutations L234A, L235A has the following amino acid sequence:

(SEQ ID NO: 43)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A polypeptide chain of a variant human Fc-region of the IgG1 isotype with a hole mutation has the following amino acid sequence:

(SEQ ID NO: 44)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A polypeptide chain of a variant human Fc-region of the IgG1 isotype with a knob mutation has the following amino acid sequence:

(SEQ ID NO: 45)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A polypeptide chain of a variant human Fc-region of the IgG1 isotype with a L234A, L235A and hole mutation has the following amino acid sequence:

(SEQ ID NO: 46)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A polypeptide chain of a variant human Fc-region of the IgG1 isotype with a L234A, L235A and knob mutation has the following amino acid sequence:

(SEQ ID NO: 47)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A polypeptide chain of a variant human Fc-region of the IgG1 isotype with a P329G mutation has the following amino acid sequence:

(SEQ ID NO: 48)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A polypeptide chain of a variant human Fc-region of the IgG1 isotype with a L234A, L235A and P329G mutation has the following amino acid sequence:

(SEQ ID NO: 49)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A polypeptide chain of a variant human Fc-region of the IgG1 isotype with a P329G and hole mutation has the following amino acid sequence:

(SEQ ID NO: 50)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A polypeptide chain of a variant human Fc-region of the IgG1 isotype with a P329G and knob mutation has the following amino acid sequence:

(SEQ ID NO: 51)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A polypeptide chain of a variant human Fc-region of the IgG1 isotype with a L234A, L235A, P329G and hole mutation has the following amino acid sequence:

(SEQ ID NO: 52)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A polypeptide chain of a variant human Fc-region of the IgG1 isotype with a L234A, L235A, P329G and knob mutation has the following amino acid sequence:

(SEQ ID NO: 53)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A polypeptide chain of a wild-type human Fc-region of the IgG4 isotype has the following amino acid sequence:

(SEQ ID NO: 54)
ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.

A polypeptide chain of a variant human Fc-region of the IgG4 isotype with a S228P and L235E mutation has the following amino acid sequence:

(SEQ ID NO: 55)
ESKYGPPCPPCPAPEFEGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.

A polypeptide chain of a variant human Fc-region of the IgG4 isotype with a S228P, L235E and P329G mutation has the following amino acid sequence:

(SEQ ID NO: 56)
ESKYGPPCPPCPAPEFEGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLGSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.

The term "Fc receptor", short "FcR", denotes a receptor that binds to an Fc-region. In one embodiment the FcR is a native sequence human FcR. Moreover, in one embodiment the FcR is an FcR which binds an IgG antibody (an Fc gamma receptor) and includes receptors of the FcγRI, FcγRII, and FcγRIII subclasses, including allelic variants and alternatively spliced forms thereof. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see e.g. Daëron, M., Annu. Rev. Immunol. 15 (1997) 203-234). FcRs are reviewed in Ravetch and Kinet, Annu. Rev. Immunol 9 (1991) 457-492, Capel, et al., Immunomethods 4 (1994) 25-34, de Haas, et al., J. Lab. Clin. Med. 126 (1995) 330-341. Other FcRs, including those to be identified in the future, are encompassed by the term "FcR" herein. The term also includes the neonatal receptor, FcRn, which is responsible for the transfer of maternal IgGs to the fetus (see e.g. Guyer, et al., J. Immunol. 117 (1976) 587; Kim, et al., J. Immunol. 24 (1994) 249).

The term "IgG Fc ligand" denotes a molecule, in one embodiment a polypeptide, from any organism that binds to the Fc-region of an IgG antibody to form an Fc-region/Fc ligand complex. Fc ligands include but are not limited to FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (see e.g. Davis, et al., Immunological Reviews 190 (2002) 123-136). Fc ligands may include undiscovered molecules that bind Fc. In one embodiment IgG Fc ligands are the FcRn and Fc gamma receptors The term "Fc gamma receptor", short "FcγR", denotes any member of the family of proteins that bind the IgG antibody Fc-region and is encoded by an FcγR gene. In humans this family includes but is not limited to FcγRI (CD64), including isoforms FcγRIA, FcγRIB, and FcγRIC, FcγRII (CD32), including isoforms FcγRIIA (including allotypes H131 and R131), FcγRIIB (including FcγRIIB-1 and FcγRIIB-2), and FcγRIIC, and FcγRIII (CD16), including isoforms FcγRIIIA (including allotypes V158 and F158) and FcγRIIIB (including allotypes FcγRIIIB-NA1 and FcγRIIIB-NA2) (see e.g. Jefferis, et al., Immunol. Lett. 82 (2002) 57-65), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes. The Fc-region-FcγR interaction involved amino acid residues are 234-239 (lower hinge region), 265-269 (B/C loop), 297-299 (D/E loop), and 327-332 (F/G) loop (Sondermann, et al., Nature 406 (2000) 267-273). Amino acid mutations that result in a decreased binding/affinity for the FcγRI, FcγRIIA, FcγRIIB, and/or FcγRIIIA include N297A (concomitantly with a decreased immunogenicity and prolonged half-life binding/affinity) (Routledge, et al., Transplantation 60 (1995) 847; Friend, et al., Transplantation 68 (1999) 1632; Shields, et al., J. Biol. Chem. 276 (1995) 6591-6604), residues 233-236 (Ward and Ghetie, Ther. Immunol. 2 (1995) 77; Armour, et al., Eur. J. Immunol. 29 (1999) 2613-2624). Some exemplary amino acid substitutions are described in U.S. Pat. No. 7,355,008 and U.S. Pat. No. 7,381,408.

The term "neonatal Fc Receptor", short "FcRn", denotes a protein that binds the IgG antibody Fc-region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. The interacting amino acid residues of the Fc-region with the FcRn are near the junction of the CH2 and CH3 domains. The Fc-region-FcRn contact residues are all within a single IgG heavy chain. The involved amino acid residues are 248, 250-257, 272, 285, 288, 290-291, 308-311, and 314 (all in the CH2 domain) and amino acid residues 385-387, 428, and 433-436 (all in the CH3 domain). Amino acid mutations that result in an increased binding/affinity for the FcRn include T256A, T307A, E380A, and N434A (Shields, et al., J. Biol. Chem. 276 (2001) 6591-6604).

The terms "wild-type polypeptide" or "parent polypeptide" denote a starting polypeptide, either unmodified (wild-type polypeptide) or already containing at least one alteration distinguishing it from the wild-type (parent polypeptide), which is subsequently altered to generate a variant. The term "wild-type polypeptide" denotes the polypeptide itself, compositions that comprise the polypeptide, or the nucleic acid sequence that encodes it. Accordingly, the term "wild-type Fc-region polypeptide" denotes an Fc-region fusion polypeptide comprising a naturally occurring Fc-region which is altered to generate a variant.

The term "full length antibody" denotes an antibody having that has a structure and amino acid sequence substantially identical to a native antibody structure as well as polypeptides that comprise the Fc-region as reported herein.

The term "hinge region" denotes the part of an antibody heavy chain polypeptide that joins the CH1 domain and the CH2 domain, e. g. from about position 216 to position about 230 according to the EU number system of Kabat. The hinge regions of other IgG isotypes can be determined by aligning with the hinge-region cysteine residues of the IgG1 isotype sequence.

The hinge region is normally a dimeric molecule consisting of two polypeptides with identical amino acid sequence. The hinge region generally comprises about 25 amino acid residues and is flexible allowing the antigen binding regions to move independently. The hinge region can be subdivided into three domains: the upper, the middle, and the lower hinge domain (see e.g. Roux, et al., J. Immunol. 161 (1998) 4083).

The term "lower hinge region" of an Fc-region denotes the stretch of amino acid residues immediately C-terminal to the hinge region, i.e. residues 233 to 239 of the Fc-region according to the EU numbering of Kabat.

The term "wild-type Fc-region" denotes an amino acid sequence identical to the amino acid sequence of an Fc-region found in nature. Wild-type human Fc-regions include a native human IgG1 Fc-region (non-A and A allotypes), native human IgG2 Fc-region, native human IgG3 Fc-region, and native human IgG4 Fc-region as well as naturally occurring variants thereof.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "position" denotes the location of an amino acid residue in the amino acid sequence of a polypeptide. Positions may be numbered sequentially, or according to an established format, for example the EU index of Kabat for antibody numbering.

The term "treatment" (and grammatical variations thereof such as "treat" or "treating") denotes a clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variant" denotes a polypeptide which has an amino acid sequence that differs from the amino acid sequence of a parent polypeptide. Typically such molecules have one or more alterations, insertions, or deletions. In one embodiment the variant amino acid sequence has less than 100% sequence identity with the parent amino acid sequence. In one embodiment the variant amino acid sequence has an amino acid sequence from about 75% to less than 100% amino acid sequence identity with the amino acid sequence of the parent polypeptide. In one embodiment the variant amino acid sequence has from about 80% to less than 100%, in one embodiment from about 85% to less than 100%, in one embodiment from about 90% to less than 100%, and in one embodiment from about 95% to less than 100% amino acid sequence identity with the amino acid sequence of the parent polypeptide.

The term "altered" FcR binding affinity or ADCC activity denotes a polypeptide that has either enhanced or diminished FcR binding activity and/or ADCC activity compared to a parent polypeptide (e.g. a polypeptide comprising a wild-type Fc-region). The variant polypeptide which "has increased binding" to an FcR binds at least one FcR with lower dissociation constant (i.e. better/higher affinity) than the parent or wild-type polypeptide. The polypeptide variant which "has decreased binding" to an FcR, binds at least one FcR with higher dissociation constant (i.e. worse/lower affinity) than the parent or a wild-type polypeptide. Such variants which display decreased binding to an FcR may possess little or no appreciable binding to an FcR, e.g., 0-20% binding to the FcR compared to a wild-type or parent IgG Fc-region, e.g. as determined in the Examples described herein.

The polypeptide which binds an FcR with "reduced affinity" in comparison with a parent or wild-type polypeptide, is a polypeptide which binds any one or more of the above identified FcRs with (substantially) reduced binding affinity compared to the parent polypeptide, when the amounts of polypeptide variant and parent polypeptide in the binding assay are (essentially) about the same. For example, the polypeptide variant with reduced FcR binding affinity may display from about 1.15 fold to about 100 fold, e.g. from about 1.2 fold to about 50 fold reduction in FcR binding affinity compared to the parent polypeptide, where FcR binding affinity is determined, for example, as disclosed in the examples disclosed herein.

The polypeptide comprising a variant Fc-region which "mediates antibody-dependent cell-mediated cytotoxicity (ADCC) in the presence of human effector cells less effectively" than a parent polypeptide is one which in vitro or in vivo is (substantially) less effective at mediating ADCC, when the amounts of variant polypeptide and parent polypeptide used in the assay are (essentially) about the same.

Generally, such variants will be identified using the in vitro ADCC assay as disclosed herein, but other assays or methods for determining ADCC activity, e.g. in an animal model etc., are contemplated. In one embodiment the variant is from about 1.5 fold to about 100 fold, e.g. from about two fold to about fifty fold, less effective at mediating ADCC than the parent, e.g. in the in vitro assay disclosed herein.

The term "receptor" denotes a polypeptide capable of binding at least one ligand. In one embodiment the receptor is a cell-surface receptor having an extracellular ligand-binding domain and, optionally, other domains (e.g. transmembrane domain, intracellular domain and/or membrane anchor). The receptor to be evaluated in the assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase.

The term "receptor binding domain" denotes any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

II. Incretin Receptor Ligand Polypeptides and Fc-Region Fusion Polypeptide Containing the Same Herein is reported an Fc-region fusion polypeptide comprising one to four incretin receptor ligand polypeptides and a variant Fc-region.

It has been found that lipidation can increase the biological activity of incretin receptor ligand polypeptides. Thus, these peptides are aspects of the current invention. The effect on receptor binding of lipidation of different compounds is shown in the following Table.

TABLE 1

| compound | human GCG-R | | human GIP-R | | human GLP-R | |
|---|---|---|---|---|---|---|
| | EC50 [nM] | % max GCG | EC50 [nM] | % max GIP | EC50 [nM] | % max GLP-1 |
| human glucagon (GCG) | 0.004 | 100 | — | — | — | — |
| human GIP | — | — | 0.1 | 100 | — | — |
| human GLP-1 | — | — | — | — | 0.020 | 100 |
| PEGylated dual GIP/GLP antagonist reference from WO 2010/011439 | >600 | 2.3 | 9.3 | 102.0 | 4.9 | 100.6 |
| Dulaglutide | >600 | 1.6 | >600 | 13.8 | 0.129 | 98.2 |
| peptide-long24A-G3Fc (LALAPG) | n.d. | n.d. | 3.782 | 75.4 | 0.623 | 92.4 |
| compound 9 (lipidated incretin receptor ligand polypeptide) | 8.86 | 109.0 | 0.031 | 90.7 | 0.012 | 99.9 |
| compound 10 (lipidated incretin receptor ligand polypeptide) | 9.13 | 100.2 | 0.029 | 86.7 | 0.010 | 96.7 |
| compound 42 (Fc-region and compound 9) | 4.10 | 49.9 | 0.021 | 86.5 | 0.011 | 96.5 |
| compound 45 (Fc-region and compound 10) | 4.93 | 54.8 | 0.018 | 92.0 | 0.008 | 96.8 |

It can be seen that by lipidation (independently of conjugation to an Fc-region) the biological activity (such as e.g. the EC50 value) can be improved. The lipidated incretin receptor ligand polypeptides have a biological activity similar to the naturally occurring receptor ligands GLP and GIP-1 on human GLP receptor and human GIP-1 receptor, respectively.

Thus, it has further been found that the combination of lipidation and Fc-region fusion does not impart the biological activity of incretin receptor ligand polypeptides. Comparative results are shown in the following Table.

| compound | human GCG-R EC50 [nM] | human GCG-R % max GCG | human GIP-R EC50 [nM] | human GIP-R % max GIP | human GLP-R EC50 [nM] | human GLP-R % max GLP-1 |
|---|---|---|---|---|---|---|
| compound 9 | 8.86 | 109 | 0.01 | 100 | 0.03 | 91 |
| compound 42 (=compound 9 + Fc-region) | 4.1 | 50 | 0.02 | 87 | 0.01 | 97 |
| compound 10 | 8.8 | 98 | 0.01 | 97 | 0.02 | 96 |

But, it has now been found that although the incretin receptor ligand polypeptide is lipidated (and thus complexed with a large polypeptide) and fused to a human immunoglobulin Fc-region that the biological activity is at least comparable or even increased to the not-lipidated, not-Fc-region fused incretin receptor ligand polypeptide. Additionally exposure and the in vivo half-life is increased compared to non-lipidated incretin receptor ligand polypeptide Fc-region fusion polypeptides and to PEGylated incretin receptor ligand polypeptide. The respective data is shown in the following table.

| PK parameter* | units | type of construct lipidated Fc-fusion as reported herein | reference peptide 1 Fc-fusion, non-lipidated | reference peptide 2 Fc-fusion, non-lipidated | reference peptide 3 Fc-fusion, non-lipidated | reference peptide 4 Fc-fusion, non-lipidated | reference peptide 5 PEGylated non-lipidated |
|---|---|---|---|---|---|---|---|
| T½ (terminal) | h | 87 | 24 | 22 | 23 | 26 | 41 |
| $T_{max}$ | h | 48 | 24 | 24 | 8 | 24 | 24 |
| $C_{max}$ | nM | 182 | 18.6 | 26.3 | 56 | 26.3 | 153 |
| $C_{max}$/Dose | nM/(nmol/kg) | 9.11 | 0.93 | 1.32 | 2.79 | 1.32 | 7.68 |
| AUCInf | h*nmol/mL | 29.6 | 0.81 | 1.13 | 2.91 | 1.25 | 14.2 |
| $AUC_{0-24\,h}$ | h*nmol/mL | 2.20 | 0.38 | 0.54 | 1.01 | 0.54 | 2.34 |
| $AUC_{0-168\,h}$ | h*nmol/mL | 20.7 | 0.80 | 1.13 | 2.89 | 1.23 | 13.1 |

-continued

| compound | human GCG-R EC50 [nM] | human GCG-R % max GCG | human GIP-R EC50 [nM] | human GIP-R % max GIP | human GLP-R EC50 [nM] | human GLP-R % max GLP-1 |
|---|---|---|---|---|---|---|
| compound 45 (=compound 10 + Fc-region) | 3.9 | 66 | 0.01 | 100 | 0.01 | 100 |
| compound 11 | 43.21 | 28 | 0.02 | 83 | 0.39 | 67 |
| compound 74 (=compound 11 + Fc-region) | 63.2 | 31 | 0.03 | 83 | 0.62 | 72 |
| compound 12 | 2.86 | 100 | 0.04 | 90 | 0.14 | 94 |
| compound 80 (=compound 12 + Fc-region) | 2.38 | 79 | 0.03 | 78 | 0.13 | 99 |
| compound 13 | 1.80 | 99 | 0.05 | 91 | 0.21 | 73 |
| compound 77 (=compound 13 + Fc-region) | 0.77 | 91 | 0.02 | 84 | 0.08 | 77 |
| compound 14 | n.d. | n.d. | n.d. | n.d. | n.d. | n.d. |
| compound 808 (=compound 14 + Fc-region) | 0.42 | 95 | 0.16 | 87 | 2.45 | 71 |
| compound 15 | n.d. | n.d. | n.d. | n.d. | n.d. | n.d. |
| compound 809 (=compound 15 + Fc-region) | 0.20 | 93 | 0.16 | 87 | 6.89 | 55 |

Without being bound by this theory it is assumed that the lipidated incretin receptor polypeptide is after application in vivo (or also in vitro if the respective binding partner is present) complexed by an endogenous polypeptide, e.g. such as human serum albumin. As the incretin receptor ligand polypeptide is small compared to the size of the complexing endogenous polypeptide it is expected that the complexation reduced the biological activity of the incretin receptor ligand polypeptide as the accessibility thereof will be reduced. Additionally if the incretin receptor ligand polypeptide is further fused to a human immunoglobulin Fc-region (or variant thereof) this becomes even more problematic.

Figure 6:
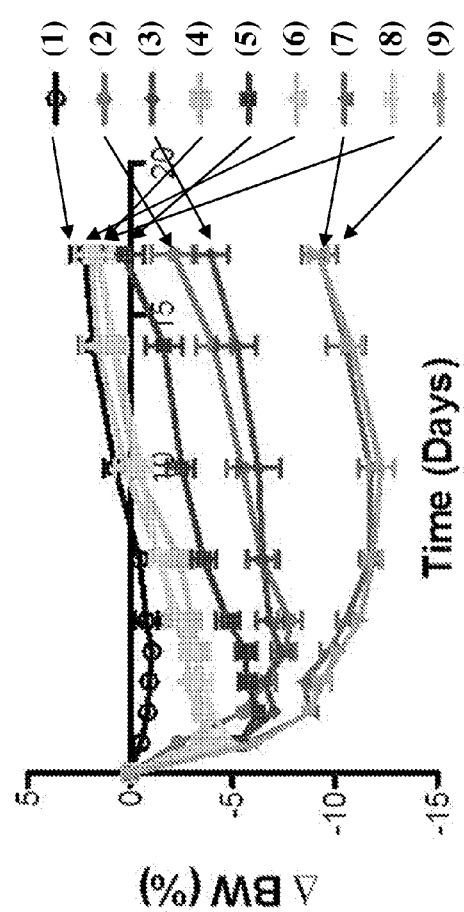
FIG. 6 Change in body weight (BW) after application of different compounds. Open circle: vehicle control (1); closed big circles: peptide-long24C (10 nmol) (2); closed small circles: peptide-long24N-G3Fc (10 nmol) (3); big filled squares: Dulaglutide (1 nmol) (4); small filled squares: Dulaglutide (10 nmol) (5); big filled triangles: compound 42 (1 nmol) (6); small filled triangles: compound 42 (10 nmol) (7); big filled upside-down triangle: compound 45 (1 nmol) (8); small filled upside-down triangle: compound 45 (10 nmol) (9).
Figure 7:
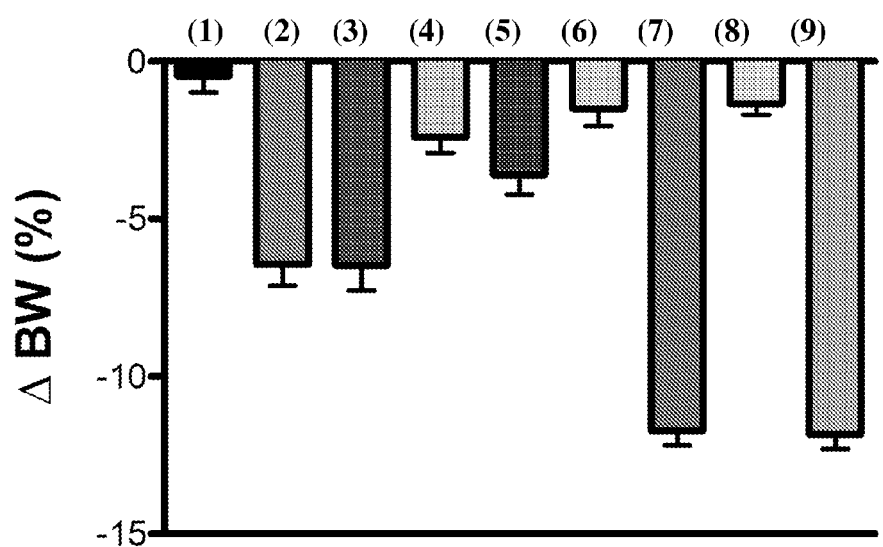
FIG. 7 Total change in body weight (BW) at day 7 (A) and cumulative food intake (FI) (B) after application of different compounds. (1)/open circle: vehicle control; (2)/closed circles: peptide-long24C (10 nmol); (3)/diamond: peptide-long24N-G3Fc (10 nmol); (4)/big filled squares: Dulaglutide (1 nmol); (5)/small filled squares: Dulaglutide (10 nmol); (6)/big filled triangles: compound 42 (1 nmol); (7)/small filled triangles: compound 42 (10 nmol); (8)/big filled upside-down triangle: compound 45 (1 nmol); (9)/small filled upside-down triangle: compound 45 (10 nmol).
Figure 7:
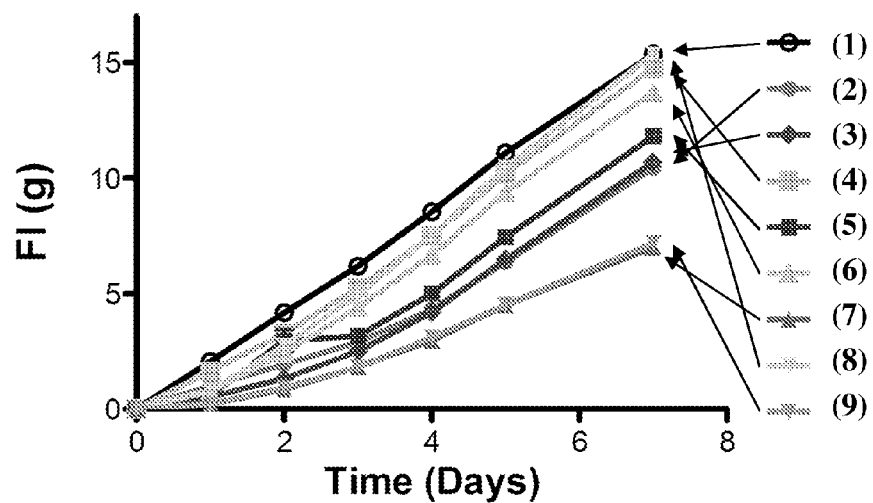
Figure 8:
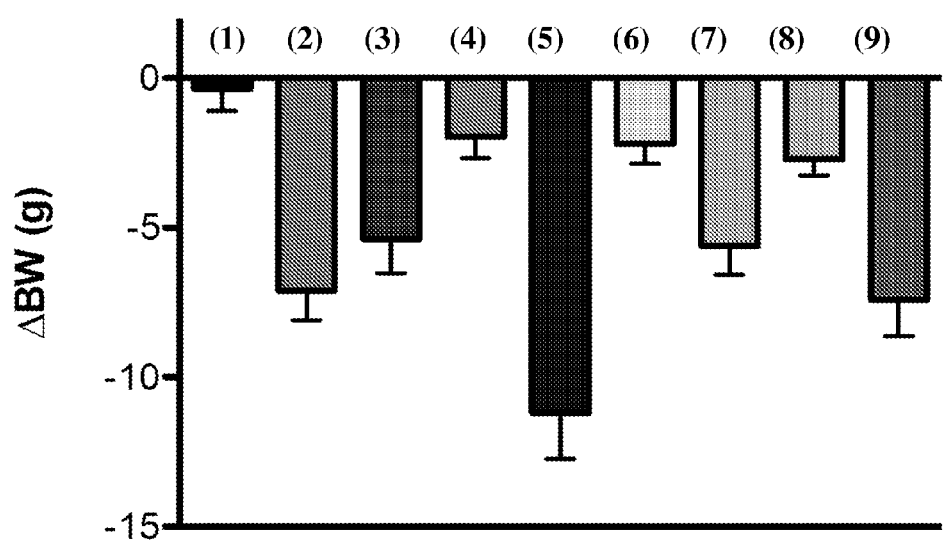
FIG. 8 Total change in body weight (BW) at day 14. (1) control N-terminal triple G motif LALAPG Fc-region; SEQ ID NO: 117 (10 nmol); (2) compound 42 (10 nmol); (3) peptide-long-G3Fc (LALAPG) (10 nmol); (4) compound 74 (1 nmol); (5) compound 74 (10 nmol); (6) compound 77 (1 nmol); (7) compound 77 (10 nmol); (8) compound 80 (1 nmol); (9) compound 80 (10 nmol).
Figure 9:
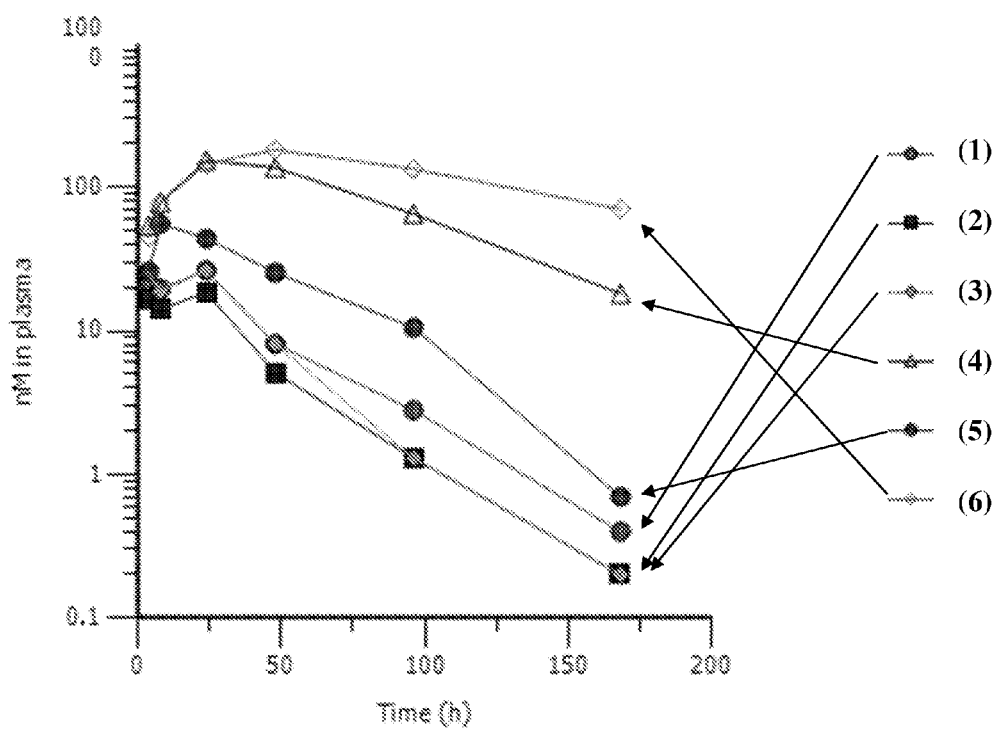
FIG. 9 In vivo half-live of different compounds. (1)/circles with black shape outline: peptide-long-human IgG1 Fc-region fusion polypeptide; (2)/square: peptide-long G4S3-Fc-region fusion polypeptide; (3)/filled diamond: peptide-short-G4S3-Fc-region fusion polypeptide; (4)/triangle: peptide-long; (5)/solid circle: compound 42; (6)/open diamond: peptide-long-G3Fc (LALAPG).

The lipidated incretin receptor ligand polypeptides as reported herein (either isolated or as Fc-region fusion polypeptide) act as dual GLP/GIP agonists and show improved biological activity in vivo compared to other non-lipidated incretin receptor ligand polypeptides or derivatives (PEGylated or Fc-region fusion polypeptides) (see FIGS. 6 to 8). Additionally the exposure and in vivo half-live is improved (FIG. 9).

The desired use is the antagonization of a cell-bound target (=receptor) and, thus, a non-effector function eliciting Fc-region isotype or Fc-region variant should be selected.

Thus, mutations at defined positions in the Fc-region of an Fc-region comprising fusion polypeptide resulting in a complete reduction of the Fc-region associated effector function are introduced in the human immunoglobulin Fc-region of the fusion polypeptide.

The circulating half-life of an Fc-region fusion polypeptide can be influenced by modulating the Fc-region-FcRn interaction. This can be achieved by changing specific amino acid residues in the Fc-region (Dall'Acqua, W. F., et al., J. Biol. Chem. 281 (2006) 23514-23524; Petkova, S. B., et al., Internat. Immunol. 18 (2006) 1759-1769; Vaccaro, C., et al. Proc. Natl. Acad. Sci. 103 (2007) 18709-18714).

The minimization or even removal of antibody-dependent cell-mediated cytotoxicity (ADCC) and complement-dependent cytotoxicity (CDC) can be achieved by so called hinge-region amino acid changes/substitutions. The amino acid residues chosen for substitution are those expected to be involved in the binding of the Fc-region to human Fc receptors (but not FcRn). This/these amino acid residue changes result in an improved safety profile compared to Fc-region fusion polypeptides s comprising a wild-type IgG Fc-region.

The classical complement cascade is initiated by the binding and activation of C1q by antigen/IgG immune complexes. This activation results in inflammatory and/or immunoregulatory responses. The minimization or even removal of the activation of the classical complement cascade can be achieved by so called hinge-region amino acid changes/substitutions. The amino acid residues chosen for substitution are those expected to be involved in the binding of the Fc-region to component C1q. One exemplary Fc-region variant with reduced or even eliminated C1q binding is the Fc-region variant comprising the mutations L234A and L235A (LALA).

The binding of an Fc-region fusion polypeptide to the neonatal receptor (FcRn) results in the transport of the polypeptide across the placenta and affects the circulatory half-life of the Fc-region fusion polypeptide. An increase of the circulatory half-life of an Fc-region fusion polypeptide results in an improved efficacy, a reduced dose or frequency of administration, or an improved localization to the target. A reduction of the circulatory half-life of an Fc-region fusion polypeptide results in a reduced whole body exposure or an improved target-to-non-target binding ratio.

The amino acid residues required for FcRn binding that are conserved across species are the histidine residues at position 310 and 435 in the Fc-region. These residues are responsible for the pH dependence of the Fc-region FcRn interaction (see, e.g., Victor, G., et al., Nature Biotechnol. 15 (1997) 637-640); Dall'Acqua, W. F., et al. J. Immunol. 169 (2002) 5171-5180). Fc-region mutations that attenuate interaction with FcRn can reduce antibody half-life.

Generally, the fusion polypeptide as reported herein comprises a variant Fc-region. However, the human immunoglobulin Fc-region of the fusion polypeptide may already have one or more amino acid sequence alterations compared to a wild-type Fc-region. For example, the C1q or FcγR binding activity of the parent Fc-region may have been altered (other types of Fc-region modifications are described in more detail below).

In one embodiment the nucleic acid encoding the parent Fc-region of the fusion polypeptide is altered to generate a variant nucleic acid sequence encoding the variant Fc-region of the fusion polypeptide.

The nucleic acid encoding the amino acid sequence of the variant Fc-region of the fusion polypeptide can be prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the Fc-region of the fusion polypeptide, or can be generated chemically by DNA synthesis.

Site-directed mutagenesis is a suitable method for preparing substitution variants. This technique is well known in the art (see, e.g., Carter, et al., Nucl. Acids Res. 13 (1985) 4431-4443, Kunkel, et al., Proc. Natl. Acad. Sci. USA 82 (1985) 488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide (see e.g. Higuchi, in PCR Protocols, Academic Press (1990) pp. 177-183, Vallette, et al., Nucl. Acids Res. 17 (1989) 723-733). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells, et al., in Gene 34 (1985) 315-323.

One aspect as reported herein is a fusion polypeptide comprising a human immunoglobulin Fc-region and one to four incretin receptor ligand polypeptides, in which at least one of the incretin receptor ligand polypeptides comprises and amino acid residue that is covalently conjugated to a lipid, and in which at least one amino acid residue in the human immunoglobulin Fc region has been altered by addition, mutation, or deletion, resulting in reduced or ablated affinity of the fusion polypeptide for at least one Fc receptor compared to a fusion polypeptide comprising the parent or wild-type human immunoglobulin Fc-region.

The Fc-region interacts with a number of receptors or ligands including but not limited to Fc receptors (e.g. FcγRI, FcγRIIA, FcγRIIIA), the complement protein C1q, and other molecules such as proteins A and G. These interactions are essential for a variety of effector functions and downstream signaling events including, but not limited to, antibody dependent cell-mediated cytotoxicity (ADCC), antibody dependent cellular phagocytosis (ADCP) and complement dependent cytotoxicity (CDC).

In one embodiment the fusion polypeptide as reported herein comprises a human immunoglobulin Fc-region that has reduced or ablated affinity for an Fc receptor, which can elicit an effector function, compared to a fusion polypeptide that comprises a parent or wild-type human immunoglobulin Fc-region, wherein the amino acid sequence of the variant human immunoglobulin Fc-region differs from the amino acid sequence of the parent human immunoglobulin Fc-region by at least one addition, mutation, or deletion of at least one amino acid residue.

In one embodiment the fusion polypeptide as reported herein has at least one or more of the following properties: reduced or ablated effector function (ADCC and/or CDC and/or ADCP), reduced or ablated binding to Fc receptors, reduced or ablated binding to C1q, or reduced or ablated toxicity.

In one embodiment the fusion polypeptide as reported herein comprises a variant human immunoglobulin Fc-region that has at least a mutation or deletion of the proline amino acid residue at position 329 according to the EU index of Kabat.

If one amino acid residue is deleted from an amino acid sequence the remaining amino acid residues maintain their EU-index number although the actual position in the amino acid sequences changes in order to allow the precise identification of specific amino acid residues in multiply mutated Fc-regions.

In one embodiment the fusion polypeptides comprises a wild-type human Fc-region with an amino acid mutation at position 329 according to the EU index of Kabat. In one embodiment the proline residue at amino acid position 329 in the Fc-region is mutated to an amino acid residue which is either smaller or larger than proline. In one embodiment the amino acid residue is mutated to glycine, alanine or arginine. In one preferred embodiment the amino acid residue proline at position 329 according to the EU index of Kabat in the Fc-region is mutated to glycine.

In one embodiment the fusion polypeptide comprises at least one further amino acid mutation in the human immunoglobulin Fc-region.

In one embodiment the fusion polypeptide as reported herein comprises a wild-type human immunoglobulin Fc-region that has at least three amino acid mutations, additions, or deletions.

In one embodiment the fusion polypeptide as reported herein comprises at least one amino acid substitution in the human immunoglobulin Fc-region that is selected from the group comprising S228P, E233P, L234A, L235A, L235E, N297A, N297D, and P331S.

In one embodiment the human immunoglobulin Fc-region is a human IgG1 Fc-region or a human IgG4 Fc-region.

In one embodiment, the further addition, mutation, or deletion of an amino acid residue in the human immunoglobulin Fc-region is at position 228 and/or 235 of the Fc-region if the Fc-region is of IgG4 isotype. In one embodiment the amino acid residue serine at position 228 is substituted by a proline residue and the amino acid residue leucine at position 235 is substituted by a glutamic acid residue.

In one embodiment the fusion polypeptide comprises three amino acid mutations in the human immunoglobulin Fc-region. In one embodiment the three amino acid mutations are P329G, S228P and L235E (SPLEPG).

In one embodiment, the further addition, mutation, or deletion of an amino acid residue in the Fc-region fusion polypeptide as reported herein is at position 234 and/or 235 of the Fc-region if the Fc-region is of IgG1 isotype. In one embodiment the amino acid residue leucine at position 234 is substituted by an alanine residue and the amino acid residue leucine at position 235 is substituted by an alanine residue.

While in one embodiment the binding to an FcγR is altered, fusion polypeptides with altered binding affinity for the neonatal receptor (FcRn) are also an embodiment of the aspects as reported herein.

Fc-region variants with increased affinity for FcRn have longer serum half-lives, and such molecules will have useful applications in methods of treating mammals where long half-life of the administered fusion polypeptide is desired, e.g., to treat a chronic disease or disorder.

Fc-region variants with decreased FcRn binding affinity have shorter serum half-lives, and such molecules will have useful applications in methods of treating mammals where shorter half-life of the administered fusion polypeptide is desired, e.g. to avoid toxic side effects or for in vivo diagnostic imaging applications. Fc-regions with decreased FcRn binding affinity are less likely to cross the placenta, and thus may be utilized in the treatment of diseases or disorders in pregnant women.

Fc-regions with altered binding affinity for FcRn comprise in one embodiment those comprising an Fc-region with an amino acid alteration at one or more of the amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447.

Fc-regions with reduced binding to FcRn comprise in one embodiment an Fc-region with one or more amino acid alterations at the amino acid positions 252, 253, 254, 255, 288, 309, 386, 388, 400, 415, 433, 435, 436, 439, and/or 447.

Fc-regions which display increased binding to FcRn comprise in one embodiment an Fc-region with one or more amino acid alterations at the amino acid positions 238, 256, 265, 272, 286, 303, 305, 307, 311, 312, 317, 340, 356, 360, 362, 376, 378, 380, 382, 413, 424, and/or 434.

The fusion polypeptide may comprise a human immunoglobulin Fc-region of any class (for example, but not limited to IgG, IgM, and IgE). In one embodiment the fusion polypeptide comprises a human immunoglobulin Fc-region of the IgG class. In one embodiment the fusion polypeptide comprises a human immunoglobulin Fc-region of the IgG1, IgG2, IgG3, or IgG4 subclass.

In one embodiment the fusion polypeptide comprises a human immunoglobulin Fc-region of the IgG1 subclass and comprise the amino acid mutations P329G, and/or L234A and L235A in the Fc-region.

In one embodiment the fusion polypeptide comprises a human immunoglobulin Fc-region of the IgG4 subclass. In one embodiment the fusion polypeptide comprises a human immunoglobulin Fc-region of the IgG4 subclass and comprises the amino acid mutations P329G, and/or S228P and L235E in the Fc-region.

In one embodiment the fusion polypeptide as reported herein is produced by conjugating a biologically active polypeptide with a human immunoglobulin Fc-region comprising one or more of the amino acid mutations as reported herein. In one embodiment the fusion polypeptide as reported herein is produced by modifying a parent Fc-region fusion polypeptide by introducing one or more of the amino acid mutations as reported herein.

Enzymatic Conjugation Using Sortase A

A conjugate comprising an Fc-region and one or more lipidated incretin receptor ligand polypeptides can be obtained by using the enzyme Sortase A.

Sortase A (SrtA) is a membrane bound enzyme which attaches proteins covalently to the bacterial cell wall. The specific recognition motif on the SrtA substrate is LPXTG (SEQ ID NO: 75), whereby the enzyme cleaves between the residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthesized peptides to recombinantly expressed proteins.

For the enzymatic conjugation of a lipidated incretin receptor ligand polypeptide (e.g. with GIP receptor and GLP-1 receptor dual agonistic activity) to a human immunoglobulin Fc-region of the subclass IgG1 a soluble SrtA (amino acid residues 60-206 of Staph. aureus SrtA) can be used. The enzyme can be produced in E. coli. The human immunoglobulin Fc-region modified with a triple G motif at the respective N-termini of the heavy chains to be conjugated and a SrtA recognition motif at the respective C-termini of the heavy chain to be conjugated can be expressed in eukaryotic cells (e.g. HEK293 cells, CHO cells). A corresponding triple G motif or SrtA recognition motif is introduced at the respective N-terminus or C-terminus of the lipidated incretin receptor ligand polypeptide.

One aspect as reported herein is a lipidated incretin receptor ligand Fc-region fusion polypeptide that is obtained by conjugating the lipidated incretin receptor ligand polypeptides to the human immunoglobulin Fc-region using the enzyme Sortase A, wherein a sortase recognition sequence is located at the C-terminus of the lipidated incretin receptor ligand polypeptide and/or the C-terminus of one or both Fc-region heavy chain fragments, and wherein a triple glycine motif is located either at the N-terminus of the lipidated incretin receptor ligand polypeptide and/or at the N-terminus of one or both Fc-region heavy chain fragments.

Accordingly, the invention provides a polypeptide comprising the amino acid sequence of the lipidated incretin receptor ligand polypeptide and the amino acid sequence of a sortase recognition sequence. In exemplary aspects, the invention provides a polypeptide comprising the amino acid sequence of a lipidated incretin receptor ligand polypeptide and LPXTG (SEQ ID NO: 75), wherein X is any amino acid. In exemplary aspects, the X is an acidic amino acid, e.g., Asp, Glu. In exemplary aspects, the X is Glu. In exemplary aspects, the polypeptide comprises one or more Gly residues N-terminally to LPXTG (SEQ ID NO: 75), wherein X is any amino acid. In alternative or additional embodiments, the polypeptide comprises Gly-Gly or Gly-Gly-Ser or Gly-Gly-Gly (SEQ ID NO: 99), Gly-Gly-Gly-Ser (SEQ ID NO: 79), Gly-Gly-Gly-Gly (SEQ ID NO: 80), or Gly-Gly-Gly-Gly-Ser (SEQ ID NO: 81)C-terminally to LPXTG (SEQ ID NO: 73). In exemplary aspects, the polypeptide comprises $(GGS)_n$, wherein n=1-4 (SEQ ID NOs: 82-84), or $G_n$, wherein n=2-6 (SEQ ID NOs: 85-87), $(GGGS)_n$, wherein n=1-6 (SEQ ID NOs: 57-60, 88 and 89), $(GGGGS)_m$, wherein m=1-6 (SEQ ID NOs: 61-64, 90 and 91, or $(GGGGGS)_o$, wherein o=1-6 (SEQ ID NOs: 65-67 and 92-94).

In one embodiment one or both of the Fc-region heavy chain fragments comprises a linker polypeptide located between the C-terminus of the triple G motif and the N-terminus of the Fc-region heavy chains and/or between the C-terminus of the Fc-region heavy chain and the N-terminus of the SrtA recognition motif.

In one embodiment the incretin receptor ligand polypeptide comprises a linker polypeptide located between the N-terminus of the SrtA recognition sequence and the C-terminus of the incretin receptor ligand polypeptide.

In one embodiment the incretin receptor ligand polypeptide comprises a linker polypeptide located between the C-terminus of the triple G recognition sequence and the N-terminus of the incretin receptor ligand polypeptide.

In one embodiment the linker polypeptide has a length of from 9 to 25 amino acid residues. In one embodiment the linker polypeptide is selected from $(GGGS)_3$ (SEQ ID NO: 57), $(GGGS)_4$ (SEQ ID NO: 58), $(GGGS)_5$ (SEQ ID NO: 59), $(GGGS)_6$ (SEQ ID NO: 60), $(GGGGS)_2$ (SEQ ID NO: 61), $(GGGGS)_3$ (SEQ ID NO: 62), $(GGGGS)_4$ (SEQ ID NO: 63), $(GGGGS)_5$ (SEQ ID NO: 64), $(GGGGGS)_2$ (SEQ ID NO: 65), $(GGGGGS)_3$ (SEQ ID NO: 66), and $(GGGGGS)_4$ (SEQ ID NO: 67).

In exemplary aspects, the invention provides a polypeptide comprising the amino acid sequence of the lipidated incretin receptor ligand polypeptide and the linker, e.g. a linker comprising the amino acid sequence of any of SEQ ID NOs: 57-67.

In one embodiment the fusion polypeptide comprises one lipidated incretin receptor ligand polypeptide. In this embodiment the incretin receptor ligand polypeptide is conjugated to a single N- or C-terminus of the Fc-region. Also in this embodiment the Fc-region is a heterodimer of two antibody heavy chain Fc-region fragments whereof only one comprises the incretin receptor ligand polypeptide (after conjugation) or an oligoglycine/SrtA recognition motif (prior to conjugation).

Conjugates comprising a human IgG1 Fc-region conjugated to lipidated incretin receptor ligand polypeptides which have dual agonistic properties by activating the GIP receptor and the GLP-1 receptor can be used to control blood glucose level and for robust fat mass loss.

It has been shown that such a conjugate has in diabetic db/db mice resulted in reducing the blood glucose excursion following an intraperitoneal glucose challenge. In addition, in diet-induced obese (DIO) mice, it has been observed that administration of such a lipidated incretin receptor ligand polypeptide Fc-region fusion polypeptide is able to induce reduced food uptake and robust body weight loss following a single dose.

The activation of incretin receptors, such as the GLP-1- and GIP-receptors, results in glucose-dependent insulin secretion, proliferation, and protection of pancreatic beta cells from lipotoxicity and prevention of apoptosis that is mediated by pathways downstream of PKA and/or EPAC activation (Dzhura, I., et al., Islets 3 (2011) 121-128; Ehses, J. A., et al., Endocrin. 144 (2003) 4433-4445; Kang, G., et al., J. Biol. Chem. 278 (2003) 8279-8285; Miura, Y. and Matsui, H., Tox. Appl. Pharmacol. 216 (2006) 363-372; Mukai, E., et al., Diabetes 60 (2011) 218-226; Natalicchio, A., et al., Endocrin. 151 (2010) 2019-2029; Quoyer, J., et al., J. Biol. Chem. 285 (2010) 1989-2002; Uhles, S., et al., Diabetes Obes. Metabol. 13 (2010) 326-336).

Further, incretin receptors such as the GLP-1 and GIP receptors have been detected in the pancreatic alpha-cells that secrete glucagon.

The presence of incretin receptors, such as the GLP-1 receptor, has been reported in the vagus nerve as well as a wide distribution in the CNS. Activation of the portal GLP-1 receptors is reported to play a critical role in glucose homeostasis (Burcelin, R., et al., Diabetes 50 (2001) 1720-1728; Vahl, T. P., et al., Endocrin. 148(2007) 4965-4973). In addition, GLP-1 receptors expressed in the arcuate nucleus have been implicated in regulating glucose levels (Sandoval, D. A., et al., Diabetes 57 (2008) 2046-2054).

Activation of GLP-1 receptors in the hind brain and in the hypothalamus plays an important role in limiting food consumption and prevention of obesity (Hayes, M. R., et al., Endocrinol. 150 (2009) 2654-2659; McMahon, L. R. and Wellman, P. J., Am. J. Physiol. 274 (1998) R23-29; Turton, M. D., et al., Nature 379 (1996) 69-72).

GIP and GIP-receptors are present in the CNS. GIP in the CNS is thought to play a role in neurogenesis and memory (Figueiredo, C. P., et al., Behav. Pharmacol. 21 (2010) 394-408; Nyberg, J., et al., J. Neurosci. 25 (2005) 1816-1825).

Incretin receptors, such as the GIP receptor, are present on adipocytes and induce lipolysis and re-esterification of fatty acids (Getty-Kushik, L., et al., Obesity 14 (2006) 1124-1131). In addition, GIP receptor activation leads to increased LPL expression on human adipocytes (Kim, S. J., et al., J. Biol. Chem. 282 (2007) 8557-8567; Kim, S. J., et al., J. Lipid Res. 51 (2010) 3145-3157).

III. Recombinant Methods

Parts of the fusion polypeptides as reported herein may be produced using recombinant methods and compositions, see e.g. U.S. Pat. No. 4,816,567.

In one aspect an isolated nucleic acid encoding a part of the fusion polypeptide as reported herein is provided.

In one aspect one or more vectors (e.g., expression vectors) comprising such nucleic acid are provided.

In one aspect a host cell comprising such nucleic acid is provided. In one embodiment a host cell comprises (e.g., has been transformed with): (1) a vector comprising a nucleic acid that encodes an amino acid sequence comprising the first heavy chain Fc-region of the fusion polypeptide and an amino acid sequence comprising the second heavy chain Fc-region of the fusion polypeptide, or (2) a first vector comprising a nucleic acid that encodes an amino acid sequence comprising the first heavy chain Fc-region of the fusion polypeptide and a second vector comprising a nucleic acid that encodes an amino acid sequence comprising the second heavy chain Fc-region of the fusion polypeptide.

In one embodiment, the host cell is a eukaryotic cell, e.g. a human embryonic kidney (HEK) cell, or a Chinese Hamster Ovary (CHO) cell, or a lymphoid cell (e.g., Y0, NS0, Sp20 cell).

In one aspect a method of making a fusion polypeptide as reported herein is provided, wherein the method comprises culturing a host cell comprising a nucleic acid encoding the Fc-region part of the fusion polypeptide as provided above, under conditions suitable for expression of the Fc-region part of the polypeptide, and optionally recovering the Fc-region part of the fusion polypeptide from the host cell (or host cell culture medium) and conjugating the recombinantly produced Fc-region part of the fusion polypeptide with the respective other lipidated incretin receptor ligand part of the fusion polypeptide chemically or enzymatically. The lipidated incretin receptor ligand polypeptide part of the fusion polypeptide can be produced recombinantly and modified thereafter or can be produced completely synthetically.

For recombinant production of a part of the fusion polypeptide, a nucleic acid encoding a part of the fusion polypeptide, e.g., as described above, is isolated and inserted into one or more vectors for further cloning and/or expression in a host cell. Such nucleic acid may be readily isolated and/or produced using conventional procedures.

Suitable host cells for cloning or expression of polypeptide-encoding vectors include prokaryotic or eukaryotic cells described herein. For example, polypeptides may be produced in bacteria, in particular when glycosylation and Fc effector function are not needed (see, e.g., U.S. Pat. No. 5,648,237, U.S. Pat. No. 5,789,199, and U.S. Pat. No. 5,840,523, Charlton, Methods in Molecular Biology 248 (2003) 245-254 (B. K. C. Lo, (ed.), Humana Press, Totowa, N.J.), describing expression of antibody fragments in *E. coli.*). After expression, the polypeptide may be isolated from the bacterial cell paste in a soluble fraction and can be further purified.

In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gerngross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. No. 5,959,177, U.S. Pat. No. 6,040,498, U.S. Pat. No. 6,420,548, U.S. Pat. No. 7,125,978, and U.S. Pat. No. 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or kidney cells (BHK); mouse sertoli cells (TM4 cells as described, e.g., in Mather, Biol. Reprod. 23 (1980) 243-251); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, et al., Annals N.Y. Acad. Sci. 383 (1982) 44-68; MRC 5 cells; and FS4 cells. Other useful mammalian host cell lines include Chinese hamster ovary (CHO) cells, including DHFR negative CHO cells (Urlaub, et al., Proc. Natl. Acad. Sci. USA 77 (1980) 4216), and myeloma cell lines such as Y0, NS0 and Sp2/0. For a review of certain mammalian host cell lines suitable for polypeptide production, see, e.g., Yazaki, and Wu, Methods in Molecular Biology 248 (2003) 255-268 (B. K. C. Lo, (ed.), Humana Press, Totowa, N.J.).

IV. Pharmaceutical Formulations

Pharmaceutical formulations of a fusion polypeptide as reported herein are prepared by mixing such fusion polypeptide having the desired degree of purity with one or more optional pharmaceutically acceptable carriers (Osol, A., (ed.), Remington's Pharmaceutical Sciences, 16$^{th}$ edition, (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly (vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, especially those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences $16^{th}$ edition, Osol, A., (ed.), (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

V. Therapeutic Methods and Compositions

Any of the fusion polypeptides as reported herein may be used in therapeutic methods.

In one aspect of the invention the fusion polypeptide as reported herein is used for treating a disease. In one embodiment the disease is such, that it is favorable that the effector function of the fusion polypeptide is strongly, at least by 50%, in one preferred embodiment by more than 95%, reduced compared to the fusion polypeptide comprising a wild-type human immunoglobulin Fc-region.

In one aspect the fusion polypeptide as reported herein is used in the manufacture of a medicament for the treatment of a disease, wherein it is favorable that the effector function of the fusion polypeptide is strongly reduced, in one preferred embodiment the effector function is reduced by more than 95%, compared to a fusion polypeptide comprising a wild-type human immunoglobulin Fc-region.

One aspect as reported herein is a method of treating an individual having a disease, wherein it is favorable that the effector function of the fusion polypeptide as reported herein is strongly reduced compared to a fusion polypeptide comprising a wild-type human immunoglobulin Fc-region, comprising administering to the individual an effective amount of the fusion polypeptide as reported herein.

A strong reduction of effector function is a reduction of effector function by at least 50% of the effector function induced by the fusion polypeptide comprising a wild-type human immunoglobulin Fc-region.

Such diseases are for example all diseases where the targeted cell should not be destroyed by for example ADCC, ADCP, or CDC.

The conditions which can be treated with the fusion polypeptide as reported herein are many and include metabolic disorders.

The fusion polypeptide as reported herein is administered by any suitable means, including enteral (orally or rectally), gastrointestinal, sublingual, sublabial, parenteral, subcutaneous, intravenous, intradermal, intraperitoneal, intrapulmonary, and intranasal. In one embodiment the dosing is given by tablet, capsule, or droplet.

For the prevention or treatment of disease, the appropriate dosage of the fusion polypeptide will depend on the type of disease to be treated, the severity and course of the disease, whether the fusion polypeptide is administered for preventive or therapeutic purposes, previous therapy, the patient's clinical history and response to the fusion polypeptide, and the discretion of the attending physician. The fusion polypeptide is suitably administered to the patient at one time or over a series of treatments.

Depending on the type and severity of the disease, about 1 µg/kg to 15 mg/kg (e.g., 0.1-20 mg/kg) of fusion polypeptide is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

Metabolic Syndrome, also known as metabolic syndrome X, insulin resistance syndrome or Reaven's syndrome, is a disorder that affects over 50 million Americans. Metabolic Syndrome is typically characterized by a clustering of at least three or more of the following risk factors: (1) abdominal obesity (excessive fat tissue in and around the abdomen), (2) atherogenic dyslipidemia (blood fat disorders including high triglycerides, low HDL cholesterol and high LDL cholesterol that enhance the accumulation of plaque in the artery walls), (3) elevated blood pressure, (4) insulin resistance or glucose intolerance, (5) prothrombotic state (e.g. high fibrinogen or plasminogen activator inhibitor-1 in blood), and (6) pro-inflammatory state (e.g. elevated C-reactive protein in blood). Other risk factors may include aging, hormonal imbalance and genetic predisposition.

Metabolic Syndrome is associated with an increased the risk of coronary heart disease and other disorders related to the accumulation of vascular plaque, such as stroke and peripheral vascular disease, referred to as atherosclerotic cardiovascular disease (ASCVD). Patients with Metabolic Syndrome may progress from an insulin resistant state in its early stages to full blown type II diabetes with further increasing risk of ASCVD. Without intending to be bound by any particular theory, the relationship between insulin resistance, Metabolic Syndrome and vascular disease may involve one or more concurrent pathogenic mechanisms including impaired insulin-stimulated vasodilation, insulin resistance-associated reduction in NO availability due to enhanced oxidative stress, and abnormalities in adipocyte-derived hormones such as adiponectin (Lteif and Mather, Can. J. Cardiol. 20 (suppl. B) (2004) 66B-76B).

According to the 2001 National Cholesterol Education Program Adult Treatment Panel (ATP III), any three of the following traits in the same individual meet the criteria for Metabolic Syndrome: (a) abdominal obesity (a waist circumference over 102 cm in men and over 88 cm in women); (b) serum triglycerides (150 mg/dl or above); (c) HDL cholesterol (40 mg/dl or lower in men and 50 mg/dl or lower in women); (d) blood pressure (130/85 or more); and (e) fasting blood glucose (110 mg/dl or above). According to the World Health Organization (WHO), an individual having high insulin levels (an elevated fasting blood glucose or an elevated post meal glucose alone) with at least two of the following criteria meets the criteria for Metabolic Syndrome: (a) abdominal obesity (waist to hip ratio of greater than 0.9, a body mass index of at least 30 kg/m$^2$, or a waist measurement over 37 inches); (b) cholesterol panel showing a triglyceride level of at least 150 mg/dl or an HDL cholesterol lower than 35 mg/dl; (c) blood pressure of 140/90 or more, or on treatment for high blood pressure) (see e.g. Mathur, Ruchi, "Metabolic Syndrome," ed. Shiel, Jr., William C., MedicineNet.com, May 11, 2009).

For purposes herein, if an individual meets the criteria of either or both of the criteria set forth by the 2001 National Cholesterol Education Program Adult Treatment Panel or the WHO, that individual is considered as afflicted with Metabolic Syndrome.

Without being bound to any particular theory, the fusion polypeptides described herein are useful for treating Metabolic Syndrome. Accordingly, the invention provides a method of preventing or treating Metabolic Syndrome, or reducing one, two, three or more risk factors thereof, in a subject, comprising administering to the subject a fusion polypeptide described herein in an amount effective to prevent or treat Metabolic Syndrome, or the risk factor thereof.

One aspect as reported herein is a fusion polypeptide as reported herein for use in a method of treating an individual having diabetes or obesity comprising administering to the individual an effective amount of the fusion polypeptide as reported herein. In one embodiment, the method further comprises administering to the individual an effective amount of at least one additional therapeutic agent.

In one aspect a fusion polypeptide as reported herein is provided for use in stimulation of insulin synthesis and/or secretion, inhibition of glucagon secretion, inhibition of food intake, or/and reduction of hyperglycemia in an individual comprising administering to the individual an effective dose of the fusion polypeptide as reported herein to stimulate insulin synthesis and/or secretion, inhibit glucagon secretion, inhibit of food intake, or/and reduce hyperglycemia in an individual. In one embodiment the individual is a human.

In one aspect methods for inducing weight loss or preventing weight gain are provided herein, which involve administering to a patient in need thereof an effective amount of a fusion polypeptide as reported herein, that exhibits activity at both the GIP receptor and the GLP-I receptor, and that optionally also exhibits activity at the glucagon receptor. Such compounds include the GIP/GLP-1 co-agonists and glucagon/GIP/GLP-1 tri-agonists described herein.

One aspect as reported herein is the use of a fusion polypeptide as reported herein in the manufacture or preparation of a medicament. In one embodiment, the medicament is for treatment of diabetes or obesity. In a further embodiment, the medicament is for use in a method of treating diabetes or obesity comprising administering to an individual having diabetes or obesity an effective amount of the medicament. In one embodiment the method further comprises administering to the individual an effective amount of at least one additional therapeutic agent. In a further embodiment the medicament is for stimulation of insulin synthesis and/or secretion, inhibition of glucagon secretion, inhibition of food intake, or/and reduction of hyperglycemia.

In a further embodiment, the medicament is for use in a method of stimulating insulin synthesis and/or secretion, inhibiting glucagon secretion, inhibiting food intake, or/and reducing hyperglycemia in an individual comprising administering to the individual an amount effective of the medicament to stimulate insulin synthesis and/or secretion, inhibit glucagon secretion, inhibit food intake, or/and reduce hyperglycemia. An "individual" according to any of the above embodiments may be a human.

Nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). Simple fatty liver is the abnormal accumulation of a certain type of fat, triglyceride, in the liver cells with no inflammation or scarring. In NASH, the fat accumulation is associated with varying degrees of inflammation (hepatitis) and scarring (fibrosis) of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. NASH can ultimately lead to scarring of the liver (fibrosis) and then irreversible, advanced scarring (cirrhosis). Cirrhosis that is caused by NASH is the last and most severe stage in the NAFLD spectrum. (Mendler, Michel, "Fatty Liver: Nonalcoholic Fatty Liver Disease (NAFLD) and Nonalcoholic Steatohepatitis (NASH)," ed. Schoenfield, Leslie J., MedicineNet-.com, Aug. 29, 2005).

Alcoholic Liver Disease, or Alcohol-Induced Liver Disease, encompasses three pathologically distinct liver diseases related to or caused by the excessive consumption of alcohol: fatty liver (steatosis), chronic or acute hepatitis, and cirrhosis. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Histologically, alcoholic hepatitis has a characteristic appearance with ballooning degeneration of hepatocytes, inflammation with neutrophils and sometimes Mallory bodies (abnormal aggregations of cellular intermediate filament proteins). Cirrhosis is characterized anatomically by widespread nodules in the liver combined with fibrosis (see e.g. Worman, Howard J., "Alcoholic Liver Disease", Columbia University Medical Center website).

Without being bound to any particular theory, the fusion polypeptides described herein are useful for the treatment of Alcoholic Liver Disease, NAFLD, or any stage thereof, including, for example, steatosis, steatohepatitis, hepatitis, hepatic inflammation, NASH, cirrhosis, or complications thereof. Accordingly, the invention provides a method of preventing or treating Alcoholic Liver Disease, NAFLD, or any stage thereof, in a subject comprising administering to a subject a fusion polypeptide described herein in an amount effective to prevent or treat Alcoholic Liver Disease, NAFLD, or the stage thereof. Such treatment methods include reduction in one, two, three or more of the following: liver fat content, incidence or progression of cirrhosis, incidence of hepatocellular carcinoma, signs of inflammation, e.g. abnormal hepatic enzyme levels (e.g., aspartate aminotransferase AST and/or alanine aminotransferase ALT, or LDH), elevated serum ferritin, elevated serum bilirubin, and/or signs of fibrosis, e.g. elevated TGF-beta levels. In preferred embodiments, the fusion polypeptides are used treat patients who have progressed beyond simple fatty liver (steatosis) and exhibit signs of inflammation or hepatitis. Such methods may result, for example, in reduction of AST and/or ALT levels.

In one aspect herein is provided a pharmaceutical formulation comprising any of the fusion polypeptides as reported herein, e.g., for use in any of the above therapeutic methods. In one embodiment, a pharmaceutical formulation comprises any of the fusion polypeptides provided herein and a pharmaceutically acceptable carrier. In one embodiment a pharmaceutical formulation comprises any of the fusion polypeptides provided herein and at least one additional therapeutic agent.

Fusion polypeptides as reported herein can be used either alone or in combination with other agents in a therapy. For instance, a fusion polypeptide as reported herein may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant.

Fusion polypeptides as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The fusion polypeptide need not be, but is optionally formulated with, one or more agents currently used to prevent or treat the disorder in question. The effective amount of such other agents depends on the amount of the fusion polypeptide present in the formulation, the type of disorder or treatment, and other factors discussed above. These are generally used in the same dosages and with administration routes as described herein, or about from 1% to 99% of the dosages described herein, or in any dosage and by any route that is empirically/clinically determined to be appropriate.

For the prevention or treatment of disease, the appropriate dosage of a fusion polypeptide as reported herein (when used alone or in combination with one or more other additional therapeutic agents) will depend on the type of disease to be treated, the type of fusion polypeptide, the severity and course of the disease, whether the fusion polypeptide is administered for preventive or therapeutic purposes, previous therapy, the patient's clinical history and response to the fusion polypeptide, and the discretion of the attending physician. The fusion polypeptide is suitably administered to the patient at one time or over a series of treatments. One exemplary dosage of the fusion polypeptide would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion polypeptide). An initial higher loading dose, followed by one or more lower doses may be administered. However, other dosage regimens may be useful. The progress of this therapy is easily monitored by conventional techniques and assays.

VI. Articles of Manufacture

In another aspect of the invention, an article of manufacture containing materials useful for the treatment, and/or prevention of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, and/or preventing the condition and may have a sterile access port (for example the container may be an intravenous solution bag or a vial having a stopper pierceable by a hypodermic injection needle). At least one active agent in the composition is a fusion polypeptide as reported herein. The label or package insert indicates that the composition is used for treating the condition of choice. Moreover, the article of manufacture may comprise (a) a first container with a composition contained therein, wherein the composition comprises a fusion polypeptide as reported herein; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The disclosures of all patent and scientific literature cited herein are expressly incorporated in their entirety by reference.

Specific Embodiments

1. A fusion polypeptide comprising
    one, two, three or four incretin receptor ligand polypeptides, and
    one human immunoglobulin Fc-region,
    wherein at least one of the incretin receptor ligand polypeptides comprises an amino acid that is covalently conjugated to a lipid, and
    wherein each of the one, two, three or four incretin receptor ligand polypeptides is covalently conjugated by a peptide bond to a terminus of the human immunoglobulin Fc-region, whereby to each terminus of the human immunoglobulin Fc-region only a single incretin receptor ligand polypeptide is conjugated.
2. The fusion polypeptide according to item 1, characterized in that the fusion polypeptide in vivo associates with an endogenous polypeptide.
3. The fusion polypeptide according to any one of items 1 to 2, characterized in that the conjugation to a lipid is via a functional group in the side chain of the amino acid.
4. The fusion polypeptide according to any one of items 1 to 3, characterized in that the amino acid residues of the incretin receptor ligand polypeptide that is covalently conjugated to a lipid is a non-naturally occurring amino acid residue.
5. The fusion polypeptide according to any one of items 1 to 4, characterized in that the lipid is selected from the group comprising fatty acids, glycerolipids, glycerophospholipids, sphingolipids, sterol lipids, prenol lipids, saccharolipids and polyketides.
6. The fusion polypeptide according to any one of items 1 to 5, characterized in that the conjugation to a lipid is selected from the group comprising myristoylation (14:0), palmitoylation (16:0), prenylation, octaonylation, archaeolyation, cholesterylation.
7. The fusion polypeptide according to item 6, characterized in that the conjugation to a lipid is palmitoylation.
8. The fusion polypeptide according to any one of items 1 to 7, characterized in that i) in case the incretin receptor ligand polypeptide is conjugated via its C-terminus to the human immunoglobulin Fc-region the amino acid sequence LPXTG (SEQ ID NO: 75), optionally, LPETG (SEQ ID NO: 74) is between the C-terminus of the incretin receptor ligand polypeptide and the N-terminus of the human immunoglobulin Fc-region, and
ii) in case the incretin receptor ligand polypeptide is conjugated via its N-terminus to the human immunoglobulin Fc-region the amino acid sequence LPXTG (SEQ ID NO: 75), optionally, LPETG (SEQ ID NO: 74) is between the N-terminus of the incretin receptor ligand polypeptide and the C-terminus of the human immunoglobulin Fc-region.
9. The fusion polypeptide according to any one of items 1 to 8, characterized in that the incretin receptor ligand polypeptide is a naturally occurring incretin receptor ligand polypeptide or a synthetic incretin receptor ligand polypeptide.
10. The fusion polypeptide according to any one of items 1 to 9, characterized in that the incretin receptor ligand polypeptide comprises an amino acid sequence selected from the group consisting of SEQ ID NOs: 1-39, 76, 77, and 120-125.
11. The fusion polypeptide according to any one of items 1 to 10, characterized in comprising the amino acid sequence LPETG (SEQ ID NO: 74) between the amino acid sequence of the incretin receptor ligand polypeptide and the amino acid sequence of the human immunoglobulin Fc-region.
12. The fusion polypeptide according to any one of items 8 to 11, characterized in comprising one of the polypeptides Gly-Gly or Gly-Gly-Ser or Gly-Gly-Gly, Gly-Gly-Gly-Ser (SEQ ID NO: 88), Gly-Gly-Gly-Gly (SEQ ID NO: 85), or Gly-Gly-Gly-Gly-Ser (SEQ ID NO: 90)C- or N-terminally to LPETG (SEQ ID NO: 74).
13. The fusion polypeptide according to items 8 to 12, characterized in comprising (GGGS)$_n$, wherein n=1-6 (SEQ ID NOs: 57-60, 88 and 89), (GGGGS)$_m$, wherein m=1-6 (SEQ ID NOs: 61-64, 90 and 91), or (GGGGGS)$_o$, wherein o=1-6 (SEQ ID NOs: 65-67 and 92-94).
14. The fusion polypeptide according to any one of items 8 to 12, comprising any one of SEQ ID NOs: 57-67.
15. The fusion polypeptide according to any one of items 8 to 14, comprising Gly or Gly-Gly C- or N-terminally to LPXTG (SEQ ID NO: 75).
16. The fusion polypeptide according to any one of items 1 to 15, characterized in that the human immunoglobulin Fc-region is a human immunoglobulin Fc-region with a mutation of the amino acid residue at position 329 and at least one further mutation of at least one amino acid selected from the group comprising amino acid residues at position 228, 233, 234, 235, 236, 237, 297, 318, 320, 322 and 331 to a different residue, wherein the residues in the Fc-region are numbered according to the EU index of Kabat.
17. The fusion polypeptide according to any one of items 1 to 16, characterized in that the human immunoglobulin Fc-region has a reduced affinity to the human FcγRIIIA and/or FcγRIIA and/or FcγRI compared to a human immunoglobulin Fc-region fusion polypeptide comprising a wild-type human immunoglobulin IgG Fc-region.
18. The fusion polypeptide according to any one of items 1 to 17, characterized in that the human immunoglobulin Fc-region comprises at least one mutation selected from the group comprising S228P, E233P, L234A, L235A, L235E, N297A, N297D, P329G and P331S.
19. The fusion polypeptide according to any one of items 1 to 18, characterized in that the human immunoglobulin Fc-region comprises the mutations L234A, L235A and P329G if the Fc-region is of human IgG1 isotype or the mutations S228P, L235E and P329G if the Fc-region is of human IgG4 isotype.
20. The fusion polypeptide according to any one of items 1 to 19, characterized in that thrombocyte aggregation induced by the human immunoglobulin Fc-region is reduced compared to the thrombocyte aggregation induced by a wild-type human immunoglobulin Fc-region.
21. The fusion polypeptide according to any one of items 1 to 20, characterized in comprising one or two incretin receptor ligand polypeptides.
22. The fusion polypeptide according to item 21, characterized in that each of the incretin receptor ligand polypeptides is conjugated to the N-terminus of one polypeptide chain of the human immunoglobulin Fc-region.
23. The fusion polypeptide according to item 21, characterized in that each of the incretin receptor ligand polypeptides is conjugated to the C-terminus of one polypeptide chain of the human immunoglobulin Fc-region.
24. The fusion polypeptide according to any one of items 1 to 23, characterized in that the incretin receptor ligand polypeptides are selected independently from each other from GIP, GLP-1, exendin-3, exendin-4, dual GIP-GLP-1 agonists, triple GIP-GLP-1-glucagon receptor agonists, chimeric GIP/GLP agonists, and precursors, derivatives, or functional fragments thereof.
25. The fusion polypeptide according to any one of items 1 to 24, characterized in that the human immunoglobulin Fc-region comprises an amino acid sequence selected from the group consisting of SEQ ID NOs: 42-56.
26. The fusion polypeptide according to any one of items 1 to 25, characterized in that the fusion polypeptide comprises a linker between the human immunoglobulin Fc-region and the incretin receptor ligand polypeptide, wherein the linker comprises an amino acid sequence selected from the group consisting of SEQ ID NOs: 57-69 and 82-94.
27. The fusion polypeptide according to any one of items 1 to 26, characterized in that the incretin receptor ligand polypeptide is derived from GLP-1(7-37) (HAEGTFTSDVSSYLEGQAAKEFIAWLVKGRG, SEQ ID NO: 01), wherein at least one amino acid residue is conjugated to a lipid or is changed to a non-naturally occurring amino acid residue conjugated to a lipid and wherein the derived polypeptide has incretin receptor ligand activity.
28. The fusion polypeptide according to any one of items 1 to 26, characterized in that the incretin receptor ligand polypeptide is derived from GLP-1(7-36) (HAEGTFTSDVSSYLEGQAAKEFIAWLVKGR, SEQ ID NO: 02), wherein at least one amino acid residue is conjugated to a lipid or is changed to a non-naturally occurring amino acid residue conjugated to a lipid and wherein the derived polypeptide has incretin receptor ligand activity.
29. The fusion polypeptide according to any one of items 1 to 26, characterized in that the incretin receptor ligand polypeptide is derived from exendin-3 (HSDGTFTSDLSKQMEEEAVRLFIEWLKNGG PSSGAPPPS, SEQ ID NO: 03), wherein at least one amino acid residue is conjugated to a lipid or is changed to a non-naturally occurring amino acid residue conjugated to a lipid and wherein the derived polypeptide has incretin receptor ligand activity.

30. The fusion polypeptide according to any one of items 1 to 26, characterized in that the incretin receptor ligand polypeptide is derived from exendin-4 (HGEGTFTSDL-SKQMEEEAVRLFIEWLKNGGPSSGAPPPS, SEQ ID NO: 04), wherein at least one amino acid residue is conjugated to a lipid or is changed to a non-naturally occurring amino acid residue conjugated to a lipid and wherein the derived polypeptide has incretin receptor ligand activity.

31. The fusion polypeptide according to any one of items 1 to 26, characterized in that the incretin receptor ligand polypeptide is derived from any one of SEQ ID NOs: 01-04, wherein 1 to 10 (e.g., 1, 2, 3, 4, 5, 6, 7, 8, 9, 10) amino acid modifications relative to SEQ ID NO: 01-04 have been made, wherein at least one amino acid residue is conjugated to a lipid or is changed to a non-naturally occurring amino acid residue conjugated to a lipid and wherein the derived polypeptide has incretin receptor ligand activity.

32. The fusion polypeptide according to any one of items 1 to 26, characterized in that the incretin receptor ligand polypeptide is derived from exendin-4(1-31) desGlu(17) Tyr(32) (HGEGTFTSDLSKQMEEAVRLFIEWLKNG-GPY, SEQ ID NO: 05), wherein at least one amino acid residue is conjugated to a lipid or is changed to a non-naturally occurring amino acid residue conjugated to a lipid and wherein the derived polypeptide has incretin receptor ligand activity.

33. The fusion polypeptide according to any one of items 1 to 26, characterized in that the incretin receptor ligand polypeptide is derived from exendin-4(1-30) Tyr(31) (HGEGTFTSDLSKQMEEEAVRLFIEWLKNGGY, SEQ ID NO: 06), wherein at least one amino acid residue is conjugated to a lipid or is changed to a non-naturally occurring amino acid residue conjugated to a lipid and wherein the derived polypeptide has incretin receptor ligand activity.

34. The fusion polypeptide according to any one of items 1 to 26, characterized in that the incretin receptor ligand polypeptide is derived from exendin-4(9-39) (DL-SKQMEEEAVRLFIEWLKNGGPSSGAPPPS, SEQ ID NO: 07), wherein at least one amino acid residue is conjugated to a lipid or is changed to a non-naturally occurring amino acid residue conjugated to a lipid and wherein the derived polypeptide has incretin receptor ligand activity.

35. The fusion polypeptide according to any one of items 1 to 26, characterized in that the incretin receptor ligand polypeptide is derived from the amino acid sequence SYLEGQAAKEFIAWLVXGR (SEQ ID NO: 08) with X=K or R, wherein at least one amino acid residue is conjugated to a lipid or is changed to a non-naturally occurring amino acid residue conjugated to a lipid and wherein the derived polypeptide has incretin receptor ligand activity.

36. The fusion polypeptide according to any one of items 1 to 26, characterized in that the incretin receptor ligand polypeptide is derived from the amino acid sequence SSYLEGQAAKEFIAWLVXGR (SEQ ID NO: 09) with X=K or R, wherein at least one amino acid residue is conjugated to a lipid or is changed to a non-naturally occurring amino acid residue conjugated to a lipid and wherein the derived polypeptide has incretin receptor ligand activity.

37. The fusion polypeptide according to any one of items 1 to 26, characterized in that the incretin receptor ligand polypeptide is derived from the amino acid sequence VSSYLEGQAAKEFIAWLVXGR (SEQ ID NO: 10) with X=K or R, wherein at least one amino acid residue is conjugated to a lipid or is changed to a non-naturally occurring amino acid residue conjugated to a lipid and wherein the derived polypeptide has incretin receptor ligand activity.

38. The fusion polypeptide according to any one of items 1 to 26, characterized in that the incretin receptor ligand polypeptide is derived from the amino acid sequence DVSSYLEGQAAKEFIAWLVXGR (SEQ ID NO: 11) with X=K or R, wherein at least one amino acid residue is conjugated to a lipid or is changed to a non-naturally occurring amino acid residue conjugated to a lipid and wherein the derived polypeptide has incretin receptor ligand activity.

39. The fusion polypeptide according to any one of items 1 to 26, characterized in that the incretin receptor ligand polypeptide is derived from the amino acid sequence SDVSSYLEGQAAKEFIAWLVXGR (SEQ ID NO: 12) with X=K or R, wherein at least one amino acid residue is conjugated to a lipid or is changed to a non-naturally occurring amino acid residue conjugated to a lipid and wherein the derived polypeptide has incretin receptor ligand activity.

40. The fusion polypeptide according to any one of items 1 to 26, characterized in that the incretin receptor ligand polypeptide is derived from the amino acid sequence TSDVSSYLEGQAAKEFIAWLVXGR (SEQ ID NO: 13) with X=K or R, wherein at least one amino acid residue is conjugated to a lipid or is changed to a non-naturally occurring amino acid residue conjugated to a lipid and wherein the derived polypeptide has incretin receptor ligand activity.

41. The fusion polypeptide according to any one of items 1 to 26, characterized in that the incretin receptor ligand polypeptide is derived from the amino acid sequence FTSDVSSYLEGQAAKEFIAWLVXGR (SEQ ID NO: 14) with X=K or R, wherein at least one amino acid residue is conjugated to a lipid or is changed to a non-naturally occurring amino acid residue conjugated to a lipid and wherein the derived polypeptide has incretin receptor ligand activity.

42. The fusion polypeptide according to any one of items 1 to 26, characterized in that the incretin receptor ligand polypeptide is derived from the amino acid sequence TFTSDVSSYLEGQAAKEFIAWLVXGR (SEQ ID NO: 15) with X=K or R, wherein at least one amino acid residue is conjugated to a lipid or is changed to a non-naturally occurring amino acid residue conjugated to a lipid and wherein the derived polypeptide has incretin receptor ligand activity.

43. The fusion polypeptide according to any one of items 1 to 26, characterized in that the incretin receptor ligand polypeptide is derived from the amino acid sequence GTFTSDVSSYLEGQAAKEFIAWLVXGR (SEQ ID NO: 16) with X=K or R, wherein at least one amino acid residue is conjugated to a lipid or is changed to a non-naturally occurring amino acid residue conjugated to a lipid and wherein the derived polypeptide has incretin receptor ligand activity.

44. The fusion polypeptide according to any one of items 1 to 26, characterized in that the incretin receptor ligand polypeptide is derived from the amino acid sequence EGTFTSDVSSYLEGQAAKEFIAWLVXGR (SEQ ID NO: 17) with X=K or R, wherein at least one amino acid residue is conjugated to a lipid or is changed to a non-naturally occurring amino acid residue conjugated to a lipid and wherein the derived polypeptide has incretin receptor ligand activity.

45. The fusion polypeptide according to any one of items 1 to 26, characterized in that the incretin receptor ligand polypeptide is derived from the amino acid sequence AEGTFTSDVSSYLEGQAAKEFIAWLVXGR (SEQ ID NO: 18) with X=K or R, wherein at least one amino acid residue is conjugated to a lipid or is changed to a non-naturally occurring amino acid residue conjugated to a lipid and wherein the derived polypeptide has incretin receptor ligand activity.

46. The fusion polypeptide according to any one of items 1 to 26, characterized in that the incretin receptor ligand polypeptide is derived from the amino acid sequence HAEGTFTSDVSSYLEGQAAKEFIAWLVXGR (SEQ ID NO: 19) with X=K or R, wherein at least one amino acid residue is conjugated to a lipid or is changed to a non-naturally occurring amino acid residue conjugated to a lipid and wherein the derived polypeptide has incretin receptor ligand activity.

47. The fusion polypeptide according to any one of items 1 to 26, characterized in that the incretin receptor ligand polypeptide is derived from the amino acid sequence HDAEGTFTSDVSSYLEGQAAKEFIAWLVXGR (SEQ ID NO: 20) with X=K or R, wherein at least one amino acid residue is conjugated to a lipid or is changed to a non-naturally occurring amino acid residue conjugated to a lipid and wherein the derived polypeptide has incretin receptor ligand activity.

48. The fusion polypeptide according to any one of items 1 to 26, characterized in that the incretin receptor ligand polypeptide is derived from the amino acid sequence HAEGTFTSDVSSYLEGQAAKEFIAWLVKGRPSS-GAPPPS (SEQ ID NO: 21) (hybrid GLP-1/exendin polypeptide), wherein at least one amino acid residue is conjugated to a lipid or is changed to a non-naturally occurring amino acid residue conjugated to a lipid and wherein the derived polypeptide has incretin receptor ligand activity.

49. The fusion polypeptide according to any one of items 1 to 26, characterized in that the incretin receptor ligand polypeptide is derived from the amino acid sequence HDEFERHAEGTFTSDVSSYLEGQAAKEFIAWLVK-GRK (SEQ ID NO: 22), wherein at least one amino acid residue is conjugated to a lipid or is changed to a non-naturally occurring amino acid residue conjugated to a lipid and wherein the derived polypeptide has incretin receptor ligand activity.

50. The fusion polypeptide according to any one of items 1 to 26, characterized in that the incretin receptor ligand polypeptide is derived from the amino acid sequence HAEGTFTSDVSSYLEGQAAKEFIAWLVKGRK (SEQ ID NO: 23), wherein at least one amino acid residue is conjugated to a lipid or is changed to a non-naturally occurring amino acid residue conjugated to a lipid and wherein the derived polypeptide has incretin receptor ligand activity.

51. The fusion polypeptide according to any one of items 1 to 26, characterized in that the incretin receptor ligand polypeptide is derived from the amino acid sequence HGEGTFTSDLSKQMEEEAVRLFIEWLKNGGPSS-GAPPPSK (SEQ ID NO: 24), wherein at least one amino acid residue is conjugated to a lipid or is changed to a non-naturally occurring amino acid residue conjugated to a lipid and wherein the derived polypeptide has incretin receptor ligand activity.

52. The fusion polypeptide according to any one of items 1 to 26, characterized in that the incretin receptor ligand polypeptide is derived from the amino acid sequence HSDGTFTSDLSKQMEEEAVRLFIEWLKNGGPSS-GAPPPSK (SEQ ID NO: 25), wherein at least one amino acid residue is conjugated to a lipid or is changed to a non-naturally occurring amino acid residue conjugated to a lipid and wherein the derived polypeptide has incretin receptor ligand activity.

53. The fusion polypeptide according to any one of items 1 to 26, characterized in that the incretin receptor ligand polypeptide is derived from the amino acid sequence HGEGTFTSDLSKEMEEEVRLFIEWLKNGGPY (SEQ ID NO: 26), wherein at least one amino acid residue is conjugated to a lipid or is changed to a non-naturally occurring amino acid residue conjugated to a lipid and wherein the derived polypeptide has incretin receptor ligand activity.

54. The fusion polypeptide according to any one of items 1 to 26, characterized in that the incretin receptor ligand polypeptide is derived from the amino acid sequence HGEGTFTSDLSKEMEEEVRLFIEWLKNGGY (SEQ ID NO: 27), wherein at least one amino acid residue is conjugated to a lipid or is changed to a non-naturally occurring amino acid residue conjugated to a lipid and wherein the derived polypeptide has incretin receptor ligand activity.

55. The fusion polypeptide according to any one of items 1 to 26, characterized in that the incretin receptor ligand polypeptide is derived from the amino acid sequence DLSKQMEEEAVRLFIEWLKGGPSSGPPPS (SEQ ID NO: 28), wherein at least one amino acid residue is conjugated to a lipid or is changed to a non-naturally occurring amino acid residue conjugated to a lipid and wherein the derived polypeptide has incretin receptor ligand activity.

56. The fusion polypeptide according to any one of items 1 to 26, characterized in that the incretin receptor ligand polypeptide is derived from native glucagon (SEQ ID NO: 76) with 1 to 10 (e.g., 1, 2, 3, 4, 5, 6, 7, 8, 9, 10) amino acid modifications relative to SEQ ID NO: 76, wherein at least one amino acid residue is conjugated to a lipid or is changed to a non-naturally occurring amino acid residue conjugated to a lipid and wherein the derived polypeptide has incretin receptor ligand activity.

57. The fusion polypeptide according to any one of items 1 to 26, characterized in that the incretin receptor ligand polypeptide is derived from GLP-1 (SEQ ID NO: 1 or 2) with 1 to 10 (e.g., 1, 2, 3, 4, 5, 6, 7, 8, 9, 10) amino acid modifications relative to SEQ ID NO: 1 or 2, wherein at least one amino acid residue is conjugated to a lipid or is changed to a non-naturally occurring amino acid residue conjugated to a lipid and wherein the derived polypeptide has incretin receptor ligand activity.

58. The fusion polypeptide according to any one of items 1 to 26, characterized in that the incretin receptor ligand polypeptide is derived from GIP (SEQ ID NO: 77) with 1 to 10 (e.g., 1, 2, 3, 4, 5, 6, 7, 8, 9, 10) amino acid modifications relative to SEQ ID NO: 77, wherein at least one amino acid residue is conjugated to a lipid or is changed to a non-naturally occurring amino acid residue conjugated to a lipid and wherein the derived polypeptide has incretin receptor ligand activity.

59. The fusion polypeptide according to any one of items 1 to 26, characterized in that the incretin receptor ligand polypeptide is derived from exendin-3 or -4 (SEQ ID NO: 3 or 4) with 1 to 10 (e.g., 1, 2, 3, 4, 5, 6, 7, 8, 9, 10) amino acid modifications relative to SEQ ID NO: 3 or 4, wherein at least one amino acid residue is conjugated to a lipid or is changed to a non-naturally occurring amino acid residue conjugated to a lipid and wherein the derived polypeptide has incretin receptor ligand activity.

60. The fusion polypeptide according to any one of items 1 to 26, characterized in that the incretin receptor ligand polypeptide is derived from glucagon (SEQ ID NO: 76) wherein the analog comprises SEQ ID NO: 76 with (a) an amino acid modification at position 1 that confers GIP agonist activity, (b) a modification which stabilizes the alpha helix structure of the C-terminal portion (amino acids 12-29) of the analog, and (c) optionally, 1 to 10 (e.g., 1, 2, 3, 4, 5, 6, 7, 8, 9, 10) further amino acid modifications relative to SEQ ID NO: 76, wherein at least one amino acid residue is conjugated to a lipid or is changed to a non-naturally occurring amino acid residue conjugated to a lipid and wherein the derived polypeptide has incretin receptor ligand activity.

61. The fusion polypeptide according to any one of items 1 to 26, characterized in that the incretin receptor ligand polypeptide is or comprises the amino acid sequence YXEGTFTSDYSIYLDKQAAXEFVCWLLAGGPSS-GAPPPSK (SEQ ID NO: 29) with X=aib, wherein at least one amino acid residue is conjugated to a lipid or is changed to a non-naturally occurring amino acid residue conjugated to a lipid and wherein the derived polypeptide has incretin receptor ligand activity.

62. The fusion polypeptide according to any one of items 1 to 26, characterized in that the incretin receptor ligand polypeptide is or comprises the amino acid sequence YXEGTFTSDYSIYLDKQAAXEFVNWLLAGGPSS-GAPPPSK (SEQ ID NO: 30) with X=aib, wherein at least one amino acid residue is conjugated to a lipid or is changed to a non-naturally occurring amino acid residue conjugated to a lipid and wherein the derived polypeptide has incretin receptor ligand activity.

63. The fusion polypeptide according to any one of items 1 to 26, characterized in that the incretin receptor ligand polypeptide is or comprises the amino acid sequence YXEGTFTSDYSIYLDKQAAXEFVAWLLAGGPSS-GAPPPSK (SEQ ID NO: 31) with X=aib, wherein at least one amino acid residue is conjugated to a lipid or is changed to a non-naturally occurring amino acid residue conjugated to a lipid and wherein the derived polypeptide has incretin receptor ligand activity.

64. The fusion polypeptide according to any one of items 1 to 26, characterized in that the incretin receptor ligand polypeptide is or comprises the amino acid sequence YXEGTFTSDYSIYLDKQAAXEFVNWLLAGGG (SEQ ID NO: 32) with X=aib, wherein at least one amino acid residue is conjugated to a lipid or is changed to a non-naturally occurring amino acid residue conjugated to a lipid and wherein the derived polypeptide has incretin receptor ligand activity.

65. The fusion polypeptide according to any one of items 1 to 26, characterized in that the incretin receptor ligand polypeptide is or comprises the amino acid sequence YXEGTFTSDYSIYLDKQAAXEFVAWLLAGG G (SEQ ID NO: 33) with X=aib, wherein at least one amino acid residue is conjugated to a lipid or is changed to a non-naturally occurring amino acid residue conjugated to a lipid and wherein the derived polypeptide has incretin receptor ligand activity.

66. The fusion polypeptide according to any one of items 1 to 26, characterized in that the incretin receptor ligand polypeptide is or comprises the amino acid sequence YXEGTFTSDYSIYLDEQAAKEFVNWLLAGGPSS-GAPPPSC (SEQ ID NO: 34) with X=aib, wherein at least one amino acid residue is conjugated to a lipid or is changed to a non-naturally occurring amino acid residue conjugated to a lipid and wherein the derived polypeptide has incretin receptor ligand activity.

67. The fusion polypeptide according to any one of items 1 to 26, characterized in that the incretin receptor ligand polypeptide is or comprises the amino acid sequence YXEGTFTSDYSIYLDKQAAXEFVNWLLAGGPSS-GAPPPSC (SEQ ID NO: 35) with X=aib, wherein at least one amino acid residue is conjugated to a lipid or is changed to a non-naturally occurring amino acid residue conjugated to a lipid and wherein the derived polypeptide has incretin receptor ligand activity.

68. The fusion polypeptide according to any one of items 1 to 26, characterized in that the incretin receptor ligand polypeptide is or comprises the amino acid sequence YXQGTFTSDYSIYLDKQAAXEFVNWLLAGGPSS-GAPPPSK (SEQ ID NO: 36) with X=aib, wherein at least one amino acid residue is conjugated to a lipid or is changed to a non-naturally occurring amino acid residue conjugated to a lipid and wherein the derived polypeptide has incretin receptor ligand activity.

69. The fusion polypeptide according to any one of items 1 to 26, characterized in that the incretin receptor ligand polypeptide is or comprises the amino acid sequence YXQGTFTSDYSIYLDEQAAKEFVNWLLAGGPSS-GAPPPSC (SEQ ID NO: 37) with X=aib and with a lactam ring between the side chains of residues 16 and 20, wherein at least one amino acid residue is conjugated to a lipid or is changed to a non-naturally occurring amino acid residue conjugated to a lipid and wherein the derived polypeptide has incretin receptor ligand activity.

70. The fusion polypeptide according to any one of items 1 to 26, characterized in that the incretin receptor ligand polypeptide is or comprises the amino acid sequence YXQGTFISDYSIYLDEQAAKEFVNWLLAGGPSS-GAPPPSC (SEQ ID NO: 38) with X=aib and with a lactam ring between the side chains of residues 16 and 20, wherein at least one amino acid residue is conjugated to a lipid or is changed to a non-naturally occurring amino acid residue conjugated to a lipid and wherein the derived polypeptide has incretin receptor ligand activity.

71. The fusion polypeptide according to any one of items 1 to 26, characterized in that the incretin receptor ligand polypeptide is or comprises the amino acid sequence YXQGTFISDYSIYLDEQAAKEFVCWLLAG (SEQ ID NO: 39) with X=aib and with a lactam ring between the side chains of residues 16 and 20, wherein at least one amino acid residue is conjugated to a lipid or is changed to a non-naturally occurring amino acid residue conjugated to a lipid and wherein the derived polypeptide has incretin receptor ligand activity.

72. A lipidated incretin receptor ligand polypeptide comprising the amino acid sequence of Y-Aib-EGTFTSDK-(γEγE-C16)-SIYLDKQAA-Aib-EFVNWLLAGGPSS-GAPPPS (SEQ ID NO: 120).

73. A lipidated incretin receptor ligand polypeptide comprising the amino acid sequence of desAmino-Tyr-AE-GTFTSDK-(γE-C16)-SKYLDERAAQDFVQWLLEG-GPSSGAPPPS (SEQ ID NO: 121).

74. A lipidated incretin receptor ligand polypeptide comprising the amino acid sequence of Ac-d-YALGTFTSDK-(γE-C16)-SKYLDERAAQDFVQWLLEGGPSSGAP-PPS (SEQ ID NO: 122).

75. A lipidated incretin receptor ligand polypeptide comprising the amino acid sequence of Ac-d-YAVGTFTSDK-(γE-C16)-SKYLDERAAQDFVQWLLEGGPSSGAP-PPS (SEQ ID NO: 123).

76. A lipidated incretin receptor ligand polypeptide comprising the amino acid sequence of Ac-d-HAQGT-FTSDK-(γE-C16)-SKYLDERAAQDFVQWLLEG-GPSSGAPPPS (SEQ ID NO: 124).

77. A lipidated incretin receptor ligand polypeptide comprising the amino acid sequence of Ac-d-YAQGT-FTSDK-(γE-C16)-SKYLDERAAQDFVQWLLEG-GPSSGAPPPS (SEQ ID NO: 125).

78. A lipidated incretin receptor ligand polypeptide comprising the amino acid sequence of Y-Aib-EGTFTSDK-(γE-γE-C16)-SIYLDKQAA-Aib-EFVNWLLAGGPSS-GAPPPSC-(S—CH2-CO)-LPETGGSGS (SEQ ID NO: 109).

79. A lipidated incretin receptor ligand polypeptide comprising the amino acid sequence of desAminoTyr-AEGT-FTSDK-(γE-C16)SKYLDERAAQDFVQWLLEGGPSS-GAPPPSC-(S—CH2-CO)-GGGLPETGGSGS (SEQ ID NO: 110).

80. A lipidated incretin receptor ligand polypeptide comprising the amino acid sequence of Ac-d-YALGTFTSDK (γE-C16)SKYLDERAAQDFVQWLLEGGPSSGAP-PPSC-(S—CH2-CO)-GGGLPETGGSGS (SEQ ID NO: 111).

81. A lipidated incretin receptor ligand polypeptide comprising the amino acid sequence of Ac-d-YAVGTFTSDK (γE-C16)SKYLDERAAQDFVQWLLEGGPSSGAP-PPSC-(S—CH2-CO)-GGGLPETGGSGS (SEQ ID NO: 112).

82. A lipidated incretin receptor ligand polypeptide comprising the amino acid sequence of Ac-d-HAQGTFTSDK (γE-C16)SKYLDERAAQDFVQWLLEGGPSSGAP-PPSC-(S—CH2-CO)-GGGLPETGGSGS (SEQ ID NO: 113).

83. A lipidated incretin receptor ligand polypeptide comprising the amino acid sequence of Ac-d-YAQGTFTSDK (γE-C16)SKYLDERAAQDFVQWLLEGGPSSGAP-PPSC-(S—CH2-CO)-GGGLPETGGSGS (SEQ ID NO: 114).

84. A lipidated incretin receptor ligand polypeptide comprising the amino acid sequence of Ac-d-HAQGTFTSDK (γE-C16)SKYLDERAAQDFVQWLLGGGL-PETGGSGS (SEQ ID NO: 115).

85. A lipidated incretin receptor ligand polypeptide comprising the amino acid sequence of Ac-d-YALGTFTSDK (γE-C16)SKYLDERAAQDFVQWLLEGGPSSGAP-PPSGGGLPETGGSGS (SEQ ID NO: 116).

86. A fusion polypeptide comprising
one, two, three or four incretin receptor ligand polypeptides, and
one human immunoglobulin Fc-region,
wherein at least one of the incretin receptor ligand polypeptides is selected from the group of lipidated incretin receptor ligand polypeptides of SEQ ID NOs: 120 to 125,
wherein the human immunoglobulin Fc-region is selected from group of human immunoglobulin Fc-region of SEQ ID NOs: 42 to 53,
wherein each of the one, two, three or four incretin receptor ligand polypeptides is covalently conjugated independently of each other either directly or via a linker peptide to a terminus of the human immunoglobulin Fc-region, whereby the linker peptide is selected if present from the group comprising (GGS)n, wherein n=1-4 (SEQ ID NOs: 82-84), Gn, wherein n=2-6 (SEQ ID NOs: 85-87), (GGGS)n, wherein n=1-6 (SEQ ID NOs: 57-60, 88 and 89), (GGGGS)m, wherein m=1-6 (SEQ ID NOs: 61-64, 90 and 91), and (GGGGGS)o, wherein o=1-6 (SEQ ID NOs: 65-67 and 92-94), and
wherein each of the one, two, three or four incretin receptor ligand polypeptides is covalently conjugated by a peptide bond to a terminus of the human immunoglobulin Fc-region, whereby to each terminus of the human immunoglobulin Fc-region only a single incretin receptor ligand polypeptide is conjugated.

87. A fusion polypeptide comprising
one or two incretin receptor ligand polypeptides, and
one human immunoglobulin Fc-region,
wherein at least one of the incretin receptor ligand polypeptides is selected from the group of lipidated incretin receptor ligand polypeptides of SEQ ID NOs: 120 to 125,
wherein the human immunoglobulin Fc-region is selected from group of human immunoglobulin Fc-region of SEQ ID NOs: 42 to 53,
wherein each of the one or two incretin receptor ligand polypeptides is covalently conjugated independently of each other either directly or via a linker peptide to a terminus of the human immunoglobulin Fc-region, whereby the linker peptide is selected if present from the group comprising (GGS)n, wherein n=1-4 (SEQ ID NOs: 82-84), Gn, wherein n=2-6 (SEQ ID NOs: 85-87), (GGGS)n, wherein n=1-6 (SEQ ID NOs: 57-60, 88 and 89), (GGGGS)m, wherein m=1-6 (SEQ ID NOs: 61-64, 90 and 91), and (GGGGGS)o, wherein o=1-6 (SEQ ID NOs: 65-67 and 92-94), and
wherein each of the one or two incretin receptor ligand polypeptides is covalently conjugated by a peptide bond to a terminus of the human immunoglobulin Fc-region, whereby to each terminus of the human immunoglobulin Fc-region only a single incretin receptor ligand polypeptide is conjugated.

88. A fusion polypeptide comprising
one or two incretin receptor ligand polypeptides, and
one human immunoglobulin Fc-region,
wherein at least one of the incretin receptor ligand polypeptides is selected from the group of lipidated incretin receptor ligand polypeptides of SEQ ID NOs: 120 to 125,
wherein the human immunoglobulin Fc-region comprises i) two amino acid sequences of SEQ ID NO: 49 or ii) one amino acid sequence of SEQ ID NO: 52 and one amino acid sequence of SEQ ID NO: 53,
wherein each of the one or two, three or four incretin receptor ligand polypeptides is covalently conjugated via a linker peptide to an N-terminus of the human immunoglobulin Fc-region, whereby the linker peptide is selected from the group comprising (GGGS)4 (SEQ ID NO: 58), (GGGGS)3 (SEQ ID NO: 62), and (GGGGGS)o, wherein o=2-3 (SEQ ID NOs: 65-66), and
wherein each of the one or two incretin receptor ligand polypeptides is covalently conjugated by a peptide bond to a terminus of the human immunoglobulin Fc-region, whereby to each terminus of the human immunoglobulin Fc-region only a single incretin receptor ligand polypeptide is conjugated.

89. A pharmaceutical composition comprising a fusion polypeptide according to any one of items 1 to 88.

90. Use of a fusion polypeptide according to any one of items 1 to 88 as a medicament.
91. Use of a fusion polypeptide according to any one of items 1 to 88 for the manufacture of a medicament for the treatment of a disease, wherein it is favorable that the effector function of the fusion polypeptide comprising a variant Fc-region of a wild-type human IgG Fc-region is reduced compared to the effector function induced by a fusion polypeptide comprising a wild-type human IgG Fc-region.
92. Use of a fusion polypeptide conjugate according to any one of items 1 to 88 comprising a variant Fc-region of a wild-type human IgG Fc-region, wherein Pro329 of the wild-type human IgG Fc-region is substituted with glycine, wherein the residues are numbered according to the EU index of Kabat, wherein the fusion polypeptide exhibits a reduced affinity to the human FcγRIIIA and FcγRIIA for down-modulation of ADCC by at least 20% of the ADCC induced by a fusion polypeptide comprising the wild-type human IgG Fc-region, and/or for down-modulation of ADCP.
93. The use according to any one of items 90 to 92, characterized in that the disease is type-2 diabetes
94. The use according to any one of items 90 to 92, characterized in that the disease is obesity.
95. The use according to any one of items 90 to 92, characterized in that the disease is insulin resistance.
96. The use according to any one of items 90 to 92, characterized in that the disease is type-1 diabetes.
97. The use according to any one of items 90 to 92, characterized in that the disease is osteoporosis.
98. The use according to any one of items 90 to 92, characterized in that the disease is steatohepatitis.
99. The use according to any one of items 90 to 92, characterized in that the disease is non-alcoholic fatty liver disease (NAFLD).
100. The use according to any one of items 90 to 92, characterized in that the disease is metabolic syndrome.
101. The use according to any one of items 90 to 92, characterized in that the fusion polypeptide according to any one of items 1 to 88 is administered in combination with a further type-2 diabetes drug.
102. The use according to item 101, characterized in that the further type-2 diabetes drug is insulin.
103. A polypeptide comprising the amino acid sequence of a lipidated incretin receptor ligand polypeptide and LPXTG (SEQ ID NO: 75), wherein X is any amino acid.
104. The polypeptide according to item 103, wherein X is an acidic amino acid.
105. The polypeptide according to any one of items 103 to 104, wherein the acidic amino acid is Glu.
106. The polypeptide according to any one of items 103 to 105, characterized in comprising Gly-Gly or Gly-Gly-Ser or Gly-Gly-Gly, Gly-Gly-Gly-Ser (SEQ ID NO: 88), Gly-Gly-Gly-Gly (SEQ ID NO: 85), or Gly-Gly-Gly-Gly-Ser (SEQ ID NO: 90)C-terminally to LPETG (SEQ ID NO: 74).
107. The polypeptide according to any one of items 103 to 106, characterized in comprising (GGGS)$_n$, wherein n=1-6 (SEQ ID NOs: 57-60, 88 and 89), (GGGGS)$_m$, wherein m=1-6 (SEQ ID NOs: 61-64, 90 and 91), or (GGGGGS)$_o$, wherein o=1-6 (SEQ ID NOs: 65-67 and 92-94).
108. The polypeptide according to any one of items 103 to 107, characterized in comprising any one of SEQ ID NOs: 57-67.
109. The polypeptide according to any one of items 103 to 107, characterized in comprising Gly or Gly-Gly N-terminally to LPXTG (SEQ ID NO: 75).
110. Use of the polypeptide according to any one of items 102 to 109 in the manufacture of a medicament for treating a disease.
111. The use according to item 110, characterized in that the manufacture of the medicament comprises use of sortase A.

EXAMPLES

The following examples are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention.

Example 1

Sortase A Conjugation of Fc-Region and Incretin Receptor Ligand Polypeptide

```
G3-Fc:
                                          (SEQ ID NO: 68)
GGGDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

G4S3-Fc:
                                          (SEQ ID NO: 69)
GGGGSGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPGK.

peptide-long24A:
                                          (SEQ ID NO: 70)
Y-Aib-EGTFTSDYSIYLDKQAA-Aib-EFVAWLLAGGPSSGAPPPSKLP ETGGSGS-amide peptide-short24A:
                                          (SEQ ID NO: 71)
Y-Aib-EGTFTSDYSIYLDKQAA-Aib-EFVAWLLAGGGLPETGGSGSamide peptide-long24N:
                                          (SEQ ID NO: 118)
Y-Aib-EGTFTSDYSIYLDKQAA-Aib-EFVNWLLAGGPSSGAPPPSKLP ETGGSGS-amide peptide-short24N:
                                          (SEQ ID NO: 119)
Y-Aib-EGTFTSDYSIYLDKQAA-Aib-EFVNWLLAGGGLPETGGSGSamide
```

For the sortase-mediated transpeptidation reaction, N-terminally truncated *Staphylococcus aureus* Sortase A was used ($\Delta_{1-59}$). The reaction was performed in a buffer containing 50 mM Tris-HCl, 150 mM NaCl, 5 mM CaCl, pH 7.5 (Sortase-buffer). In the reaction, a chemically synthesized peptide bearing a sortase motif at its C-terminus (LPETGGSGS, SEQ ID NO: 72) and an Fc-region bearing an oligo-glycine motif at its N-terminus were linked, resulting in the connecting sequence peptide-LPETGGG-heavy chain Fc-region. To perform the reaction, all reagents were brought in solution in sortase buffer. In a first step, GGG-Fc and peptide were mixed, and the reaction was started by the following addition of Sortase A. The components were mixed by pipetting or vortexing and incubated at 37° C. for 1 h and 24 h, depending on the peptide. Subsequently, the ligation product was purified directly after the transpeptidation reaction, or the reaction was stopped by freezing of the reaction mixture and storage at −20° C. until purification.

Molar ratio peptide:Fc-region:sortase=8:1:0.8

Results

Both long and short synthetic peptides were coupled via sortase mediated transpeptidation to IgG-Fc-region fragments bearing either a short tri-glycine motif or a longer GGGGSGGGGSGGGGS (SEQ ID NO: 62) sequence at the N-terminus, respectively. Combinations are displayed in Table 1.

TABLE 1

Conjugation of Fc-regions with peptide

| | Fc | peptide | time | temp | conc. SrtA | conc. Fc | conc. peptide |
|---|---|---|---|---|---|---|---|
| 1 | G3-Fc | long24A | 3 h | 37° C. | 0.156 mmol/l | 0.20 mmol/l | 1.56 mmol/l |
| 2 | G3-Fc | short24A | 24 h | 37° C. | 0.156 mmol/l | 0.20 mmol/l | 1.56 mmol/l |
| 3 | G4S3-Fc | long24A | 3 h | 37° C. | 0.156 mmol/l | 0.20 mmol/l | 1.56 mmol/l |
| 4 | G4S3-Fc | short24A | 24 h | 37° C. | 0.156 mmol/l | 0.20 mmol/l | 1.56 mmol/l |

The Fc-region-incretin receptor ligand polypeptide conjugates had the amino acid sequences of SEQ ID NOs: 95-98 for Long Peptide-G3-Fc, Short Peptide-G3-Fc, Long Peptide G4S3-Fc, and Short Peptide G4S3-Fc, respectively.

Analysis of Sortase-Mediated Transpeptidation

Aliquots of the transpeptidation reactions were analyzed by SDS-PAGE. An example is displayed in FIG. 1, showing the results of conjugation of long or short peptide to G3-Fc. From the gel the efficiency of ligation was estimated densitometrically. As shown in Table 2, in the final purified product about 5% of the Fc-region was not conjugated with peptide while around 90% of Fc-region was conjugated with two peptide moieties, as estimated by analytical reversed-phase HPLC.

TABLE 2

Final yields after purification of sortase-mediated transpeptidation of peptides with G3-Fc

| | long peptide | short peptide |
|---|---|---|
| 2x peptide + G3-Fc [%] | 87.00 | 90.75 |
| 1x peptide + G3-Fc [%] | 6.91 | 6.51 |
| non-ligated G3-Fc [%] | 6.09 | 2.73 |

The biological activity of the different conjugates is shown in Table 3.

TABLE 3 in vitro efficacy of peptide-Fc-region fusion molecules generated by sortase-mediated transpeptidation

| Compound | GIP-R $EC_{50}$ [nM] | GLP1-R $EC_{50}$ [nM] |
|---|---|---|
| GIP | 0.058 | — |
| GLP1 | — | 0.005 |
| PEG-peptide-long24A | 7.508 | 3.893 |
| G3Fc only | >600 | >600 |
| peptide-long24A-G3Fc | 1.022 | 0.263 |
| peptide-short24A-G3Fc | 1.921 | 0.697 |

Example 2

Cyclic AMP Assay

The following materials were used: cAMP Hunter™ CHO-K1 GLP-1 or GIP cell lines (DiscoveRx Corporation), Ham's F-12 (Gibco Cat. #21765), 10% heat inactivated FBS (Gibco Cat #16000), Penicillin/Streptomycin/L-Glutamine (Gibco Cat #10378) and 800 µg/ml G418 (geneticin, Gibco Cat. #10131).

CHO-K1 cells expressing GLP-1 or GIP receptors were suspended in 10 ml assay buffer (Krebs-Ringer bicarbonate buffer (Sigma-Aldrich Cat. # K4002) containing 0.5 mM IBMX (Sigma-Aldrich Cat#17018) and 0.1% BSA (Sigma-Aldrich Cat. # A-2153)) at a cell density of 100,000 cells/ml. The cell suspension (25 µl) was subsequently transferred to a half-area plate (Costar Cat. #3694) and drug solutions (25 µl) were added to the wells at appropriate concentrations. The cells were incubated for 30 min at room temperature on a plate shaker. The cAMP content was determined using the Cisbio "cAMP dynamic kit" following the manufacturer's instructions (Cisbio Bioassays, France). All experiments were performed in duplicates and drugs were tested at least twice (N≥2).

Example 3

Acute DIO Mouse Studies

Male C57Bl/6 mice (age about 7 month; Jackson laboratories (Bar Harbor, Me., USA)) were housed in a temperature and humidity controlled environment with a 12 h light:12 h dark cycle. The mice were given ad libitum access to water and a high fat chow diet (HFD; 58% of dietary kcal as fat with sucrose, Research Diets D12331) and water starting at 8 weeks age, and access was maintained throughout the study. The mice were sorted by body weight and food intake prior to start of the treatment period and housed four animals per cage. Mice were acclimated at least 6 days before use. The mice were dosed once prior to onset of dark cycle with vehicle (s.c.), control (human IgG1-Fc; s.c.) or compounds (20 nmol/kg, s.c. of either peptide-long-G3Fc or peptide-short-G3Fc). Thereafter body weight and food intake monitored daily for 5 days (N=8 mice/group).

Data Analysis:

All data shown are the mean±standard error (s.e.m.). Statistical evaluation of the data was carried out using one-way ANOVA, followed by Dunnett's test to determine where statistically significant differences existed between vehicle and drug treated groups. Differences were considered statistically significant at P<0.05. Data analysis was carried out with GraphPad software (GraphPad Prism).

Figure 2:
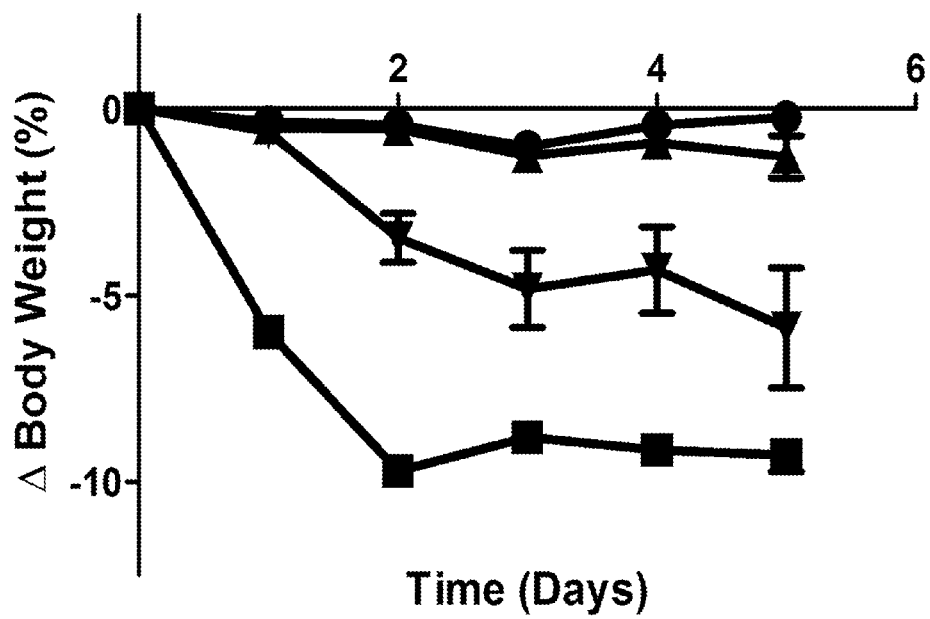
FIG. 2 Course of body weight loss (part a)) and 5 day cumulative food intake (part b)) after a single administration of the compounds peptide-long24A-G3Fc and peptide-short24A-G3Fc (20 nmol/kg, s.c.) in male DIO mice. Vehicle: triangle/1; human IgG1Fc-region control: circle/2; peptide-short24A-G3Fc: inverted triangle/3; peptide-long24A-G3Fc: square/4.
Figure 2:
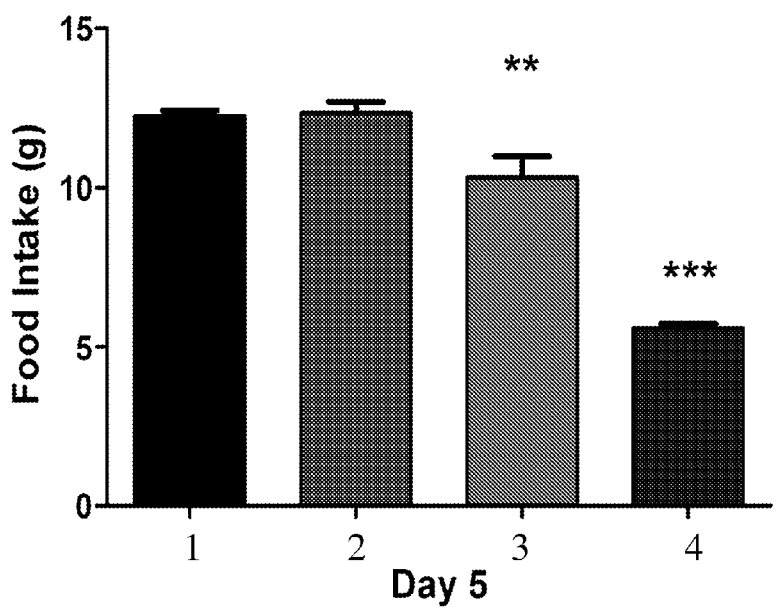

Results:

A single administration of the compounds peptide-long-G3Fc and peptide-short-G3Fc (20 nmol/kg, s.c.) in male DIO mice induced a significant decrease in body weight gain versus vehicle-treated animals and reduced cumulative food intake (FIG. 2).

Example 4

Acute db/db Mouse Studies

Ten week-old male db/db mice (C57BLKS; BKS.Cg-m+/+Lepr (000642); Jackson Laboratories, USA) were housed in a temperature and humidity controlled environment with a 12 h light:12 h dark cycle, and given access to normal chow and water ad libitum (chow, 5% kcal as fat, Harlan 7912). The mice (~42 g) were randomized to various treatment groups based on ad libitum blood glucose levels. The mice were administered vehicle (s.c.), control (s.c.) or the compounds (20 nmol/kg, s.c.) prior to the onset of the dark cycle. The following day, the mice were fasted for 6 h prior to an intraperitoneal glucose challenge test (N=8 mice/group). Blood samples were collected from tail clips following a 6 h fast, for determination of baseline values (t=0 min.), using a handheld FreeStyle Freedom Lite glucose meter (Abbott). The mice were then injected with an intraperitoneal bolus of glucose (1 g/kg; 25% dextrose solution), and additional blood samples were collected at regular intervals (t=15, 30, 60 and 120 min.) for glucose measurement. To analyze the effects of the compounds on intraperitoneal glucose tolerance the area under the curve ($AUC_{0-120\ min}$) for blood glucose excursion was determined using the trapezoid method.

Data Analysis:

All data shown are the mean±standard error (s.e.m.). Statistical evaluation of the data was carried out using one-way ANOVA, followed by Dunnett's test to determine where statistically significant differences existed between vehicle and drug treated groups. Differences were considered statistically significant at P<0.05. Data analysis was carried out with GraphPad software (GraphPad Prism).

Figure 3:
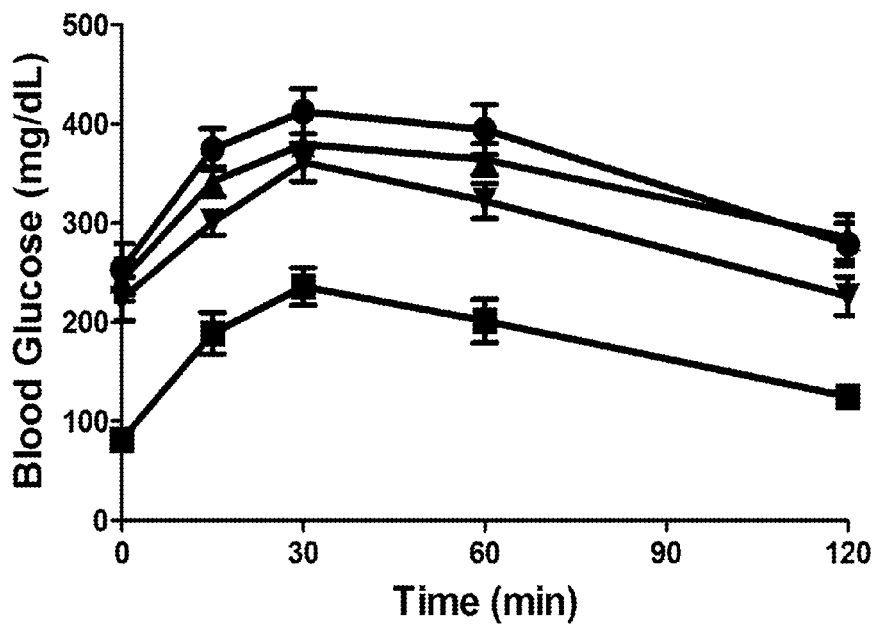
FIG. 3 Course of a glucose excursion in response to an intraperitoneal glucose challenge after administration of the compounds peptide-long-G3Fc and peptide-short24A-G3Fc (20 nmol/kg, s.c.) to male db/db mice (a: ipGTT; b: AUC ipGTT). Vehicle: triangle/1; human IgG1Fc-region control: circle/2; peptide-short24A-G3Fc: inverted triangle/3; peptide-long24A-G3Fc: square/4.
Figure 3:
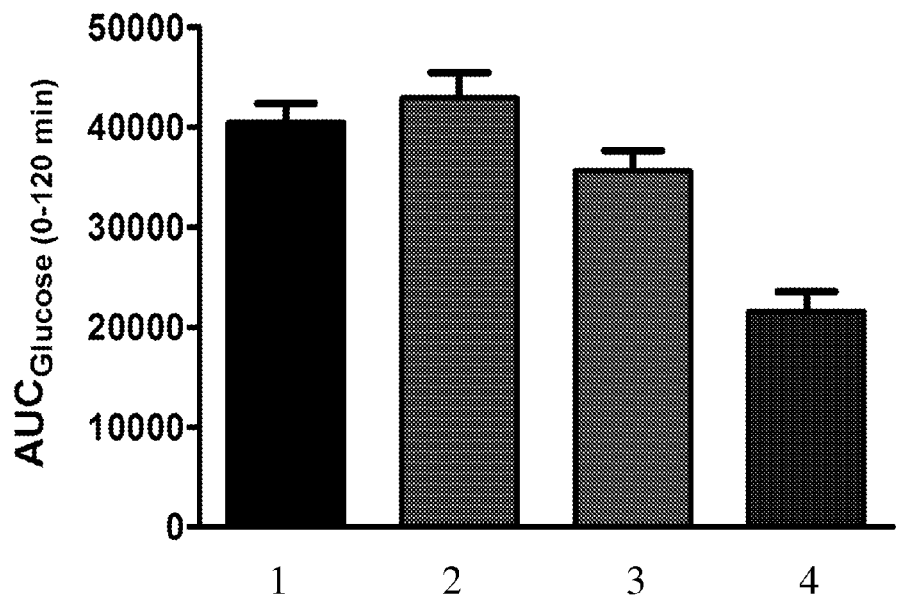
Figure 4:
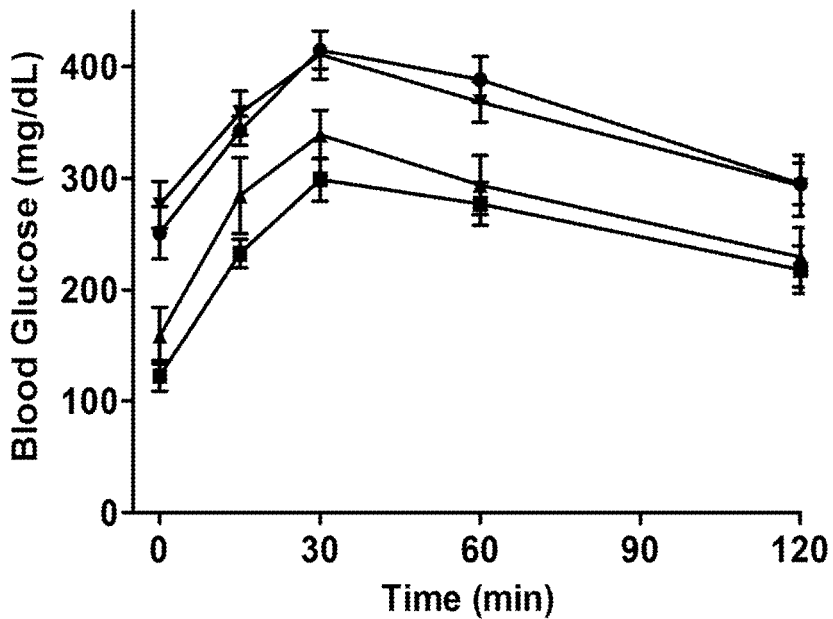
FIG. 4 Dose-dependent course of a glucose excursion in response to an intraperitoneal glucose challenge after administration of the compounds peptide-long-G3Fc and peptide-short-G3Fc (20 nmol/kg, s.c.) to male db/db mice (a: ipGTT; b: AUC ipGTT). Human IgG1Fc-region control: circle/1; peptide-long24A-G3Fc at 1 nmol/kg: inverted triangle/2; peptide-long24A-G3Fc at 3 nmol/kg: triangle/3; peptide-long24A-G3Fc at 10 nmol/kg: square/4.
Figure 4:
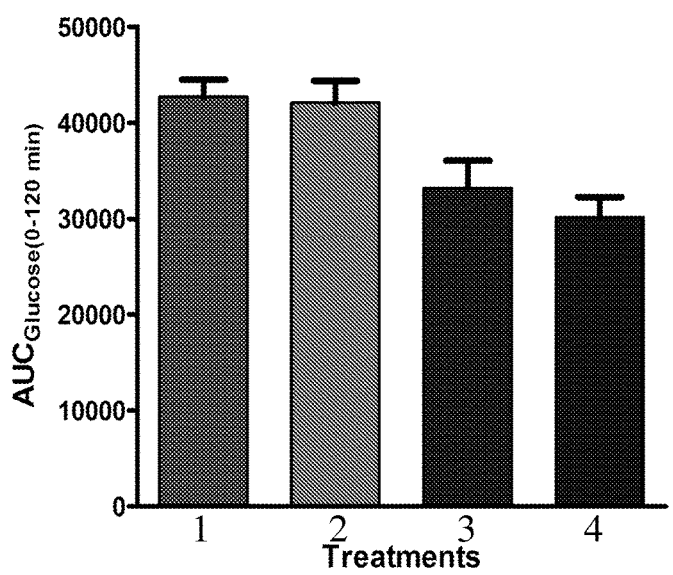

Results:

An acute administration of the compounds peptide-long-G3Fc and peptide-short-G3Fc (20 nmol/kg, s.c.) to male db/db mice significantly decreased glucose excursion in response to an intraperitoneal glucose challenge (ipGTT; AUC ipGTT) (FIG. 3). The effect is dose-dependent (FIG. 4).

Example 5

Composition, expression and purification of recombinant antibody Fc-fragments with Sortase tag Recombinant DNA Techniques Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Reagents

All commercial chemicals, antibodies and kits were used as provided according to the manufacturer's protocol if not stated otherwise.

Expression Plasmids

The Fc-region part encoding gene comprising the human IgG1 Fc-region (hinge, CH2, CH3) and the respective triple G motif or SrtA recognition motif (with or without intervening linker peptide) was assembled by fusing DNA fragments coding for the respective elements.

Amino acid sequence of human IgG1 Fc-region:

```
                                         (SEQ ID NO: 42)
DKTHTCPPCP APELLGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK

GQPREPQVYT LPPSRDELTK NQVSLTCLVK GFYPSDIAVE

WESNGQPENN YKTTPPVLDS DGSFFLYSKL TVDKSRWQQG

NVFSCSVMHE ALHNHYTQKS LSLSPGK.
```

Amino acid sequence of human IgG1 Fc-region with the mutations L234A, L235A and P329G:

```
                                         (SEQ ID NO: 49)
DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALGA PIEKTISKAK

GQPREPQVYT LPPSRDELTK NQVSLTCLVK GFYPSDIAVE

WESNGQPENN YKTTPPVLDS DGSFFLYSKL TVDKSRWQQG

NVFSCSVMHE ALHNHYTQKS LSLSPGK.
```

Amino acid sequence of human IgG1 Fc-region with the mutations L234A, L235A, P329G and hole mutation:

```
                                         (SEQ ID NO: 52)
DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALGA PIEKTISKAK

GQPREPQVCT LPPSRDELTK NQVSLSCAVK GFYPSDIAVE

WESNGQPENN YKTTPPVLDS DGSFFLVSKL TVDKSRWQQG

NVFSCSVMHE ALHNHYTQKS LSLSPGK.
```

Amino acid sequence of human IgG1 Fc-region with the mutations L234A, L235A, P329G and knob mutation:

```
                                         (SEQ ID NO: 53)
DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALGA PIEKTISKAK

GQPREPQVYT LPPCRDELTK NQVSLWCLVK GFYPSDIAVE

WESNGQPENN YKTTPPVLDS DGSFFLYSKL TVDKSRWQQG

NVFSCSVMHE ALHNHYTQKS LSLSPGK.
```

Triple G motif:

```
                  (SEQ ID NO: 99)
            GGG
```

Sortase recognition motif:

```
                     (SEQ ID NO: 72)
          LPETGGSGS
```

Linker peptide:

```
                      (SEQ ID NO: 62)
          GGGGSGGGGSGGGGS.
```

Amino acid sequence of human IgG1 Fc-region with N-terminal triple G motif and the mutations L234A, L235A and P329G:

```
                                         (SEQ ID NO: 117)
GGGDKTHTCP PCPAPEAAGG PSVFLFPPKP KDTLMISRTP

EVTCVVVDVS HEDPEVKFNW YVDGVEVHNA KTKPREEQYN

STYRVVSVLT VLHQDWLNGK EYKCKVSNKA LGAPIEKTIS

KAKGQPREPQ VYTLPPSRDE LTKNQVSLTC LVKGFYPSDI

AVEWESNGQP ENNYKTTPPV LDSDGSFFLY SKLTVDKSRW

QQGNVFSCSV MHEALHNHYT QKSLSLSPGK.
```

The expression vector also comprised an origin of replication from the vector pUC18, which allows replication of this plasmid in *E. coli*, and a beta-lactamase gene which confers ampicillin resistance in *E. coli*.

The transcription unit comprises the following functional elements in 5' to 3' direction:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a nucleic acid encoding the Fc-region part, and
- the bovine growth hormone polyadenylation sequence (BGH pA).

Expression of Antibody Fc-Fragments and Derivatives with Sortase Tag

The antibodies were produced in transiently transfected HEK293 cells (human embryonic kidney cell line 293-derived) cultivated in F17 Medium (Invitrogen Corp.). For transfection of the respective vectors as described in Example 6 "293-Free" Transfection Reagent (Novagen) was used. The antibodies and antibody-blood-brain-barrier shuttle-fusions were expressed from individual expression plasmids. Transfections were performed as specified in the manufacturer's instructions. Recombinant antibody-containing cell culture supernatants were harvested seven days after transfection. Supernatants were stored at reduced temperature (e.g. −80° C.) until purification.

General information regarding the recombinant expression of human immunoglobulins in e.g. HEK293 cells is given in: Meissner, P. et al., Biotechnol. Bioeng. 75 (2001) 197-203.

Purification of Antibody Fc-Regions with Sortase Tag

The recombinant human immunoglobulin Fc-region (or -derivative) was purified from the supernatant in two steps by affinity chromatography using protein A-Sepharose™ affinity chromatography (GE Healthcare, Sweden) and Superdex200 size exclusion chromatography. Briefly, the human immunoglobulin Fc-region (or -derivative) containing clarified culture supernatants were applied on a MabSelectSuRe Protein A (5-50 ml) column equilibrated with PBS buffer (10 mM Na2HPO4, 1 mM KH2PO4, 137 mM NaCl and 2.7 mM KCl, pH 7.4). Unbound proteins were washed out with equilibration buffer. The Fc-regions (or -derivatives) were eluted with 25-50 mM citrate buffer, pH 3.2. The protein containing fractions were neutralized with 0.1 ml 2 M Tris buffer, pH 9.0. Then, the eluted protein fractions were pooled, concentrated with an Amicon Ultra centrifugal filter device (MWCO: 10 K, Millipore) and loaded on a Superdex200 HiLoad 26/60 gel filtration column (GE Healthcare, Sweden) equilibrated with 20 mM histidine, 140 mM NaCl, at pH 6.0. The protein concentration of purified Fc-region (or -derivative) was determined by determining the optical density (OD) at 280 nm with the OD at 320 nm as the background correction, using the molar extinction coefficient calculated on the basis of the amino acid sequence according to Pace et. al., Protein Science 4 (1995) 2411-2423. Monomeric Fc-region fractions were pooled, snap-frozen and stored at −80° C. Part of the samples was provided for subsequent protein analytics and characterization.

The homogeneity of the human immunoglobulin Fc-region (or -derivative) was confirmed by SDS-PAGE in the presence and absence of a reducing agent (5 mM 1,4-dithiothreitol) and staining with Coomassie brilliant blue. The NuPAGE® Pre-Cast gel system (Invitrogen, USA) was used according to the manufacturer's instruction (4-20% Tris-Glycine gels).

Under reducing conditions, polypeptide chains related to the human immunoglobulin Fc-region were identified after SDS-PAGE at apparent molecular sizes analogous to the calculated molecular weights. Expression levels of all constructs were analyzed by protein A. Average protein yields were between 32 mg and 174 mg of purified protein per liter of cell-culture supernatant in such non-optimized transient expression experiments.

Example 6

Synthesis of Lipidated Incretin Receptor Ligand Polypeptide

Abbreviations

Ac: acetyl
Aib: aminoisobutyric acid
Aloc: allyloxycarbonyl
C16: palmitoic acid
DBU: 1,8-diazabicyclo[5.4.0]undec-7-en DCM: dichlormethane
DDE: N-(1-(4,4-dimethyl-2,6-dioxocyclohexylidene) ethyl)
desAminoTyr: 3-(4-hydroxyphenyl)propionic acid
d-y: D-tyrosine
d-h: D-histidine
DIPEA: N,N-diisopropylamine
DMF: N,N-dimethylformamide
Fmoc: 9-fluorenylmethoxycarbonyl
gE: γ-glutamic acid
HBTU: O-benzotriazole-N,N,N',N'-tetramethyl-uronium-hexafluorophosphate
HOTB: N-hydroxybenzotriazole
MeCN: acetonitrile
NMP: N-methylpyrolidone Peptide Synthesis:

Synthesis of peptides was performed on the CS Bio CS136XT Peptide Synthesizer. Synthetic peptides were constructed by sequential addition of amino acid solutions (0.33 mol/L in NMP containing 0.05 mol/L HOBt) to a mixing vessel. Specifically, the synthesis was carried out using COMU/DIPEA activation (4 eq amino acid, 4 eq COMU, 8 eq DIPEA (eq=reaction equivalent)) single couplings. At the end of the coupling step (standard 30 min. at RT) the peptidyl-resin was treated with piperidine-solution (40% in DMF, 1×10 min.+2×5 min.) to remove the N-terminal Fmoc protecting group. The resin was washed repeatedly with dimethylformamide (DMF) and this repetitive cycle was repeated for the desired number of coupling steps. N-capped-peptides were generated by treating the peptidyl-resin with an excess of 18 eq acetic anhydride/DIPEA in DMF for 30 min. at RT. For introducing the bromoacyl group at the N-terminus of the Sortase fragment peptides a mixture of DIPEA in DCM (30%) and activated bromoacetic acid was added to the resin. Activation was achieved by stirring 1.1 eq bromoacetic acid and 1.1 eq DCC in DCM (10 ml for 1.5 g resin) for 10 min. followed by filtration. The obtained clear solution was added to the resin and shaken at RT for one hour.

Acylation and Fmoc-Cleavage in Presence of DDE-Protecting Group & DDE-Cleavage:

To attach the lipidation unit (e.g. palmitoic acid, C16), one or two Dde-Lys(Fmoc)-OH were introduced at the desired position using standard conditions as described above. After quantitative coupling, Fmoc was removed by DBU/DMF 2% treatment (3×3 min. continuous flow, repeatedly washed with DMF, this procedure was repeated 5 times). Coupling of the acylation group was accomplished using coupling conditions as described above. After quantitative coupling of the acylation group the N-terminal Dde protecting group was removed by 20% hydrazine monohydrate (64%) in DMF 2% (5×3 min., continuous flow, repeatedly washed with DMF). The remaining coupling steps were performed as describe above.

Cleavage:

The peptidyl-resin at the end of the entire synthesis was dried by using dichloromethane (DCM), and the peptide was cleaved from the resin with reagent K (TFA/thioanisole/water/phenol/TIS at 82.5/5/5/5/2.5) for two hours at RT and this typically yielded approximately 250 mg (~50% yield) of a crude deprotected peptide. Specifically, the peptidyl-resin (30 mg to 200 mg) was placed in a fritted cartridge then reagent K (~20 ml for 1.2 g resin) was added and the resin was stirred at RT for two hours. After the liquid was filtered off, resin was washed with 5 ml of reagent K and two times 3 ml DCM. The product was precipitated with cold ether (−18° C.). The suspension was centrifuged, the liquid filtered off, and the crude peptide was re-dissolved in water/ACN and freeze dried to obtain ca. 250 mg (~50% yield) crude peptide.

Purification:

Crude peptides were purified using preparative HPLC using a preparative reverse phase column (Dr. Maisch Reprosil Gold 120 C18, 5 µm, 16×150 mm) and eluted using the same mobile phases as on the analytical system (gradient of 5-100% B over 190 minutes at a flow of 1.80 mL/min). HPLC analysis of the obtained fractions lead to the pure fractions which were combined and freeze dried to yield white powder.

Conjugation with Sortase Fragment Peptides:

The purified peptides (containing a C-terminal cysteine) and the sortase fragment peptides (N-terminally bromoacylated) were dissolved in a mixture of water/AcCN (70/30, 1 mL/10 mg peptide). Water (1 mL/30 mg Peptide) and 1000 eq urea were added and the pH of the solution set to 8.4 to 8.5 with buffer (7 M urea, 0.05 M Tris). The reaction mixture was stirred at RT and monitored by HPLC. The final product was isolated via preparative HPLC as described above.

Analytics (HPLC):

Analytical HPLC analyses were conducted under the following conditions: 4.6×150 mm Poroshell 120 SB-C18, 1.0 mL/min, 220 nm UV monitoring. Eluent system: buffer A: 0.1% trifluoroacetic acid/10% acrylonitrile/90% water, buffer B: 0.1% TFA/10% water/90% ACN, gradient 5-100% B over 30 minutes.

It is not mandatory to introduce the Sortase fragment via chemical ligation as described above. The peptides can also be generated linearly to yield the all-amide versions as described for compound 17. These peptides show similar potencies as their thioether-linked analogues.

All other peptides listed below were synthesized as described above.

Compound 1

(SEQ ID NO: 100)
NH2-Y-Aib-EGTFTSDK-(γEγE-C16)-SIYLDKQAA-Aib-

EFVNWLLAGGPSSGAPPPSC-NH2 (cysteine amide)

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, Fmoc-Cys(Trt)-OH, Fmoc-Ala-OH, Fmoc-Trp(Boc)-OH, Fmoc-Asn(Trt)-OH, Fmoc-Val-OH, Fmoc-Phe-OH, Fmoc-Aib-OH, Fmoc-Gln(Trt)-OH, Fmoc-Lys(Boc)-OH, Fmoc-Asp(OtBu)-OH, Fmoc-Tyr(tBu)-OH, Fmoc-Ile-OH, Fmoc-Glu-O(tBu) and palmitoic acid.

MS (M+H$^+$): expected 4671.22; observed 1558.3 (⅓+H)

Compound 2

(SEQ ID NO: 101)
desAmino-Tyr-AEGTFTSDK-(γE-C16)-

SKYLDERAAQDFVQWLLEGGPSSGAPPPSC-NH2 (cysteine amide)

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, Fmoc-Cys(Trt)-OH, Fmoc-Ala-OH, Fmoc-Trp(Boc)-OH, Fmoc-Asn(Trt)-OH, Fmoc-Val-OH, Fmoc-Phe-OH, Fmoc-Gln(Trt)-OH, Fmoc-Lys(Boc)-OH, Fmoc-Asp(OtBu)-OH, Fmoc-Tyr(tBu)-OH, Fmoc-Ile-OH, Fmoc-Glu-O(tBu), 3-(4-Hydroxyphenyl)propionic acid and palmitoic acid.

MS (M+H⁺): expected 4655.3; observed 1552.7 (⅓+H), 1164.8 (¼+H)

Compound 3

(SEQ ID NO: 102)
Ac-d-YALGTFTSDK-(γE-C16)-SKYLDERAAQDFVQWLLEGGPSSGA

PPPSC-NH2 (cysteine amide)

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, Fmoc-Cys(Trt)-OH, Fmoc-Ala-OH, Fmoc-Trp(Boc)-OH, Fmoc-Asn(Trt)-OH, Fmoc-Val-OH, Fmoc-Phe-OH, Fmoc-Gln(Trt)-OH, Fmoc-Lys(Boc)-OH, Fmoc-Asp(OtBu)-OH, Fmoc-Tyr(tBu)-OH, Fmoc-Ile-OH, Fmoc-Glu-O(tBu), Fmoc-dTyr(tBu)-OH and palmitoic acid.

MS (M+H⁺): expected 4655.3; observed 1552.7 (⅓+H), 1164.8 (¼+H)

Compound 4

(SEQ ID NO: 103)
Ac-d-YAVGTFTSDK-(γE-C16)-SKYLDERAAQDFVQWLLEGGPSSG

APPPSC-NH2 (cysteine amide)

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, Fmoc-Cys(Trt)-OH, Fmoc-Ala-OH, Fmoc-Trp(Boc)-OH, Fmoc-Asn(Trt)-OH, Fmoc-Val-OH, Fmoc-Phe-OH, Fmoc-Gln(Trt)-OH, Fmoc-Lys(Boc)-OH, Fmoc-Asp(OtBu)-OH, Fmoc-Tyr(tBu)-OH, Fmoc-Ile-OH, Fmoc-Glu-O(tBu), Fmoc-dTyr(tBu)-OH and palmitoic acid.

MS (M+H⁺): expected 4683.3; observed 1562.1 (⅓+H), 1171.8 (¼+H)

Compound 5

(SEQ ID NO: 104)
Ac-d-HAQGTFTSDK-(γE-C16)-SKYLDERAAQDFVQWLLEGGPSSG

APPPSC-NH2 (cysteine amide)

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, Fmoc-Cys(Trt)-OH, Fmoc-Ala-OH, Fmoc-Trp(Boc)-OH, Fmoc-Asn(Trt)-OH, Fmoc-Val-OH, Fmoc-Phe-OH, Fmoc-Gln(Trt)-OH, Fmoc-Lys(Boc)-OH, Fmoc-Asp(OtBu)-OH, Fmoc-Tyr(tBu)-OH, Fmoc-Ile-OH, Fmoc-Glu-O(tBu), Fmoc-dHis(1-Trt)-OH and palmitoic acid.

MS (M+H⁺): expected 4685.3; observed 1562.8 (⅓+H), 1172.3 (¼+H)

Compound 6

(SEQ ID NO: 105)
Ac-d-YAQGTFTSDK-(γE-C16)-SKYLDERAAQDFVQWLLEGGPSSG

APPPSC-NH2 (cysteine amide)

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, Fmoc-Cys(Trt)-OH, Fmoc-Ala-OH, Fmoc-Trp(Boc)-OH, Fmoc-Asn(Trt)-OH, Fmoc-Val-OH, Fmoc-Phe-OH, Fmoc-Gln(Trt)-OH, Fmoc-Lys(Boc)-OH, Fmoc-Asp(OtBu)-OH, Fmoc-Tyr(tBu)-OH, Fmoc-Ile-OH, Fmoc-Glu-O(tBu), Fmoc-dTyr(tBu)-OH and palmitoic acid.

MS (M+H⁺): expected 4711.3; observed 1571.4 (⅓+H), 1178.8 (¼+H)

Compound 7

(SEQ ID NO: 106)
BrAc-GGGLPETGGSGS-COOH

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, and bromoacetic acid.

MS (M+H⁺): expected 1095.9; observed 1096.9 (M+H)

Compound 8

(SEQ ID NO: 107)
BrAc-LPETGGSGS-COOH

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, and bromoacetic acid.

MS (M+H⁺): expected 924.7; observed 925.7 (M+H)

Compounds 9 to 15 were Generated Via Fragment Ligation as Described Above.

Compound 9

(SEQ ID NO: 108)
NH2-Y-Aib-EGTFTSDK-(γE-γE-C16)-SIYLDKQAA-Aib-

EFVNWLLAGGPSSGAPPPSC-(S—CH2—CO)-GGGLPETGGSGS-COOH

The following fragments were used: Compound 1 and compound 7.

MS (M+H⁺): expected 5686.23; observed 1895.2 (⅓), 1421.6 (¼)

Compound 10

(SEQ ID NO: 109)
NH2-Y-Aib-EGTFTSDK-(γE-γE-C16)-SIYLDKQAA-Aib-

EFVNWLLAGGPSSGAPPPSC-(S—CH2—CO)-LPETGGSGS-COOH

The following fragments were used: Compound 1 and compound 8.

MS (M+H⁺): expected 5672.17; observed 1417.3 (¼), 1134.2 (⅕)

Compound 11

(SEQ ID NO: 110)
desAminoTyr-AEGTFTSDK-(γE-C16)SKYLDERAAQDFVQWLLE

GGPSSGAPPPSC-(S—CH2—CO)-GGGLPETGGSGS-COOH

The following fragments were used: Compound 2 and compound 7.

MS (M+H⁺): expected 5674.13; observed 1891.4 (⅓), 1418.5 (¼)

Compound 12

(SEQ ID NO: 111)
Ac-d-YALGTFTSDK(γE-C16)SKYLDERAAQDFVQWLLEGGPSS

GAPPPSC-(S—CH2—CO)-GGGLPETGGSGS-COOH

The following fragments were used: Compound 3 and compound 7.

MS (M+H⁺): expected 5711.8; observed 1428.7 (¼+4H)
Compound 13

(SEQ ID NO: 112)
Ac-d-YAVGTFTSDK(γE-C16)SKYLDERAAQDFVQWLLEGGPSS

GAPPPSC-(S—CH2—CO)-GGGLPETGGSGS-COOH

The following fragments were used: Compound 4 and compound 7.
MS (M+H⁺): expected 5700.2; observed 1900.1 (⅓)
Compound 14

(SEQ ID NO: 113)
Ac-d-HAQGTFTSDK(γE-C16)SKYLDERAAQDFVQWLLEGGPSS

GAPPPSC-(S—CH2—CO)-GGGLPETGGSGS-COOH

The following fragments were used: Compound 5 and compound 7.
MS (M+H⁺): expected 5703.2; observed 1901.1 (⅓), 1425.8 (¼)
Compound 15

(SEQ ID NO: 114)
Ac-d-YAQGTFTSDK(γE-C16)SKYLDERAAQDFVQWLLEGGPSS

GAPPPSC-(S—CH2—CO)-GGGLPETGGSGS-COOH

The following fragments were used: Compound 6 and compound 7.
MS (M+H⁺): expected 5729.2; observed 1432.3 (¼), 1145.8 (⅕)
Compound 16 and 17 were Synthesized in a Linear Fashion as Described Above.
Compound 16

(SEQ ID NO: 115)
Ac-d-HAQGTFTSDK(γE-C16)SKYLDERAAQDFVQWLLGGGLPETGG

SGS-COOH

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, Fmoc-Cys(Trt)-OH, Fmoc-Ala-OH, Fmoc-Trp(Boc)-OH, Fmoc-Asn(Trt)-OH, Fmoc-Val-OH, Fmoc-Phe-OH, Fmoc-Aib-OH, Fmoc-Gln(Trt)-OH, Fmoc-Lys(Boc)-OH, Fmoc-Asp(OtBu)-OH, Fmoc-Tyr(tBu)-OH, Fmoc-Ile-OH, Fmoc-Glu-O(tBu), Fmoc-dHis(1-Trt)-OH and palmitoic acid.
MS (M+H⁺): expected 4519.3; observed 4519.3
Compound 17

(SEQ ID NO: 116)
Ac-d-YALGTFTSDK(γE-C16)SKYLDERAAQDFVQWLLEGGPSSGAP

PPSGGGLPETGGSGS-COOH

The following amino acids were used: Fmoc-Gly-OH, FMOC-Ser(tBu)-OH, Fmoc-Thr(tBu)-OH, Fmoc-Glu(tBu)-OH, Fmoc-Pro-OH, Fmoc-Leu-OH, Fmoc-Cys(Trt)-OH, Fmoc-Ala-OH, Fmoc-Trp(Boc)-OH, Fmoc-Asn(Trt)-OH, Fmoc-Val-OH, Fmoc-Phe-OH, Fmoc-Aib-OH, Fmoc-Gln(Trt)-OH, Fmoc-Lys(Boc)-OH, Fmoc-Asp(OtBu)-OH, Fmoc-Tyr(tBu)-OH, Fmoc-Ile-OH, Fmoc-Glu-O(tBu), Fmoc-dTyr(tBu)-OH and palmitoic acid.
MS (M+H⁺): expected 5550.7; observed 5550.7

Example 7

Generation of covalent conjugates of human immunoglobulin Fc-regions and lipidated incretin receptor ligand polypeptides using Sortase mediated enzymatic ligation
General Method:

The generation of conjugates of human immunoglobulin Fc-regions with lipidated incretin receptor ligand polypeptides using enzymatic Sortase mediated ligation results in conjugates with defined stoichiometry and it can be assured that the compounds in these conjugates retain their activity (no harsh conditions and danger of denaturation/side reactions). For the generation of conjugates of lipidated incretin receptor ligand polypeptides with the respective human immunoglobulin Fc-region the polypeptide was dissolved in 100% DMF to a final concentration of 16 mM. The Fc-region was brought to a concentration of 10 mg/ml in 50 mM Tris-HCl, 150 mM NaCl, 5 mM $CaCl_2$, pH=7.5. Sortase was brought to a concentration of 17.8 mg/ml in 50 mM Tris-HCl, 150 mM NaCl, 5 mM $CaCl_2$, pH=7.5. Polypeptide, Fc-region and Sortase were mixed in an 8:1:0.8 molar ratio (polypeptide to Fc-region to sortase) adding the Sortase last and by pipetting up and down. Final concentration of DMF in the reaction mixture was below 10% (v/v). The reaction mixture was incubated for 60 to 180 minutes at 37° C. and 350 rpm.

Fc-Region and Compound 9 (=Compound 42)

For the generation of conjugates of compound 9 containing a C-terminal Sortase tag, 46 mg of compound 9 were dissolved in 500 µL DMF to a concentration of 15.6 mM. 50 mg of the Fc-region (N-terminal triple G motif LALAPG Fc-region; SEQ ID NO: 117) was used in a concentration of 17.9 mg/mL (about 0.35 mM) in a buffer composed of 50 mM Tris-HCl, 150 mM NaCl, 5 mM $CaCl_2$, pH=7.5. Compound 9 and the Fc-region of SEQ ID NO: 117 were mixed at an 8:1 molar ratio (polypeptide to Fc-region). 14.1 mg Sortase in a concentration of 17.8 mg/mL (about 0.99 mM) and 1415 µL buffer were added to give a final concentration of the human immunoglobulin Fc-region of 10 mg/mL. The reaction mixture was incubated for three hours at 37° C. and 350 rpm.

Excess peptide, Sortase and uncoupled Fc-region were removed via size exclusion chromatography on a Superdex200 HiLoad 26/60 gel filtration column (GE Healthcare, Sweden) equilibrated with 20 mM histidine, 140 mM NaCl, at pH 6.0

The resulting conjugate (37.5 mg) was analyzed by mass spectrometry. A total of 86% of the detected species was identified as Fc-region coupled to two lipidated incretin receptor ligand polypeptides (avg. mass 61570), 14% was human immunoglobulin Fc-region coupled to one incretin receptor ligand polypeptide (avg. mass 56248).

Fc-Region and Compound 10 (=Compound 45)

For the generation of conjugates of compound 10 9.0 mg of compound 10 were dissolved in a solution containing 10 mg of the Fc-region (N-terminal triple G motif LALAPG Fc-region; SEQ ID NO: 117) in a concentration of 12.1 mg/mL (about 0.24 mM) in a buffer composed of 50 mM Tris-HCl, 150 mM NaCl, 5 mM $CaCl_2$, pH=7.5. The mixture corresponds to an 8:1 molar ratio (polypeptide to Fc-region). Then 2.8 mg Sortase in a concentration of 17.8 mg/mL (about 0.99 mM) was added. The reaction mixture was incubated for three hours at 37° C. and 350 rpm.

Sortase and uncoupled Fc-region were removed via size exclusion chromatography on a Superdex200 HiLoad 16/60 gel filtration column (GE Healthcare, Sweden) equilibrated with 20 mM histidine, 140 mM NaCl, at pH 6.0

The resulting conjugate (8.8 mg) was analyzed by mass spectrometry. A total of 85% of the detected species was identified as Fc-region coupled to two lipidated incretin receptor polypeptides (avg. mass 61227), 14% was Fc-region coupled to one incretin receptor ligand polypeptide (avg. mass 56075).

Fc-Region and Compound 11 (=Compound 74)

For the generation of conjugates of compound 11 9.2 mg of compound 11 were dissolved in 100 µL DMF to a concentration of 15.6 mM. 10 mg of the Fc-region (N-terminal triple G motif LALAPG Fc-region; SEQ ID NO: 117) was used in a concentration of 20.6 mg/mL (about 0.40 mM) in a buffer composed of 50 mM Tris-HCl, 150 mM NaCl, 5 mM $CaCl_2$, pH=7.5. Compound 11 and the Fc-region were mixed at an 8:1 molar ratio (polypeptide to Fc-region). A total of 2.8 mg Sortase in a concentration of 17.8 mg/mL (about 0.99 mM) and 357 µL buffer were added to give a final concentration of 10 mg/mL of the Fc-region in the mixture. The reaction mixture was incubated for three hours at 37° C. and 350 rpm.

Excess peptide, Sortase and uncoupled Fc-region were removed via size exclusion chromatography on a Superdex200 HiLoad 16/60 gel filtration column (GE Healthcare, Sweden) equilibrated with 20 mM histidine, 140 mM NaCl, at pH 6.0

The resulting conjugate (2.1 mg) was analyzed by mass spectrometry. A total of 55% of the detected species was identified as Fc-region conjugated to two incretin receptor ligand polypeptides (avg. mass 61543), 45% was Fc-region coupled to one incretin receptor ligand polypeptide molecule (avg. mass 56233).

Fc-Region and Compound 12 (=Compound 80)

For the generation of conjugates of compound 12 20.0 mg of compound 12 were dissolved in 144 µL DMF to a concentration of 23.5 mM. A total of 28.7 mg of the Fc-region (N-terminal triple G motif LALAPG Fc-region; SEQ ID NO: 117) was used in a concentration of 17.9 mg/mL (about 0.35 mM) in a buffer composed of 50 mM Tris-HCl, 150 mM NaCl, 5 mM $CaCl_2$, 240 mM Sucrose, pH=7.5. Compound 12 and the Fc-region were mixed at a 6:1 molar ratio (polypeptide to Fc-region). Then 8.1 mg Sortase in a concentration of 17.8 mg/mL (about 0.99 mM) and 812 µL of buffer were added to give a final concentration of the Fc-region of 10 mg/mL in the mixture. The reaction mixture was incubated for three hours at 37° C. and 350 rpm.

Excess peptide, Sortase and uncoupled Fc-region were removed via size exclusion chromatography on a Superdex200 HiLoad 26/60 gel filtration column (GE Healthcare, Sweden) equilibrated with 20 mM histidine, 140 mM NaCl, at pH 6.0

The resulting conjugate (24.2 mg) was analyzed by mass spectrometry. A total 84% of the detected species was identified as Fc-region coupled to two incretin receptor ligand polypeptide (avg. mass 61625), 16% was Fc-region coupled to one incretin receptor ligand polypeptide (avg. mass 56274).

Fc-Region and Compound 13 (=Compound 77)

For the generation of conjugates of compound 13 9.3 mg of compound 13 were dissolved in 100 µL DMF to a concentration of 15.6 mM. A total of 10 mg of the Fc-region (N-terminal triple G motif LALAPG Fc-region; SEQ ID NO: 117) was used in a concentration of 15.4 mg/mL (about 0.30 mM) in a buffer composed of 50 mM Tris-HCl, 150 mM NaCl, 5 mM $CaCl_2$, pH=7.5. Compound 13 and the Fc-region were mixed at an 8:1 molar ratio (polypeptide to Fc-region). Then 2.8 mg Sortase in a concentration of 17.8 mg/mL (about 0.99 mM) and 193 µL of buffer were added to give a final concentration of the Fc-region of 10 mg/mL in the mixture. The reaction mixture was incubated for three hours at 37° C. and 350 rpm.

Excess peptide, Sortase and uncoupled Fc-region were removed via size exclusion chromatography on a Superdex200 HiLoad 16/60 gel filtration column (GE Healthcare, Sweden) equilibrated with 20 mM histidine, 140 mM NaCl, at pH 6.0

The resulting conjugate (7.5 mg) was analyzed by mass spectrometry. A total of 90% of the detected species was identified as Fc-region coupled to two lipidated incretin receptor polypeptides (avg. mass 61597), 10% was Fc-region coupled to one lipidated incretin receptor ligand polypeptide (avg. mass 56261).

Fc-Region and Compound 14 (=Compound 808)

For the generation of conjugates of compound 14 4.1 mg of compound 14 were dissolved in 61 µL DMF to a concentration of 11.7 mM. A total of 6.1 mg of the Fc-region (N-terminal triple G motif LALAPG Fc-region; SEQ ID NO: 117) was used in a concentration of 15.4 mg/mL (about 0.30 mM) in a buffer composed of 50 mM Tris-HCl, 150 mM NaCl, 5 mM $CaCl_2$, 240 mM Trehalose pH=7.5. Compound 14 and the Fc-region were mixed at a 6:1 molar ratio (polypeptide to Fc-region). Then 1.7 mg Sortase in a concentration of 17.8 mg/mL (about 0.99 mM) and 117 µL of the buffer were added to give a final concentration of 10 mg/mL of the Fc-region in the mixture. The reaction mixture was incubated for three hours at 37° C. and 350 rpm.

Excess peptide, Sortase and uncoupled Fc-region were removed via size exclusion chromatography on a Superdex200 HiLoad 16/60 gel filtration column (GE Healthcare, Sweden) equilibrated with 20 mM histidine, 140 mM NaCl, at pH 6.0

The resulting conjugate (3.3 mg) was analyzed by mass spectrometry. A total of 81% of the detected species was identified as Fc-region coupled to two lipidated incretin receptor ligand polypeptide (avg. mass 61657), 19% was Fc-region coupled to one lipidated incretin receptor ligand polypeptide (avg. mass 56288).

Fc-Region and Compound 15 (=Compound 809)

For the generation of conjugates of compound 15 3.3 mg of compound 15 were dissolved in 49 µL DMF to a concentration of 11.7 mM. A total of 4.9 mg of the Fc-region (N-terminal triple G motif LALAPG Fc-region; SEQ ID NO: 117) was used in a concentration of 15.4 mg/mL (about 0.30 mM) in a buffer composed of 50 mM Tris-HCl, 150 mM NaCl, 5 mM $CaCl_2$, 240 mM Trehalose pH=7.5. Compound 15 and the Fc-region were mixed at a 6:1 molar ratio (polypeptide to Fc-region). Then 1.4 mg Sortase in a concentration of 17.8 mg/mL (about 0.99 mM) and 95 µL of the buffer were added to give a final concentration of 10 mg/mL of the Fc-region in the mixture. The reaction mixture was incubated for three hours at 37° C. and 350 rpm.

Excess peptide, Sortase and uncoupled Fc-region were removed via size exclusion chromatography on a Superdex200 HiLoad 16/60 gel filtration column (GE Healthcare, Sweden) equilibrated with 20 mM histidine, 140 mM NaCl, at pH 6.0

The resulting conjugate (1.5 mg) was analyzed by mass spectrometry. A total of 78% of the detected species was identified as Fc-region coupled to two lipidated incretin receptor ligand polypeptides (avg. mass 61605), 22% was Fc-region coupled to one lipidated incretin receptor ligand polypeptide (avg. mass 56264).

Example 8

Cyclic AMP (cAMP) Assay: Cell-suspension assay format for stably expressed human GIP-, GLP-1- and GCG-receptors in CHO cells The following materials were used in the cell-based cAMP assay:
- plates: 96-well half-area plates (Costar #3694) for the assay and 96-well non-binding surface plates (Corning #3600) for compound dilution
- tubes for stock solutions: Protein LoBind tubes (Eppendorf #022431081)
- pipet tips: maximum recovery tips (Axygen # TF-100-L-R-S)
- cells: cAMP Hunter™ CHO-K1 GIP (DiscoveRx #95-0146C2), cAMP Hunter™ CHO-K1 GLP-1R (DiscoveRx #95-0062C2), cAMP Hunter™ CHO-K1 GCGR (DiscoveRx #95-0042C2) Gs cell lines from DiscoveRx Corp.
- growth medium: Ham's F-12 (Gibco #21765), 10% Fetal bovine serum (FBS; Gibco 16000), heat-inactivated; 2 mM L-Glutamine, 1% Penicillin/Streptomycin (PSG; Gibco #10378); 500 µg/mL G418 (Geneticin, Gibco #11811-031)
- assay buffer: Krebs-Ringer (Sigma-Aldrich # K4002) pH adjusted (pH=7.3) with sodium bicarbonate (Sigma # S8761), containing 0.5 mM 3-isobutyl-1-methylxanthine (Sigma #17018) and 0.1% bovine serum albumin (Sigma # A2153)
- assay kit: cAMP dynamic 2 kit (Cisbio #62AM4PEC)
- compounds: the stock solutions of compounds were prepared in dimethyl sulphoxide (DMSO; Sigma # D2650) and stored at −20° C.; just prior to the assay, solutions were thawed at room temperature (RT) for 5-10 min., and pre-diluted into assay buffer (1 µM to 60 nM); serial dilutions were performed in assay buffer Cells were grown in T150 flasks to 80% confluency and medium was replaced 24 hours prior to the experiment. On the day of the experiment, the medium was removed and the cell monolayer was washed with 10 mL phosphate buffered saline (PBS) per flask. After removing PBS, the cells were incubated for 5 min at 37° C.) with 5 mL Cell Dissociation solution (Gibco #13151) to dislodge the cells. The flask was gently tapped and the cell suspension was pooled. The cell suspension was centrifuged for 3 min. at 150×g, and supernatant was discarded. The cell pellet was resuspended in assay buffer and cell number determined. Cell concentration was adjusted to 2×10$^5$ cells/mL. A 25 µL cell suspension aliquot was transferred into each well of a 96-well plate using Multi-drop dispenser (5000 cells/well). A 25 µL aliquot of diluted compound was transferred to the cell plate and the cell suspension incubated for 30 min. at RT on a plate shaker (450 rpm). The reaction was stopped by addition of lysis buffer and cAMP generated was determined using the cAMP dynamic 2 kit from Cisbio following the manufacturer's instructions. The time resolved fluorescence signal was determined using an EnVision (PerkinElmer). Cyclic AMP production was calculated based on standard curve run in parallel for every experiment. Data were analyzed using Excel Fit software.

Example 9

Pharmacokinetics
In Life Part
Adult male DIO mice weighing approx. 60 g were obtained from Charles River (Lion, France) and housed in a controlled environment (temperature, humidity, and 12 h light/12 h dark cycle) with access to food and water ad libitum. Rodent studies were conducted with the approval of the local veterinary authority in strict adherence to the Swiss federal regulations on animal protection and to the rules of the Association for Assessment and Accreditation of Laboratory Animal Care International (AAALAC). Mice were administered compounds subcutaneously at 20 nmol/kg as 1 mL/kg injection volume. Blood (0.15 mL) was collected at 2, 4, 8, 24, 48, 80, and 168 h post-dose (n=3 samples per time point, combined sampling) by sublingual puncture under mild Isoflurane anesthesia into $K_2$EDTA coated polypropylene tubes and placed on ice. Plasma was prepared within 30 min. by centrifugation at 3000 g for 5 min. at 4° C., frozen immediately and stored at −20° C. Test item concentrations in plasma were assessed by serial enzyme linked immune-sorbent assay (ELISA, see description below). Non-compartmental pharmacokinetic analysis for the fusion polypeptides was performed with the software ToxKin (Version 3.5.3, Entimo AG, 2008). Pharmacokinetic results are reported in FIG. 5 and Table 4.

Principle of the ELISA

To quantify the fusion polypeptides in 1% mouse plasma, a serial enzyme linked immunosorbent assay (ELISA) has been established using an antibody capturing the polypeptide under investigation (capturing mAb<polypeptide>IgG-Bi), then an antibody against the conjugated Fc-region (mAb<h-Fc-pan>IgG-Dig) and an anti-digoxigenin antibody-POD conjugate for detection.

Capture antibody, calibration standards of the fusion polypeptides or diluted plasma samples, mAb<h-Fc-pan>IgG-Dig, and anti-digoxigenin antibody-POD conjugate were successively added to a streptavidin coated microtiter plates (SA-MTP), incubating each reagent for one hour on a MTP shaker at 450 rpm. After each step the MTP was washed four times and residual fluids were removed. Finally, the formed immobilized immune complexes were visualized by addition of TMB solution, a POD substrate, which is converted to a colored reaction product. The color development was monitored photometrically (absorption at 655 nm/492 nm reference wavelength) and stopped by addition of 1 M $H_2SO_4$ when the highest calibrator reaches an OD of 0.75. Finally, the color intensity was photometrically determined (absorption at 450 nm/690 nm reference wavelength) and was proportional to the analyte concentration in the plasma sample. The quantification of the fusion polypeptides was performed by back calculation of the absorbance values using the corresponding calibration curve with a non-linear 4 parameter Wiemer-Rodbard curve fitting function.

Pharmacokinetic Results

Figure 5:
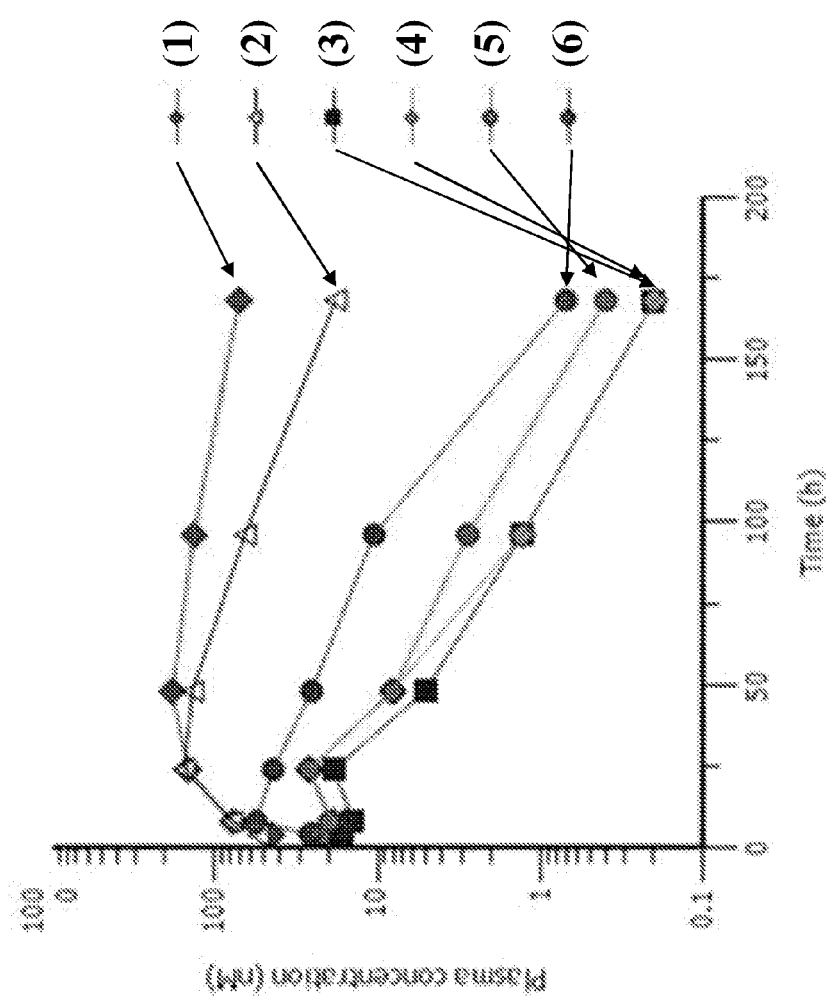
FIG. 5 Overview on the plasma concentration/time profiles of the tested fusion polypeptides as reported herein and PEGylated reference constructs after 20 nmol/kg single subcutaneous application to mice; (1/dark diamond) lipidated Fc-fusion as reported herein; (2/triangle) non-lipidated, PEGylated incretin receptor ligand polypeptide reference peptide 5; (3/squares) non-lipidated incretin receptor ligand polypeptide Fc-region fusion polypeptide reference 1; (4/light diamond) non-lipidated incretin receptor ligand polypeptide Fc-region fusion polypeptide reference 2; (5/light circle) non-lipidated incretin receptor ligand polypeptide Fc-region fusion polypeptide reference 3; (6/dark circle) non-lipidated incretin receptor ligand polypeptide Fc-region fusion polypeptide reference 4.

Plasma exposure after subcutaneous application: As shown in FIG. 5 and in Table 4, higher $C_{max}$ and AUC were observed in mice for the lipidated fusion polypeptides as compared to the PEG conjugate and to the four tested non lipidated fusion polypeptides.

Plasma half-life (T½) after subcutaneous application: A markedly long plasma T½ of 87 hours was observed in mice for the lipidated fusion polypeptides. In contrast, the four tested non lipidated fusion polypeptides showed a significantly shorter T½ of about 25 hours. T½ was also two-fold longer than what observed previously for the respective PEG-40k conjugate (41 hours).

TABLE 4

PK parameters in plasma after 20 nmol/kg single subcutaneous application to mice.

| | | type of construct | | | | | |
|---|---|---|---|---|---|---|---|
| PK parameter* | unit | lipidated Fc-fusion as reported herein | reference peptide 1 Fc-fusion, non-lipidated | reference peptide 2 Fc-fusion, non-lipidated | reference peptide 3 Fc-fusion, non-lipidated | reference peptide 4 Fc-fusion, non-lipidated | reference peptide 5 PEGylated non-lipidated |
| $T\frac{1}{2}$ (terminal) | h | 87 | 24 | 22 | 23 | 26 | 41 |
| $T_{max}$ | h | 48 | 24 | 24 | 8 | 24 | 24 |
| $C_{max}$ | nM | 182 | 18.6 | 26.3 | 56 | 26.3 | 153 |
| $C_{max}$/Dose | nM/(nmol/kg) | 9.11 | 0.93 | 1.32 | 2.79 | 1.32 | 7.68 |
| AUCInf | h*nmol/mL | 29.6 | 0.81 | 1.13 | 2.91 | 1.25 | 14.2 |
| $AUC_{0-24\ h}$ | h*nmol/mL | 2.20 | 0.38 | 0.54 | 1.01 | 0.54 | 2.34 |
| $AUC_{0-168\ h}$ | h*nmol/mL | 20.7 | 0.80 | 1.13 | 2.89 | 1.23 | 13.1 |

*Due to the combined sampling study layout, PK parameters refer to the mean plasma concentration/time profile. Mean plasma concentration/time profile for each construct was obtained from three concentration values per time point

What is claimed is:

1. A fusion polypeptide comprising
   a lipidated incretin receptor ligand polypeptide, and
   a human immunoglobulin Fc-region, wherein said lipidated incretin receptor ligand polypeptide comprises the amino acid sequence of SEQ ID NO: 125 and the Fc-region comprises SEQ ID NO: 53 and said Fc-region is conjugated to either the carboxy terminus or amino terminus of the incretin receptor ligand polypeptide.

2. A pharmaceutical composition comprising a fusion polypeptide according to claim 1.

3. A method of reducing weight gain or inducing weight loss, said method comprising administering the pharmaceutical composition of claim 2 to a patient in need thereof.

* * * * *

SEQUENCE LISTING

```
<160> NUMBER OF SEQ ID NOS: 125

<210> SEQ ID NO 1
<211> LENGTH: 31
<212> TYPE: PRT
<213> ORGANISM: Artificial Sequence
<220> FEATURE:
<223> OTHER INFORMATION: GLP-1(7-37)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: GLP-1(7-36)

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 39
<212> TYPE: PRT
<213> ORGANISM: Artificial Sequence
<220> FEATURE:
<223> OTHER INFORMATION: exendin-3

<400> SEQUENCE: 3

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
```

```
<211> LENGTH: 39
<212> TYPE: PRT
<213> ORGANISM: Artificial Sequence
<220> FEATURE:
<223> OTHER INFORMATION: exendin-4

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 31
<212> TYPE: PRT
<213> ORGANISM: Artificial Sequence
<220> FEATURE:
<223> OTHER INFORMATION: exendin-4(1-31) desGlu(17) Tyr(32)

<400> SEQUENCE: 5

His Gly Glu Gly Thr Phe Thr Ser Asp Leu Ser Lys Gln Met Glu Glu
1               5                   10                  15

Ala Val Arg Leu Phe Ile Glu Trp Leu Lys Asn Gly Gly Pro Tyr
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: exendin-4(1-30) Tyr(31)

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Tyr
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: exendin-4(9-39)

<400> SEQUENCE: 7

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 8
<211> LENGTH: 19
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (17)..(17)
<223> OTHER INFORMATION: Xaa denotes Lys or Arg

<400> SEQUENCE: 8
```

-continued

```
Ser Tyr Leu Glu Gly Gln Ala Ala Lys Glu Phe Ile Ala Trp Leu Val
1               5                   10                  15

Xaa Gly Arg

<210> SEQ ID NO 9
<211> LENGTH: 20
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (18)..(18)
<223> OTHER INFORMATION: Xaa denotes Lys or Arg

<400> SEQUENCE: 9

Ser Ser Tyr Leu Glu Gly Gln Ala Ala Lys Glu Phe Ile Ala Trp Leu
1               5                   10                  15

Val Xaa Gly Arg
            20

<210> SEQ ID NO 10
<211> LENGTH: 21
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (19)..(19)
<223> OTHER INFORMATION: Xaa denotes Lys or Arg

<400> SEQUENCE: 10

Val Ser Ser Tyr Leu Glu Gly Gln Ala Ala Lys Glu Phe Ile Ala Trp
1               5                   10                  15

Leu Val Xaa Gly Arg
            20

<210> SEQ ID NO 11
<211> LENGTH: 22
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (20)..(20)
<223> OTHER INFORMATION: Xaa denotes Lys or Arg

<400> SEQUENCE: 11

Asp Val Ser Ser Tyr Leu Glu Gly Gln Ala Ala Lys Glu Phe Ile Ala
1               5                   10                  15

Trp Leu Val Xaa Gly Arg
            20

<210> SEQ ID NO 12
<211> LENGTH: 23
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (21)..(21)
<223> OTHER INFORMATION: Xaa denotes Lys or Arg

<400> SEQUENCE: 12
```

Ser Asp Val Ser Ser Tyr Leu Glu Gly Gln Ala Ala Lys Glu Phe Ile
1               5                   10                  15

Ala Trp Leu Val Xaa Gly Arg
            20

<210> SEQ ID NO 13
<211> LENGTH: 24
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (22)..(22)
<223> OTHER INFORMATION: Xaa denotes Lys or Arg

<400> SEQUENCE: 13

Thr Ser Asp Val Ser Ser Tyr Leu Glu Gly Gln Ala Ala Lys Glu Phe
1               5                   10                  15

Ile Ala Trp Leu Val Xaa Gly Arg
            20

<210> SEQ ID NO 14
<211> LENGTH: 25
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (23)..(23)
<223> OTHER INFORMATION: Xaa denotes Lys or Arg

<400> SEQUENCE: 14

Phe Thr Ser Asp Val Ser Ser Tyr Leu Glu Gly Gln Ala Ala Lys Glu
1               5                   10                  15

Phe Ile Ala Trp Leu Val Xaa Gly Arg
            20                  25

<210> SEQ ID NO 15
<211> LENGTH: 26
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (24)..(24)
<223> OTHER INFORMATION: Xaa denotes Lys or Arg

<400> SEQUENCE: 15

Thr Phe Thr Ser Asp Val Ser Ser Tyr Leu Glu Gly Gln Ala Ala Lys
1               5                   10                  15

Glu Phe Ile Ala Trp Leu Val Xaa Gly Arg
            20                  25

<210> SEQ ID NO 16
<211> LENGTH: 27
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (25)..(25)
<223> OTHER INFORMATION: Xaa denotes Lys or Arg

<400> SEQUENCE: 16

```
Gly Thr Phe Thr Ser Asp Val Ser Ser Tyr Leu Glu Gly Gln Ala Ala
1               5                   10                  15

Lys Glu Phe Ile Ala Trp Leu Val Xaa Gly Arg
            20                  25
```

<210> SEQ ID NO 17
<211> LENGTH: 28
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (26)..(26)
<223> OTHER INFORMATION: Xaa denotes Lys or Arg

<400> SEQUENCE: 17

```
Glu Gly Thr Phe Thr Ser Asp Val Ser Ser Tyr Leu Glu Gly Gln Ala
1               5                   10                  15

Ala Lys Glu Phe Ile Ala Trp Leu Val Xaa Gly Arg
            20                  25
```

<210> SEQ ID NO 18
<211> LENGTH: 29
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (27)..(27)
<223> OTHER INFORMATION: Xaa denotes Lys or Arg

<400> SEQUENCE: 18

```
Ala Glu Gly Thr Phe Thr Ser Asp Val Ser Ser Tyr Leu Glu Gly Gln
1               5                   10                  15

Ala Ala Lys Glu Phe Ile Ala Trp Leu Val Xaa Gly Arg
            20                  25
```

<210> SEQ ID NO 19
<211> LENGTH: 30
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (28)..(28)
<223> OTHER INFORMATION: Xaa denotes Lys or Arg

<400> SEQUENCE: 19

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Gly Arg
            20                  25                  30
```

<210> SEQ ID NO 20
<211> LENGTH: 31
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (29)..(29)
<223> OTHER INFORMATION: Xaa denotes Lys or Arg

```
<400> SEQUENCE: 20

His Asp Ala Glu Gly Thr Phe Thr Ser Asp Val Ser Ser Tyr Leu Glu
1               5                   10                  15

Gly Gln Ala Ala Lys Glu Phe Ile Ala Trp Leu Val Xaa Gly Arg
            20                  25                  30

<210> SEQ ID NO 21
<211> LENGTH: 39
<212> TYPE: PRT
<213> ORGANISM: Artificial Sequence
<220> FEATURE:
<223> OTHER INFORMATION: hybrid GLP-1/exendin polypeptide

<400> SEQUENCE: 21

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser Gly Ala Pro Pro Pro Ser
        35

<210> SEQ ID NO 22
<211> LENGTH: 37
<212> TYPE: PRT
<213> ORGANISM: Artificial Sequence
<220> FEATURE:
<223> OTHER INFORMATION: incretin receptor ligand polypeptide

<400> SEQUENCE: 22

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Lys
        35

<210> SEQ ID NO 23
<211> LENGTH: 31
<212> TYPE: PRT
<213> ORGANISM: Artificial Sequence
<220> FEATURE:
<223> OTHER INFORMATION: incretin receptor ligand polypeptide

<400> SEQUENCE: 23

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Lys
            20                  25                  30

<210> SEQ ID NO 24
<211> LENGTH: 40
<212> TYPE: PRT
<213> ORGANISM: Artificial Sequence
<220> FEATURE:
<223> OTHER INFORMATION: incretin receptor ligand polypeptide

<400> SEQUENCE: 24

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
```

35                  40

<210> SEQ ID NO 25
<211> LENGTH: 40
<212> TYPE: PRT
<213> ORGANISM: Artificial Sequence
<220> FEATURE:
<223> OTHER INFORMATION: incretin receptor ligand polypeptide

<400> SEQUENCE: 25

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 26
<211> LENGTH: 31
<212> TYPE: PRT
<213> ORGANISM: Artificial Sequence
<220> FEATURE:
<223> OTHER INFORMATION: incretin receptor ligand polypeptide

<400> SEQUENCE: 26

His Gly Glu Gly Thr Phe Thr Ser Asp Leu Ser Lys Glu Met Glu Glu
1               5                   10                  15

Glu Val Arg Leu Phe Ile Glu Trp Leu Lys Asn Gly Gly Pro Tyr
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: incretin receptor ligand polypeptide

<400> SEQUENCE: 27

His Gly Glu Gly Thr Phe Thr Ser Asp Leu Ser Lys Glu Met Glu Glu
1               5                   10                  15

Glu Val Arg Leu Phe Ile Glu Trp Leu Lys Asn Gly Gly Tyr
            20                  25                  30

<210> SEQ ID NO 28
<211> LENGTH: 29
<212> TYPE: PRT
<213> ORGANISM: Artificial Sequence
<220> FEATURE:
<223> OTHER INFORMATION: incretin receptor ligand polypeptide

<400> SEQUENCE: 28

Asp Leu Ser Lys Gln Met Glu Glu Glu Ala Val Arg Leu Phe Ile Glu
1               5                   10                  15

Trp Leu Lys Gly Gly Pro Ser Ser Gly Pro Pro Pro Ser
            20                  25

<210> SEQ ID NO 29
<211> LENGTH: 40
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)

-continued

```
<223> OTHER INFORMATION: Xaa denotes aib
<220> FEATURE:
<221> NAME/KEY: MISC_FEATURE
<222> LOCATION: (20)..(20)
<223> OTHER INFORMATION: Xaa denotes aib

<400> SEQUENCE: 29

Tyr Xaa Glu Gly Thr Phe Thr Ser Asp Tyr Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 30
<211> LENGTH: 40
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (20)..(20)
<223> OTHER INFORMATION: Xaa denotes aib

<400> SEQUENCE: 30

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 31
<211> LENGTH: 40
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (20)..(20)
<223> OTHER INFORMATION: Xaa denotes aib

<400> SEQUENCE: 31

Tyr Xaa Glu Gly Thr Phe Thr Ser Asp Tyr Ser Ile Tyr Leu Asp Lys
1               5                   10                  15

Gln Ala Ala Xaa Glu Phe Val Ala Trp Leu Leu Ala Gly Gly Pro Ser
            20                  25                  30

Ser Gly Ala Pro Pro Pro Ser Lys
        35                  40

<210> SEQ ID NO 32
<211> LENGTH: 31
<212> TYPE: PRT
<213> ORGANISM: Artificial Sequence
<220> FEATURE:
<223> OTHER INFORMATION: incretin receptor ligand polypeptide
<220> FEATURE:
```

```
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (20)..(20)
<223> OTHER INFORMATION: Xaa denotes aib

<400> SEQUENCE: 32

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Gly
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (20)..(20)
<223> OTHER INFORMATION: Xaa denotes aib

<400> SEQUENCE: 33

Tyr Xaa Glu Gly Thr Phe Thr Ser Asp Tyr Ser Ile Tyr Leu Asp Lys
1               5                   10                  15

Gln Ala Ala Xaa Glu Phe Val Ala Trp Leu Leu Ala Gly Gly Gly
            20                  25                  30

<210> SEQ ID NO 34
<211> LENGTH: 40
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)
<223> OTHER INFORMATION: Xaa denotes aib

<400> SEQUENCE: 34

Tyr Xaa Glu Gly Thr Phe Thr Ser Asp Tyr Ser Ile Tyr Leu Asp Glu
1               5                   10                  15

Gln Ala Ala Lys Glu Phe Val Asn Trp Leu Leu Ala Gly Gly Pro Ser
            20                  25                  30

Ser Gly Ala Pro Pro Pro Ser Cys
        35                  40

<210> SEQ ID NO 35
<211> LENGTH: 40
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (20)..(20)
<223> OTHER INFORMATION: Xaa denotes aib
```

<400> SEQUENCE: 35

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 36
<211> LENGTH: 40
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (20)..(20)
<223> OTHER INFORMATION: Xaa denotes aib

<400> SEQUENCE: 36

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 37
<211> LENGTH: 40
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (16)..(20)
<223> OTHER INFORMATION: lactam ring between residues 16 and 20

<400> SEQUENCE: 37

Tyr Xaa Gln Gly Thr Phe Thr Ser Asp Tyr Ser Ile Tyr Leu Asp Glu
1               5                   10                  15

Gln Ala Ala Lys Glu Phe Val Asn Trp Leu Leu Ala Gly Gly Pro Ser
            20                  25                  30

Ser Gly Ala Pro Pro Pro Ser Cys
        35                  40

<210> SEQ ID NO 38
<211> LENGTH: 40
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (16)..(20)

<223> OTHER INFORMATION: lactam ring between residues 16 and 20

<400> SEQUENCE: 38

Tyr Xaa Gln Gly Thr Phe Ile Ser Asp Tyr Ser Ile Tyr Leu Asp Glu
1               5                   10                  15

Gln Ala Ala Lys Glu Phe Val Asn Trp Leu Leu Ala Gly Gly Pro Ser
            20                  25                  30

Ser Gly Ala Pro Pro Ser Cys
        35                  40

<210> SEQ ID NO 39
<211> LENGTH: 29
<212> TYPE: PRT
<213> ORGANISM: Artificial Sequence
<220> FEATURE:
<223> OTHER INFORMATION: incretin receptor ligand polypeptide
<220> FEATURE:
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (16)..(20)
<223> OTHER INFORMATION: lactam ring between residues 16 and 20

<400> SEQUENCE: 39

Tyr Xaa Gln Gly Thr Phe Ile Ser Asp Tyr Ser Ile Tyr Leu Asp Glu
1               5                   10                  15

Gln Ala Ala Lys Glu Phe Val Cys Trp Leu Leu Ala Gly
            20                  25

<210> SEQ ID NO 40
<211> LENGTH: 107
<212> TYPE: PRT
<213> ORGANISM: Homo sapiens

<400> SEQUENCE: 40

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105

<210> SEQ ID NO 41
<211> LENGTH: 106
<212> TYPE: PRT
<213> ORGANISM: Homo sapiens

<400> SEQUENCE: 41

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

```
Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 42
<211> LENGTH: 227
<212> TYPE: PRT
<213> ORGANISM: Homo sapiens

<400> SEQUENCE: 42

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 43
<211> LENGTH: 227
<212> TYPE: PRT
<213> ORGANISM: Artificial Sequence
<220> FEATURE:
<223> OTHER INFORMATION: variant human Fc-region of the IgG1 isotype
      with the mutations L234A, L235A

<400> SEQUENCE: 43
```

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                      55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 44
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a hole mutation

<400> SEQUENCE: 44

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                      55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
```

```
            115                 120                 125
Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 45
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a knob mutation

<400> SEQUENCE: 45

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

-continued

<210> SEQ ID NO 46
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a L234A, L235A and hole mutation

<400> SEQUENCE: 46

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 47
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a L234A, L235A and knob mutation

<400> SEQUENCE: 47

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 48
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a P329G mutation

<400> SEQUENCE: 48

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

```
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 49
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a L234A, L235A and P329G mutation

<400> SEQUENCE: 49

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 50
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a P239G and hole mutation

<400> SEQUENCE: 50

Asp Lys Thr His Thr Cys Pro Pro Cys Pro Ala Pro Glu Leu Leu Gly
1               5                   10                  15
```

```
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 51
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a P329G and knob mutation

<400> SEQUENCE: 51

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
```

```
              130                 135                 140
Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225

<210> SEQ ID NO 52
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a L234A, L235A, P329G and hole mutation

<400> SEQUENCE: 52

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
                100                 105                 110

Glu Lys Thr Ile Ser Lys Ala Lys Gly Gln Pro Arg Glu Pro Gln Val
                115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225

<210> SEQ ID NO 53
<211> LENGTH: 227
```

```
<212> TYPE: PRT
<213> ORGANISM: Artificial Sequence
<220> FEATURE:
<223> OTHER INFORMATION: variant human Fc-region of the IgG1 isotype
      with a L234A, L235A, P329G and knob mutation

<400> SEQUENCE: 53

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 54
<211> LENGTH: 229
<212> TYPE: PRT
<213> ORGANISM: Homo sapiens

<400> SEQUENCE: 54

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95
```

```
Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 55
<211> LENGTH: 229
<212> TYPE: PRT
<213> ORGANISM: Artificial Sequence
<220> FEATURE:
<223> OTHER INFORMATION: variant human Fc-region of the IgG4 isotype
      with a S228P and L235E mutation

<400> SEQUENCE: 55

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220
```

Leu Ser Leu Gly Lys
225

<210> SEQ ID NO 56
<211> LENGTH: 229
<212> TYPE: PRT
<213> ORGANISM: Artificial Sequence
<220> FEATURE:
<223> OTHER INFORMATION: variant human Fc-region of the IgG4 isotype
      with a S228P, L235E and P329G mutation

<400> SEQUENCE: 56

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 57
<211> LENGTH: 12
<212> TYPE: PRT
<213> ORGANISM: Artificial Sequence
<220> FEATURE:
<223> OTHER INFORMATION: linker polypeptide

<400> SEQUENCE: 57

Gly Gly Gly Ser Gly Gly Gly Ser Gly Gly Gly Ser
1               5                   10

<210> SEQ ID NO 58
<211> LENGTH: 16
<212> TYPE: PRT
<213> ORGANISM: Artificial Sequence
<220> FEATURE:

```
<223> OTHER INFORMATION: linker polypeptide

<400> SEQUENCE: 58

Gly Gly Gly Ser Gly Gly Gly Ser Gly Gly Gly Ser Gly Gly Gly Ser
1               5                   10                  15

<210> SEQ ID NO 59
<211> LENGTH: 20
<212> TYPE: PRT
<213> ORGANISM: Artificial Sequence
<220> FEATURE:
<223> OTHER INFORMATION: linker polypeptide

<400> SEQUENCE: 59

Gly Gly Gly Ser Gly Gly Gly Ser Gly Gly Gly Ser Gly Gly Gly Ser
1               5                   10                  15

Gly Gly Gly Ser
            20

<210> SEQ ID NO 60
<211> LENGTH: 24
<212> TYPE: PRT
<213> ORGANISM: Artificial Sequence
<220> FEATURE:
<223> OTHER INFORMATION: linker polypeptide

<400> SEQUENCE: 60

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 61
<211> LENGTH: 10
<212> TYPE: PRT
<213> ORGANISM: Artificial Sequence
<220> FEATURE:
<223> OTHER INFORMATION: linker polypeptide

<400> SEQUENCE: 61

Gly Gly Gly Gly Ser Gly Gly Gly Gly Ser
1               5                   10

<210> SEQ ID NO 62
<211> LENGTH: 15
<212> TYPE: PRT
<213> ORGANISM: Artificial Sequence
<220> FEATURE:
<223> OTHER INFORMATION: linker polypeptide

<400> SEQUENCE: 62

Gly Gly Gly Gly Ser Gly Gly Gly Gly Ser Gly Gly Gly Gly Ser
1               5                   10                  15

<210> SEQ ID NO 63
<211> LENGTH: 20
<212> TYPE: PRT
<213> ORGANISM: Artificial Sequence
<220> FEATURE:
<223> OTHER INFORMATION: linker polypeptide

<400> SEQUENCE: 63

Gly Gly Gly Gly Ser Gly Gly Gly Gly Ser Gly Gly Gly Gly Ser Gly
1               5                   10                  15

Gly Gly Gly Ser
```

```
<210> SEQ ID NO 64
<211> LENGTH: 25
<212> TYPE: PRT
<213> ORGANISM: Artificial Sequence
<220> FEATURE:
<223> OTHER INFORMATION: linker polypeptide

<400> SEQUENCE: 64

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 65
<211> LENGTH: 12
<212> TYPE: PRT
<213> ORGANISM: Artificial Sequence
<220> FEATURE:
<223> OTHER INFORMATION: linker polypeptide

<400> SEQUENCE: 65

Gly Gly Gly Gly Gly Ser Gly Gly Gly Gly Gly Ser
1               5                   10

<210> SEQ ID NO 66
<211> LENGTH: 18
<212> TYPE: PRT
<213> ORGANISM: Artificial Sequence
<220> FEATURE:
<223> OTHER INFORMATION: linker polypeptide

<400> SEQUENCE: 66

Gly Gly Gly Gly Gly Ser Gly Gly Gly Gly Ser Gly Gly Gly Gly
1               5                   10                  15

Gly Ser

<210> SEQ ID NO 67
<211> LENGTH: 24
<212> TYPE: PRT
<213> ORGANISM: Artificial Sequence
<220> FEATURE:
<223> OTHER INFORMATION: linker polypeptide

<400> SEQUENCE: 67

Gly Gly Gly Gly Gly Ser Gly Gly Gly Gly Ser Gly Gly Gly Gly
1               5                   10                  15

Gly Ser Gly Gly Gly Gly Gly Ser
            20

<210> SEQ ID NO 68
<211> LENGTH: 230
<212> TYPE: PRT
<213> ORGANISM: Artificial Sequence
<220> FEATURE:
<223> OTHER INFORMATION: G3-Fc

<400> SEQUENCE: 68

Gly Gly Gly Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
```

```
                35                  40                  45
Val Ser His Glu Asp Pro Glu Val Lys Phe Asn Trp Tyr Val Asp Gly
 50                  55                  60

Val Glu Val His Asn Ala Lys Thr Lys Pro Arg Glu Glu Gln Tyr Asn
 65                  70                  75                  80

Ser Thr Tyr Arg Val Val Ser Val Leu Thr Val Leu His Gln Asp Trp
                 85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
            195                 200                 205

Ser Val Met His Glu Ala Leu His Asn His Tyr Thr Gln Lys Ser Leu
            210                 215                 220

Ser Leu Ser Pro Gly Lys
225                 230

<210> SEQ ID NO 69
<211> LENGTH: 242
<212> TYPE: PRT
<213> ORGANISM: Artificial Sequence
<220> FEATURE:
<223> OTHER INFORMATION: G4S3-Fc

<400> SEQUENCE: 69

Gly Gly Gly Gly Ser Gly Gly Gly Gly Ser Gly Gly Gly Gly Ser Asp
 1               5                  10                  15

Lys Thr His Thr Cys Pro Pro Cys Pro Ala Pro Glu Leu Leu Gly Gly
                 20                  25                  30

Pro Ser Val Phe Leu Phe Pro Pro Lys Pro Lys Asp Thr Leu Met Ile
             35                  40                  45

Ser Arg Thr Pro Glu Val Thr Cys Val Val Val Asp Val Ser His Glu
 50                  55                  60

Asp Pro Glu Val Lys Phe Asn Trp Tyr Val Asp Gly Val Glu Val His
 65                  70                  75                  80

Asn Ala Lys Thr Lys Pro Arg Glu Glu Gln Tyr Asn Ser Thr Tyr Arg
                 85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
            115                 120                 125

Lys Thr Ile Ser Lys Ala Lys Gly Gln Pro Arg Glu Pro Gln Val Tyr
        130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
```

```
                    165                 170                 175
Glu Ser Asn Gly Gln Pro Glu Asn Asn Tyr Lys Thr Thr Pro Pro Val
                180                 185                 190

Leu Asp Ser Asp Gly Ser Phe Phe Leu Tyr Ser Lys Leu Thr Val Asp
            195                 200                 205

Lys Ser Arg Trp Gln Gln Gly Asn Val Phe Ser Cys Ser Val Met His
        210                 215                 220

Glu Ala Leu His Asn His Tyr Thr Gln Lys Ser Leu Ser Leu Ser Pro
225                 230                 235                 240

Gly Lys

<210> SEQ ID NO 70
<211> LENGTH: 49
<212> TYPE: PRT
<213> ORGANISM: Artificial Sequence
<220> FEATURE:
<223> OTHER INFORMATION: long incretin receptor ligand polypeptide with
      sortase tag
<220> FEATURE:
<221> NAME/KEY: MISC_FEATURE
<222> LOCATION: (2)..(2)
<223> OTHER INFORMATION: Xaa denotes aib
<220> FEATURE:
<221> NAME/KEY: MISC_FEATURE
<222> LOCATION: (20)..(20)
<223> OTHER INFORMATION: Xaa denotes aib
<220> FEATURE:
<221> NAME/KEY: MISC_FEATURE
<222> LOCATION: (49)..(49)
<223> OTHER INFORMATION: Xaa denotes serine amide

<400> SEQUENCE: 70

Tyr Xaa Glu Gly Thr Phe Thr Ser Asp Tyr Ser Ile Tyr Leu Asp Lys
1               5                   10                  15

Gln Ala Ala Xaa Glu Phe Val Ala Trp Leu Leu Ala Gly Gly Pro Ser
            20                  25                  30

Ser Gly Ala Pro Pro Pro Ser Lys Leu Pro Glu Thr Gly Gly Ser Gly
        35                  40                  45

Xaa

<210> SEQ ID NO 71
<211> LENGTH: 40
<212> TYPE: PRT
<213> ORGANISM: Artificial Sequence
<220> FEATURE:
<223> OTHER INFORMATION: short incretin receptor ligand polypeptide with
      sortase tag
<220> FEATURE:
<221> NAME/KEY: misc_feature
<222> LOCATION: (2)..(2)
<223> OTHER INFORMATION: X=aib
<220> FEATURE:
<221> NAME/KEY: misc_feature
<222> LOCATION: (20)..(20)
<223> OTHER INFORMATION: X=aib
<220> FEATURE:
<221> NAME/KEY: misc_feature
<222> LOCATION: (40)..(40)
<223> OTHER INFORMATION: X=serine amide

<400> SEQUENCE: 71

Tyr Xaa Glu Gly Thr Phe Thr Ser Asp Tyr Ser Ile Tyr Leu Asp Lys
1               5                   10                  15

Gln Ala Ala Xaa Glu Phe Val Ala Trp Leu Leu Ala Gly Gly Gly Leu
            20                  25                  30
```

```
Pro Glu Thr Gly Gly Ser Gly Ser
        35                  40

<210> SEQ ID NO 72
<211> LENGTH: 9
<212> TYPE: PRT
<213> ORGANISM: Artificial Sequence
<220> FEATURE:
<223> OTHER INFORMATION: sortase motif

<400> SEQUENCE: 72

Leu Pro Glu Thr Gly Gly Ser Gly Ser
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is an acidic amino acid such as Asp or Glu

<400> SEQUENCE: 73

Leu Pro Xaa Thr Gly
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic peptide

<400> SEQUENCE: 74

Leu Pro Glu Thr Gly
1               5

<210> SEQ ID NO 75
<211> LENGTH: 5
<212> TYPE: PRT
<213> ORGANISM: Artificial Sequence
<220> FEATURE:
<223> OTHER INFORMATION: Synethic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 75

Leu Pro Xaa Thr Gly
1               5

<210> SEQ ID NO 76
<211> LENGTH: 29
<212> TYPE: PRT
<213> ORGANISM: Homo sapiens

<400> SEQUENCE: 76

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 77
```

```
<211> LENGTH: 42
<212> TYPE: PRT
<213> ORGANISM: Homo sapiens

<400> SEQUENCE: 77

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 78
<211> LENGTH: 10
<212> TYPE: PRT
<213> ORGANISM: Artificial Sequence
<220> FEATURE:
<223> OTHER INFORMATION: Synthetic peptide

<400> SEQUENCE: 78

Gly Pro Ser Ser Gly Ala Pro Pro Pro Ser
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is any amino acid

<400> SEQUENCE: 79

Xaa Gly Pro Ser Ser Gly Ala Pro Pro Pro Ser
1               5                   10

<210> SEQ ID NO 80

<400> SEQUENCE: 80

000

<210> SEQ ID NO 81

<400> SEQUENCE: 81

000

<210> SEQ ID NO 82
<211> LENGTH: 6
<212> TYPE: PRT
<213> ORGANISM: Artificial Sequence
<220> FEATURE:
<223> OTHER INFORMATION: Synthetic peptide

<400> SEQUENCE: 82

Gly Gly Ser Gly Gly Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide
```

<400> SEQUENCE: 83

Gly Gly Ser Gly Gly Ser Gly Gly Ser
1               5

<210> SEQ ID NO 84
<211> LENGTH: 12
<212> TYPE: PRT
<213> ORGANISM: Artificial Sequence
<220> FEATURE:
<223> OTHER INFORMATION: Synthetic peptide

<400> SEQUENCE: 84

Gly Gly Ser Gly Gly Ser Gly Gly Ser Gly Gly Ser
1               5                   10

<210> SEQ ID NO 85
<211> LENGTH: 4
<212> TYPE: PRT
<213> ORGANISM: Artificial Sequence
<220> FEATURE:
<223> OTHER INFORMATION: Synthetic peptide

<400> SEQUENCE: 85

Gly Gly Gly Gly
1

<210> SEQ ID NO 86
<211> LENGTH: 5
<212> TYPE: PRT
<213> ORGANISM: Artificial Sequence
<220> FEATURE:
<223> OTHER INFORMATION: Synthetic peptide

<400> SEQUENCE: 86

Gly Gly Gly Gly Gly
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic peptide

<400> SEQUENCE: 87

Gly Gly Gly Gly Gly Gly
1               5

<210> SEQ ID NO 88
<211> LENGTH: 4
<212> TYPE: PRT
<213> ORGANISM: Artificial Sequence
<220> FEATURE:
<223> OTHER INFORMATION: Synthetic peptide

<400> SEQUENCE: 88

Gly Gly Gly Ser
1

<210> SEQ ID NO 89
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 89

Gly Gly Gly Ser Gly Gly Gly Ser
1               5

<210> SEQ ID NO 90
<211> LENGTH: 5
<212> TYPE: PRT
<213> ORGANISM: Artificial Sequence
<220> FEATURE:
<223> OTHER INFORMATION: Synthetic peptide

<400> SEQUENCE: 90

Gly Gly Gly Gly Ser
1               5

<210> SEQ ID NO 91
<211> LENGTH: 30
<212> TYPE: PRT
<213> ORGANISM: Artificial Sequence
<220> FEATURE:
<223> OTHER INFORMATION: Synthetic peptide

<400> SEQUENCE: 91

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 92
<211> LENGTH: 6
<212> TYPE: PRT
<213> ORGANISM: Artificial Sequence
<220> FEATURE:
<223> OTHER INFORMATION: Synthetic peptide

<400> SEQUENCE: 92

Gly Gly Gly Gly Gly Ser
1               5

<210> SEQ ID NO 93
<211> LENGTH: 30
<212> TYPE: PRT
<213> ORGANISM: Artificial Sequence
<220> FEATURE:
<223> OTHER INFORMATION: Synthetic peptide

<400> SEQUENCE: 93

Gly Gly Gly Gly Gly Ser Gly Gly Gly Gly Gly Ser Gly Gly Gly Gly
1               5                   10                  15

Gly Ser Gly Gly Gly Gly Gly Ser Gly Gly Gly Gly Gly Ser
            20                  25                  30

<210> SEQ ID NO 94
<211> LENGTH: 36
<212> TYPE: PRT
<213> ORGANISM: Artificial Sequence
<220> FEATURE:
<223> OTHER INFORMATION: Synthetic peptide

<400> SEQUENCE: 94

Gly Gly Gly Gly Gly Ser Gly Gly Gly Gly Ser Gly Gly Gly Gly
1               5                   10                  15

Gly Ser Gly Gly Gly Gly Gly Ser Gly Gly Gly Gly Ser Gly Gly
            20                  25                  30
```

<210> SEQ ID NO 95
<211> LENGTH: 274
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB

<400> SEQUENCE: 95

Tyr Xaa Glu Gly Thr Phe Thr Ser Asp Tyr Ser Ile Tyr Leu Asp Lys
1               5                   10                  15
Gln Ala Ala Xaa Glu Phe Val Ala Trp Leu Leu Ala Gly Gly Pro Ser
            20                  25                  30
Ser Gly Ala Pro Pro Pro Ser Lys Leu Pro Glu Thr Gly Gly Gly Asp
        35                  40                  45
Lys Thr His Thr Cys Pro Pro Cys Pro Ala Pro Glu Leu Leu Gly Gly
    50                  55                  60
Pro Ser Val Phe Leu Phe Pro Pro Lys Pro Lys Asp Thr Leu Met Ile
65                  70                  75                  80
Ser Arg Thr Pro Glu Val Thr Cys Val Val Val Asp Val Ser His Glu
                85                  90                  95
Asp Pro Glu Val Lys Phe Asn Trp Tyr Val Asp Gly Val Glu Val His
            100                 105                 110
Asn Ala Lys Thr Lys Pro Arg Glu Glu Gln Tyr Asn Ser Thr Tyr Arg
        115                 120                 125
Val Val Ser Val Leu Thr Val Leu His Gln Asp Trp Leu Asn Gly Lys
    130                 135                 140
Glu Tyr Lys Cys Lys Val Ser Asn Lys Ala Leu Pro Ala Pro Ile Glu
145                 150                 155                 160
Lys Thr Ile Ser Lys Ala Lys Gly Gln Pro Arg Glu Pro Gln Val Tyr
                165                 170                 175
Thr Leu Pro Pro Ser Arg Asp Glu Leu Thr Lys Asn Gln Val Ser Leu
            180                 185                 190
Thr Cys Leu Val Lys Gly Phe Tyr Pro Ser Asp Ile Ala Val Glu Trp
        195                 200                 205
Glu Ser Asn Gly Gln Pro Glu Asn Asn Tyr Lys Thr Thr Pro Pro Val
    210                 215                 220
Leu Asp Ser Asp Gly Ser Phe Phe Leu Tyr Ser Lys Leu Thr Val Asp
225                 230                 235                 240
Lys Ser Arg Trp Gln Gln Gly Asn Val Phe Ser Cys Ser Val Met His
                245                 250                 255
Glu Ala Leu His Asn His Tyr Thr Gln Lys Ser Leu Ser Leu Ser Pro
            260                 265                 270
Gly Lys

<210> SEQ ID NO 96
<211> LENGTH: 265
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB

<400> SEQUENCE: 96

Tyr Xaa Glu Gly Thr Phe Thr Ser Asp Tyr Ser Ile Tyr Leu Asp Lys
1               5                   10                  15

Gln Ala Ala Xaa Glu Phe Val Ala Trp Leu Leu Ala Gly Gly Gly Leu
            20                  25                  30

Pro Glu Thr Gly Gly Gly Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys
            260                 265

<210> SEQ ID NO 97
<211> LENGTH: 286
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB

<400> SEQUENCE: 97

Tyr Xaa Glu Gly Thr Phe Thr Ser Asp Tyr Ser Ile Tyr Leu Asp Lys
1               5                   10                  15

Gln Ala Ala Xaa Glu Phe Val Ala Trp Leu Leu Ala Gly Gly Pro Ser
            20                  25                  30

Ser Gly Ala Pro Pro Ser Lys Leu Pro Glu Thr Gly Gly Gly
        35                  40                  45

Ser Gly Gly Gly Gly Ser Gly Gly Gly Ser Asp Lys Thr His Thr
    50                  55                  60

Cys Pro Pro Cys Pro Ala Pro Glu Leu Gly Gly Pro Ser Val Phe
65              70                  75                  80

Leu Phe Pro Pro Lys Pro Lys Asp Thr Leu Met Ile Ser Arg Thr Pro
                85                  90                  95

Glu Val Thr Cys Val Val Val Asp Val Ser His Glu Asp Pro Glu Val
                100                 105                 110

Lys Phe Asn Trp Tyr Val Asp Gly Val Glu Val His Asn Ala Lys Thr
            115                 120                 125

Lys Pro Arg Glu Glu Gln Tyr Asn Ser Thr Tyr Arg Val Val Ser Val
130                 135                 140

Leu Thr Val Leu His Gln Asp Trp Leu Asn Gly Lys Glu Tyr Lys Cys
145                 150                 155                 160

Lys Val Ser Asn Lys Ala Leu Pro Ala Pro Ile Glu Lys Thr Ile Ser
                165                 170                 175

Lys Ala Lys Gly Gln Pro Arg Glu Pro Gln Val Tyr Thr Leu Pro Pro
            180                 185                 190

Ser Arg Asp Glu Leu Thr Lys Asn Gln Val Ser Leu Thr Cys Leu Val
        195                 200                 205

Lys Gly Phe Tyr Pro Ser Asp Ile Ala Val Glu Trp Glu Ser Asn Gly
210                 215                 220

Gln Pro Glu Asn Asn Tyr Lys Thr Thr Pro Pro Val Leu Asp Ser Asp
225                 230                 235                 240

Gly Ser Phe Phe Leu Tyr Ser Lys Leu Thr Val Asp Lys Ser Arg Trp
                245                 250                 255

Gln Gln Gly Asn Val Phe Ser Cys Ser Val Met His Glu Ala Leu His
            260                 265                 270

Asn His Tyr Thr Gln Lys Ser Leu Ser Leu Ser Pro Gly Lys
        275                 280                 285

<210> SEQ ID NO 98
<211> LENGTH: 277
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB

<400> SEQUENCE: 98

Tyr Xaa Glu Gly Thr Phe Thr Ser Asp Tyr Ser Ile Tyr Leu Asp Lys
1               5                   10                  15

Gln Ala Ala Xaa Glu Phe Val Ala Trp Leu Leu Ala Gly Gly Gly Leu

-continued

```
                20                  25                  30
Pro Glu Thr Gly Gly Gly Ser Gly Gly Gly Ser Gly Gly
            35                  40                  45
Gly Ser Asp Lys Thr His Thr Cys Pro Pro Cys Pro Ala Pro Glu Leu
50                  55                  60
Leu Gly Gly Pro Ser Val Phe Leu Phe Pro Pro Lys Pro Lys Asp Thr
65                  70                  75                  80
Leu Met Ile Ser Arg Thr Pro Glu Val Thr Cys Val Val Val Asp Val
                85                  90                  95
Ser His Glu Asp Pro Glu Val Lys Phe Asn Trp Tyr Val Asp Gly Val
            100                 105                 110
Glu Val His Asn Ala Lys Thr Lys Pro Arg Glu Glu Gln Tyr Asn Ser
        115                 120                 125
Thr Tyr Arg Val Val Ser Val Leu Thr Val Leu His Gln Asp Trp Leu
    130                 135                 140
Asn Gly Lys Glu Tyr Lys Cys Lys Val Ser Asn Lys Ala Leu Pro Ala
145                 150                 155                 160
Pro Ile Glu Lys Thr Ile Ser Lys Ala Lys Gly Gln Pro Arg Glu Pro
                165                 170                 175
Gln Val Tyr Thr Leu Pro Pro Ser Arg Asp Glu Leu Thr Lys Asn Gln
            180                 185                 190
Val Ser Leu Thr Cys Leu Val Lys Gly Phe Tyr Pro Ser Asp Ile Ala
        195                 200                 205
Val Glu Trp Glu Ser Asn Gly Gln Pro Glu Asn Asn Tyr Lys Thr Thr
    210                 215                 220
Pro Pro Val Leu Asp Ser Asp Gly Ser Phe Phe Leu Tyr Ser Lys Leu
225                 230                 235                 240
Thr Val Asp Lys Ser Arg Trp Gln Gln Gly Asn Val Phe Ser Cys Ser
                245                 250                 255
Val Met His Glu Ala Leu His Asn His Tyr Thr Gln Lys Ser Leu Ser
            260                 265                 270
Leu Ser Pro Gly Lys
            275

<210> SEQ ID NO 99
<211> LENGTH: 3
<212> TYPE: PRT
<213> ORGANISM: Artificial Sequence
<220> FEATURE:
<223> OTHER INFORMATION: Synthetic peptide

<400> SEQUENCE: 99

Gly Gly Gly
1

<210> SEQ ID NO 100
<211> LENGTH: 42
<212> TYPE: PRT
<213> ORGANISM: Artificial Sequence
<220> FEATURE:
<223> OTHER INFORMATION: lipidated incretin receptor polypeptide 1
<220> FEATURE:
<221> NAME/KEY: MISC_FEATURE
<222> LOCATION: (2)..(2)
<223> OTHER INFORMATION: X=aib
<220> FEATURE:
<221> NAME/KEY: MISC_FEATURE
<222> LOCATION: (11)..(11)
<223> OTHER INFORMATION: X=gamma glutamic acid
<220> FEATURE:
```

```
<221> NAME/KEY: MISC_FEATURE
<222> LOCATION: (12)..(12)
<223> OTHER INFORMATION: X=gamma glutamic acid with palmytoic acid ester
<220> FEATURE:
<221> NAME/KEY: MISC_FEATURE
<222> LOCATION: (22)..(22)
<223> OTHER INFORMATION: X=aib
<220> FEATURE:
<221> NAME/KEY: MISC_FEATURE
<222> LOCATION: (42)..(42)
<223> OTHER INFORMATION: X=cystein amide

<400> SEQUENCE: 100

Tyr Xaa Glu Gly Thr Phe Thr Ser Asp Lys Xaa Xaa Ser Ile Tyr Leu
1               5                   10                  15

Asp Lys Gln Ala Ala Xaa Glu Phe Val Asn Trp Leu Leu Ala Gly Gly
            20                  25                  30

Pro Ser Ser Gly Ala Pro Pro Pro Ser Xaa
            35                  40

<210> SEQ ID NO 101
<211> LENGTH: 43
<212> TYPE: PRT
<213> ORGANISM: Artificial Sequence
<220> FEATURE:
<223> OTHER INFORMATION: lipidated incretin receptor polypeptide 2
<220> FEATURE:
<221> NAME/KEY: MISC_FEATURE
<222> LOCATION: (1)..(1)
<223> OTHER INFORMATION: X=desAmino Tyr
<220> FEATURE:
<221> NAME/KEY: MISC_FEATURE
<222> LOCATION: (13)..(13)
<223> OTHER INFORMATION: X=gamma glutamic acid with palmitoic acid
<220> FEATURE:
<221> NAME/KEY: MISC_FEATURE
<222> LOCATION: (43)..(43)
<223> OTHER INFORMATION: X=cystein amide

<400> SEQUENCE: 101

Xaa Tyr Arg Ala Glu Gly Thr Phe Thr Ser Asp Lys Xaa Ser Lys Tyr
1               5                   10                  15

Leu Asp Glu Arg Ala Ala Gln Asp Phe Val Gln Trp Leu Leu Glu Gly
            20                  25                  30

Gly Pro Ser Ser Gly Ala Pro Pro Pro Ser Xaa
            35                  40

<210> SEQ ID NO 102
<211> LENGTH: 41
<212> TYPE: PRT
<213> ORGANISM: Artificial Sequence
<220> FEATURE:
<223> OTHER INFORMATION: lipidated incretin receptor polypeptide 3
<220> FEATURE:
<221> NAME/KEY: MISC_FEATURE
<222> LOCATION: (1)..(1)
<223> OTHER INFORMATION: X=N-acetyl-D-tyrosine
<220> FEATURE:
<221> NAME/KEY: MISC_FEATURE
<222> LOCATION: (11)..(11)
<223> OTHER INFORMATION: X=gamma glutamic acid with palmitoic acid
<220> FEATURE:
<221> NAME/KEY: MISC_FEATURE
<222> LOCATION: (41)..(41)
<223> OTHER INFORMATION: X=cystein amide

<400> SEQUENCE: 102

Xaa Ala Leu Gly Thr Phe Thr Ser Asp Lys Xaa Ser Lys Tyr Leu Asp
1               5                   10                  15
```

```
Glu Arg Ala Ala Gln Asp Phe Val Gln Trp Leu Leu Glu Gly Gly Pro
            20                  25                  30

Ser Ser Gly Ala Pro Pro Ser Xaa
            35                  40

<210> SEQ ID NO 103
<211> LENGTH: 41
<212> TYPE: PRT
<213> ORGANISM: Artificial Sequence
<220> FEATURE:
<223> OTHER INFORMATION: lipidated incretin receptor polypeptide 4
<220> FEATURE:
<221> NAME/KEY: MISC_FEATURE
<222> LOCATION: (1)..(1)
<223> OTHER INFORMATION: X=N-acetyl-d-tyrosine
<220> FEATURE:
<221> NAME/KEY: MISC_FEATURE
<222> LOCATION: (11)..(11)
<223> OTHER INFORMATION: X=gamma glutamic acid with palmitoic acid
<220> FEATURE:
<221> NAME/KEY: MISC_FEATURE
<222> LOCATION: (41)..(41)
<223> OTHER INFORMATION: X=cystein amide

<400> SEQUENCE: 103

Xaa Ala Val Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Ser Xaa
            35                  40

<210> SEQ ID NO 104
<211> LENGTH: 41
<212> TYPE: PRT
<213> ORGANISM: Artificial Sequence
<220> FEATURE:
<223> OTHER INFORMATION: lipidated incretin receptor polypeptide 5
<220> FEATURE:
<221> NAME/KEY: MISC_FEATURE
<222> LOCATION: (1)..(1)
<223> OTHER INFORMATION: X=N-acetyl-d-histidine
<220> FEATURE:
<221> NAME/KEY: MISC_FEATURE
<222> LOCATION: (11)..(11)
<223> OTHER INFORMATION: X=gamma glutamic acid with palmitoic acid
<220> FEATURE:
<221> NAME/KEY: MISC_FEATURE
<222> LOCATION: (41)..(41)
<223> OTHER INFORMATION: X=cystein amide

<400> SEQUENCE: 104

Xaa Ala Gln Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Ser Xaa
            35                  40

<210> SEQ ID NO 105
<211> LENGTH: 41
<212> TYPE: PRT
<213> ORGANISM: Artificial Sequence
<220> FEATURE:
<223> OTHER INFORMATION: lipidated incretin receptor polypeptide 6
<220> FEATURE:
<221> NAME/KEY: MISC_FEATURE
<222> LOCATION: (1)..(1)
<223> OTHER INFORMATION: X=N-acetly-d-tyrosine
```

```
<220> FEATURE:
<221> NAME/KEY: MISC_FEATURE
<222> LOCATION: (11)..(11)
<223> OTHER INFORMATION: X=gamma glutamic acid with palmitoic acid
<220> FEATURE:
<221> NAME/KEY: MISC_FEATURE
<222> LOCATION: (41)..(41)
<223> OTHER INFORMATION: X=cystein amide

<400> SEQUENCE: 105

Xaa Ala Gln Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser Xaa
        35                  40

<210> SEQ ID NO 106
<211> LENGTH: 12
<212> TYPE: PRT
<213> ORGANISM: Artificial Sequence
<220> FEATURE:
<223> OTHER INFORMATION: sortase tag acceptor
<220> FEATURE:
<221> NAME/KEY: MISC_FEATURE
<222> LOCATION: (1)..(1)
<223> OTHER INFORMATION: X=N-bromoacetyl glycine

<400> SEQUENCE: 106

Xaa Gly Gly Leu Pro Glu Thr Gly Gly Ser Gly Ser
1               5                   10

<210> SEQ ID NO 107
<211> LENGTH: 9
<212> TYPE: PRT
<213> ORGANISM: Artificial Sequence
<220> FEATURE:
<223> OTHER INFORMATION: sortase tag acceptor
<220> FEATURE:
<221> NAME/KEY: MISC_FEATURE
<222> LOCATION: (1)..(1)
<223> OTHER INFORMATION: X=N-bromoacetyl-leucine

<400> SEQUENCE: 107

Xaa Pro Glu Thr Gly Gly Ser Gly Ser
1               5

<210> SEQ ID NO 108
<211> LENGTH: 55
<212> TYPE: PRT
<213> ORGANISM: Artificial Sequence
<220> FEATURE:
<223> OTHER INFORMATION: lipidated incretin receptor polypeptide 7
<220> FEATURE:
<221> NAME/KEY: MISC_FEATURE
<222> LOCATION: (2)..(2)
<223> OTHER INFORMATION: X=aib
<220> FEATURE:
<221> NAME/KEY: MISC_FEATURE
<222> LOCATION: (11)..(11)
<223> OTHER INFORMATION: X=gamma glutamic acid
<220> FEATURE:
<221> NAME/KEY: MISC_FEATURE
<222> LOCATION: (12)..(12)
<223> OTHER INFORMATION: X=gamma glutamic acid with palmitoic acid
<220> FEATURE:
<221> NAME/KEY: MISC_FEATURE
<222> LOCATION: (22)..(22)
<223> OTHER INFORMATION: X=aib
<220> FEATURE:
<221> NAME/KEY: MISC_FEATURE
```

```
<222> LOCATION: (43)..(43)
<223> OTHER INFORMATION: X=S-CH2-CO

<400> SEQUENCE: 108

Tyr Xaa Glu Gly Thr Phe Thr Ser Asp Lys Xaa Xaa Ser Ile Tyr Leu
1               5                   10                  15

Asp Lys Gln Ala Ala Xaa Glu Phe Val Asn Trp Leu Leu Ala Gly Gly
            20                  25                  30

Pro Ser Ser Gly Ala Pro Pro Pro Ser Cys Xaa Gly Gly Gly Leu Pro
        35                  40                  45

Glu Thr Gly Gly Ser Gly Ser
        50                  55

<210> SEQ ID NO 109
<211> LENGTH: 52
<212> TYPE: PRT
<213> ORGANISM: Artificial Sequence
<220> FEATURE:
<223> OTHER INFORMATION: lipidated incretin receptor polypeptide 8
<220> FEATURE:
<221> NAME/KEY: MISC_FEATURE
<222> LOCATION: (2)..(2)
<223> OTHER INFORMATION: X=aib
<220> FEATURE:
<221> NAME/KEY: MISC_FEATURE
<222> LOCATION: (11)..(11)
<223> OTHER INFORMATION: X=gamma glutamic acid
<220> FEATURE:
<221> NAME/KEY: MISC_FEATURE
<222> LOCATION: (12)..(12)
<223> OTHER INFORMATION: X=gamma glutamic acid with palmitoic acid
<220> FEATURE:
<221> NAME/KEY: MISC_FEATURE
<222> LOCATION: (22)..(22)
<223> OTHER INFORMATION: X=aib
<220> FEATURE:
<221> NAME/KEY: MISC_FEATURE
<222> LOCATION: (43)..(43)
<223> OTHER INFORMATION: X=S-CH2-CO

<400> SEQUENCE: 109

Tyr Xaa Glu Gly Thr Phe Thr Ser Asp Lys Xaa Xaa Ser Ile Tyr Leu
1               5                   10                  15

Asp Lys Gln Ala Ala Xaa Glu Phe Val Asn Trp Leu Leu Ala Gly Gly
            20                  25                  30

Pro Ser Ser Gly Ala Pro Pro Pro Ser Cys Xaa Leu Pro Glu Thr Gly
        35                  40                  45

Gly Ser Gly Ser
    50

<210> SEQ ID NO 110
<211> LENGTH: 54
<212> TYPE: PRT
<213> ORGANISM: Artificial Sequence
<220> FEATURE:
<223> OTHER INFORMATION: lipidated incretin receptor polypeptide 9
<220> FEATURE:
<221> NAME/KEY: MISC_FEATURE
<222> LOCATION: (1)..(1)
<223> OTHER INFORMATION: X=deasAmino-tyrosine
<220> FEATURE:
<221> NAME/KEY: MISC_FEATURE
<222> LOCATION: (11)..(11)
<223> OTHER INFORMATION: X=gamma glutamic acid with palmitoic acid
<220> FEATURE:
<221> NAME/KEY: MISC_FEATURE
<222> LOCATION: (42)..(42)
<223> OTHER INFORMATION: X=S-CH2-CO
```

<400> SEQUENCE: 110

Xaa Ala Glu Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser Cys Xaa Gly Gly Gly Leu Pro Glu
        35                  40                  45

Thr Gly Gly Ser Gly Ser
    50

<210> SEQ ID NO 111
<211> LENGTH: 54
<212> TYPE: PRT
<213> ORGANISM: Artificial Sequence
<220> FEATURE:
<223> OTHER INFORMATION: lipidated incretin receptor polypeptide 10
<220> FEATURE:
<221> NAME/KEY: MISC_FEATURE
<222> LOCATION: (1)..(1)
<223> OTHER INFORMATION: X=N-acetyl-d-tyrosine
<220> FEATURE:
<221> NAME/KEY: MISC_FEATURE
<222> LOCATION: (11)..(11)
<223> OTHER INFORMATION: X=gamma glutamic acid with palmitoic acid
<220> FEATURE:
<221> NAME/KEY: MISC_FEATURE
<222> LOCATION: (42)..(42)
<223> OTHER INFORMATION: X=S-CH2-CO

<400> SEQUENCE: 111

Xaa Ala Leu Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser Cys Xaa Gly Gly Gly Leu Pro Glu
        35                  40                  45

Thr Gly Gly Ser Gly Ser
    50

<210> SEQ ID NO 112
<211> LENGTH: 54
<212> TYPE: PRT
<213> ORGANISM: Artificial Sequence
<220> FEATURE:
<223> OTHER INFORMATION: lipidated incretin receptor polypeptide 11
<220> FEATURE:
<221> NAME/KEY: MISC_FEATURE
<222> LOCATION: (1)..(1)
<223> OTHER INFORMATION: X=N-acetyl-d-tyrosine
<220> FEATURE:
<221> NAME/KEY: MISC_FEATURE
<222> LOCATION: (11)..(11)
<223> OTHER INFORMATION: X=gamma glutamic acid with palmitoic acid
<220> FEATURE:
<221> NAME/KEY: MISC_FEATURE
<222> LOCATION: (42)..(42)
<223> OTHER INFORMATION: X=S-CH2-CO

<400> SEQUENCE: 112

Xaa Ala Val Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser Cys Xaa Gly Gly Gly Leu Pro Glu
        35                  40                  45

```
Thr Gly Gly Ser Gly Ser
    50

<210> SEQ ID NO 113
<211> LENGTH: 54
<212> TYPE: PRT
<213> ORGANISM: Artificial Sequence
<220> FEATURE:
<223> OTHER INFORMATION: lipidated incretin receptor polypeptide 12
<220> FEATURE:
<221> NAME/KEY: MISC_FEATURE
<222> LOCATION: (1)..(1)
<223> OTHER INFORMATION: X=N-acetyl-d-histidine
<220> FEATURE:
<221> NAME/KEY: MISC_FEATURE
<222> LOCATION: (11)..(11)
<223> OTHER INFORMATION: X=gamma glutamic acid with palmitoic acid
<220> FEATURE:
<221> NAME/KEY: MISC_FEATURE
<222> LOCATION: (42)..(42)
<223> OTHER INFORMATION: X=S-CH2-CO

<400> SEQUENCE: 113

Xaa Ala Gln Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser Cys Xaa Gly Gly Gly Leu Pro Glu
        35                  40                  45

Thr Gly Gly Ser Gly Ser
    50

<210> SEQ ID NO 114
<211> LENGTH: 54
<212> TYPE: PRT
<213> ORGANISM: Artificial Sequence
<220> FEATURE:
<223> OTHER INFORMATION: lipidated incretin receptor polypeptide 13
<220> FEATURE:
<221> NAME/KEY: MISC_FEATURE
<222> LOCATION: (1)..(1)
<223> OTHER INFORMATION: X=N-acetyl-d-tyrosine
<220> FEATURE:
<221> NAME/KEY: MISC_FEATURE
<222> LOCATION: (11)..(11)
<223> OTHER INFORMATION: X=gamma glutamic acid with palmitoic acid
<220> FEATURE:
<221> NAME/KEY: MISC_FEATURE
<222> LOCATION: (42)..(42)
<223> OTHER INFORMATION: X=S-CH2-CO

<400> SEQUENCE: 114

Xaa Ala Gln Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser Cys Xaa Gly Gly Gly Leu Pro Glu
        35                  40                  45

Thr Gly Gly Ser Gly Ser
    50

<210> SEQ ID NO 115
<211> LENGTH: 40
<212> TYPE: PRT
<213> ORGANISM: Artificial Sequence
<220> FEATURE:
<223> OTHER INFORMATION: lipidated incretin receptor polypeptide 14
<220> FEATURE:
```

```
<221> NAME/KEY: MISC_FEATURE
<222> LOCATION: (1)..(1)
<223> OTHER INFORMATION: X=N-acetyl-d-histidine
<220> FEATURE:
<221> NAME/KEY: MISC_FEATURE
<222> LOCATION: (11)..(11)
<223> OTHER INFORMATION: X=gamma glutamic acid with palmitoic acid

<400> SEQUENCE: 115

Xaa Ala Gln Gly Thr Phe Thr Ser Asp Lys Xaa Ser Lys Tyr Leu Asp
1               5                   10                  15

Glu Arg Ala Ala Gln Asp Phe Val Gln Trp Leu Leu Gly Gly Gly Leu
            20                  25                  30

Pro Glu Thr Gly Gly Ser Gly Ser
        35                  40

<210> SEQ ID NO 116
<211> LENGTH: 52
<212> TYPE: PRT
<213> ORGANISM: Artificial Sequence
<220> FEATURE:
<223> OTHER INFORMATION: lipidated incretin receptor polypeptide 15
<220> FEATURE:
<221> NAME/KEY: MISC_FEATURE
<222> LOCATION: (1)..(1)
<223> OTHER INFORMATION: X=N-acetyl-d-tyrosine
<220> FEATURE:
<221> NAME/KEY: MISC_FEATURE
<222> LOCATION: (11)..(11)
<223> OTHER INFORMATION: X=gamma glutamic acid with palmitoic acid

<400> SEQUENCE: 116

Xaa Ala Leu Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser Gly Gly Gly Leu Pro Glu Thr Gly
        35                  40                  45

Gly Ser Gly Ser
    50

<210> SEQ ID NO 117
<211> LENGTH: 230
<212> TYPE: PRT
<213> ORGANISM: Artificial Sequence
<220> FEATURE:
<223> OTHER INFORMATION: triple G human immunoglobulin IgG1 Fc-region
      with mutations L234A, L235A, P329G

<400> SEQUENCE: 117

Gly Gly Gly Asp Lys Thr His Thr Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Gly
```

```
                100                 105                 110
Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
            130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
            195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 118
<211> LENGTH: 49
<212> TYPE: PRT
<213> ORGANISM: Artificial Sequence
<220> FEATURE:
<223> OTHER INFORMATION: long incretin receptor ligand polypeptide with
      sortase tag
<220> FEATURE:
<221> NAME/KEY: MISC_FEATURE
<222> LOCATION: (2)..(2)
<223> OTHER INFORMATION: X=aib
<220> FEATURE:
<221> NAME/KEY: MISC_FEATURE
<222> LOCATION: (20)..(20)
<223> OTHER INFORMATION: X=aib
<220> FEATURE:
<221> NAME/KEY: MISC_FEATURE
<222> LOCATION: (49)..(49)
<223> OTHER INFORMATION: X=serine-amide

<400> SEQUENCE: 118

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Leu Pro Glu Thr Gly Gly Ser Gly
        35                  40                  45

Xaa

<210> SEQ ID NO 119
<211> LENGTH: 40
<212> TYPE: PRT
<213> ORGANISM: Artificial Sequence
<220> FEATURE:
<223> OTHER INFORMATION: short incretin receptor ligand polypeptide with
      sortase tag
<220> FEATURE:
<221> NAME/KEY: MISC_FEATURE
<222> LOCATION: (2)..(2)
<223> OTHER INFORMATION: X=aib
<220> FEATURE:
<221> NAME/KEY: MISC_FEATURE
<222> LOCATION: (20)..(20)
<223> OTHER INFORMATION: X=aib
<220> FEATURE:
<221> NAME/KEY: MISC_FEATURE
<222> LOCATION: (40)..(40)
```

<223> OTHER INFORMATION: X=serine amide

<400> SEQUENCE: 119

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Gly Leu
            20                  25                  30

Pro Glu Thr Gly Gly Ser Gly Xaa
        35                  40

<210> SEQ ID NO 120
<211> LENGTH: 41
<212> TYPE: PRT
<213> ORGANISM: Artificial Sequence
<220> FEATURE:
<223> OTHER INFORMATION: isolated lipidated incretin receptor
      polypeptide 1
<220> FEATURE:
<221> NAME/KEY: MISC_FEATURE
<222> LOCATION: (2)..(2)
<223> OTHER INFORMATION: X=aib
<220> FEATURE:
<221> NAME/KEY: MISC_FEATURE
<222> LOCATION: (11)..(11)
<223> OTHER INFORMATION: X=gamma glutamic acid
<220> FEATURE:
<221> NAME/KEY: MISC_FEATURE
<222> LOCATION: (12)..(12)
<223> OTHER INFORMATION: X=gamma glutamic acid with palmytoic acid ester
<220> FEATURE:
<221> NAME/KEY: MISC_FEATURE
<222> LOCATION: (22)..(22)
<223> OTHER INFORMATION: X=aib

<400> SEQUENCE: 120

Tyr Xaa Glu Gly Thr Phe Thr Ser Asp Lys Xaa Xaa Ser Ile Tyr Leu
1               5                   10                  15

Asp Lys Gln Ala Ala Xaa Glu Phe Val Asn Trp Leu Leu Ala Gly Gly
            20                  25                  30

Pro Ser Ser Gly Ala Pro Pro Pro Ser
        35                  40

<210> SEQ ID NO 121
<211> LENGTH: 42
<212> TYPE: PRT
<213> ORGANISM: Artificial Sequence
<220> FEATURE:
<223> OTHER INFORMATION: isolated lipidated incretin receptor
      polypeptide 2
<220> FEATURE:
<221> NAME/KEY: MISC_FEATURE
<222> LOCATION: (1)..(1)
<223> OTHER INFORMATION: X=desAmino Tyr
<220> FEATURE:
<221> NAME/KEY: MISC_FEATURE
<222> LOCATION: (13)..(13)
<223> OTHER INFORMATION: X=gamma glutamic acid with palmitoic acid

<400> SEQUENCE: 121

Xaa Tyr Arg Ala Glu Gly Thr Phe Thr Ser Asp Lys Xaa Ser Lys Tyr
1               5                   10                  15

Leu Asp Glu Arg Ala Ala Gln Asp Phe Val Gln Trp Leu Leu Glu Gly
            20                  25                  30

Gly Pro Ser Ser Gly Ala Pro Pro Pro Ser
        35                  40

<210> SEQ ID NO 122

```
<211> LENGTH: 40
<212> TYPE: PRT
<213> ORGANISM: Artificial Sequence
<220> FEATURE:
<223> OTHER INFORMATION: isolated lipidated incretin receptor
      polypeptide 3
<220> FEATURE:
<221> NAME/KEY: MISC_FEATURE
<222> LOCATION: (1)..(1)
<223> OTHER INFORMATION: X=N-acetyl-D-tyrosine
<220> FEATURE:
<221> NAME/KEY: MISC_FEATURE
<222> LOCATION: (11)..(11)
<223> OTHER INFORMATION: X=gamma glutamic acid with palmitoic acid

<400> SEQUENCE: 122

Xaa Ala Leu Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser
        35                  40

<210> SEQ ID NO 123
<211> LENGTH: 40
<212> TYPE: PRT
<213> ORGANISM: Artificial Sequence
<220> FEATURE:
<223> OTHER INFORMATION: isolated lipidated incretin receptor
      polypeptide 4
<220> FEATURE:
<221> NAME/KEY: MISC_FEATURE
<222> LOCATION: (1)..(1)
<223> OTHER INFORMATION: X=N-acetyl-d-tyrosine
<220> FEATURE:
<221> NAME/KEY: MISC_FEATURE
<222> LOCATION: (11)..(11)
<223> OTHER INFORMATION: X=gamma glutamic acid with palmitoic acid

<400> SEQUENCE: 123

Xaa Ala Val Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser
        35                  40

<210> SEQ ID NO 124
<211> LENGTH: 40
<212> TYPE: PRT
<213> ORGANISM: Artificial Sequence
<220> FEATURE:
<223> OTHER INFORMATION: isolated lipidated incretin receptor
      polypeptide 5
<220> FEATURE:
<221> NAME/KEY: MISC_FEATURE
<222> LOCATION: (1)..(1)
<223> OTHER INFORMATION: X=N-acetyl-d-histidine
<220> FEATURE:
<221> NAME/KEY: MISC_FEATURE
<222> LOCATION: (11)..(11)
<223> OTHER INFORMATION: X=gamma glutamic acid with palmitoic acid

<400> SEQUENCE: 124

Xaa Ala Gln Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30
```

```
Ser Ser Gly Ala Pro Pro Pro Ser
        35                  40

<210> SEQ ID NO 125
<211> LENGTH: 40
<212> TYPE: PRT
<213> ORGANISM: Artificial Sequence
<220> FEATURE:
<223> OTHER INFORMATION: isolated lipidated incretin receptor
      polypeptide 6
<220> FEATURE:
<221> NAME/KEY: MISC_FEATURE
<222> LOCATION: (1)..(1)
<223> OTHER INFORMATION: X=N-acetly-d-tyrosine
<220> FEATURE:
<221> NAME/KEY: MISC_FEATURE
<222> LOCATION: (11)..(11)
<223> OTHER INFORMATION: X=gamma glutamic acid with palmitoic acid

<400> SEQUENCE: 125

Xaa Ala Gln Gly Thr Phe Thr Ser Asp Lys Xaa Ser Lys Tyr Leu Asp
1               5                   10                  15

Glu Arg Ala Ala Gln Asp Phe Val Gln Trp Leu Leu Glu Gly Gly Pro
            20                  25                  30

Ser Ser Gly Ala Pro Pro Pro Ser
        35                  40
```